US012472353B2

(12) United States Patent
Deslauriers

(10) Patent No.: US 12,472,353 B2
(45) Date of Patent: Nov. 18, 2025

(54) TRANSDUCER ARRAY FLEXIBILITY AND METHODS OF PRODUCTION AND USE THEREOF

(71) Applicant: Novocure GmbH, Root (CH)

(72) Inventor: Richard Deslauriers, Woodbury, CT (US)

(73) Assignee: Novocure GmbH (CH)

( * ) Notice: Subject to any disclaimer, the term of this patent is extended or adjusted under 35 U.S.C. 154(b) by 69 days.

(21) Appl. No.: 18/511,702

(22) Filed: Nov. 16, 2023

(65) Prior Publication Data

US 2024/0157135 A1 May 16, 2024

Related U.S. Application Data

(63) Continuation of application No. 17/313,114, filed on May 6, 2021.

(60) Provisional application No. 63/141,315, filed on Jan. 25, 2021, provisional application No. 63/128,276, filed on Dec. 21, 2020, provisional application No. (Continued)

(51) Int. Cl.
*A61N 1/36* (2006.01)
*A61N 1/04* (2006.01)
*A61N 1/40* (2006.01)

(52) U.S. Cl.
CPC ....... *A61N 1/36002* (2017.08); *A61N 1/0492* (2013.01); *A61N 1/36034* (2017.08); *A61N 1/40* (2013.01)

(58) Field of Classification Search
None
See application file for complete search history.

(56) References Cited

U.S. PATENT DOCUMENTS

| | | | |
|---|---|---|---|
| 5,285,415 | A | 2/1994 | Buckley et al. |
| 5,974,344 | A | 10/1999 | Shoemaker, II |

(Continued)

FOREIGN PATENT DOCUMENTS

| | | | |
|---|---|---|---|
| CN | 103585715 | A | 2/2014 |
| CN | 110180082 | A | 8/2019 |

(Continued)

OTHER PUBLICATIONS

International Search Report and Written Opinion (PCT/US2021/031119); Aug. 25, 2021; 12 pgs.

(Continued)

*Primary Examiner* — Michael W Kahelin
(74) *Attorney, Agent, or Firm* — Dunlap Codding, P.C.

(57) ABSTRACT

A conductive pad is described. The conductive pad includes a topcoat layer, an electrode element, and a conductive gel element. The topcoat layer is constructed of a non-conductive material. The electrode element has a first side and a second side, the second side connected to the topcoat layer, and configured to receive an electrical signal from a generator producing an electric signal as a TTField. The conductive gel element is connected to the first side of the electrode element and electrically coupled to the electrode element so as to receive an electrical current from the electrode element, the conductive gel element being in the form of at least one line and operable to be in contact with a patient's skin at specific locations and operable to flex with movement of the patient without substantially moving from the specific location.

19 Claims, 27 Drawing Sheets

Related U.S. Application Data

63/085,476, filed on Sep. 30, 2020, provisional application No. 63/068,213, filed on Aug. 20, 2020, provisional application No. 63/061,316, filed on Aug. 5, 2020, provisional application No. 63/061,419, filed on Aug. 5, 2020, provisional application No. 63/046, 364, filed on Jun. 30, 2020, provisional application No. 63/030,138, filed on May 26, 2020, provisional application No. 63/020,636, filed on May 6, 2020.

(56) References Cited

U.S. PATENT DOCUMENTS

| | | | | |
|---|---|---|---|---|
| 6,038,464 | A | 3/2000 | Axelgaard et al. | |
| 6,263,226 | B1 | 7/2001 | Axelgarrd et al. | |
| 6,317,629 | B1 | 11/2001 | Haak et al. | |
| 6,347,246 | B1 | 2/2002 | Perrault et al. | |
| 7,016,725 | B2 | 3/2006 | Palti | |
| 7,089,054 | B2 | 8/2006 | Palti | |
| 7,146,210 | B2 | 12/2006 | Palti | |
| 7,333,852 | B2 | 2/2008 | Palti | |
| 7,565,205 | B2 | 7/2009 | Palti | |
| 8,244,345 | B2 | 8/2012 | Palti | |
| 8,715,203 | B2 | 5/2014 | Palti | |
| 8,764,675 | B2 | 7/2014 | Palti | |
| 9,731,108 | B2 | 8/2017 | Mathew et al. | |
| 10,188,851 | B2 | 1/2019 | Wenger et al. | |
| 10,441,776 | B2 | 10/2019 | Kirson et al. | |
| 11,058,886 | B1 | 7/2021 | Matloubian et al. | |
| 2002/0183804 | A1 | 12/2002 | Malaney et al. | |
| 2003/0069627 | A1* | 4/2003 | Giuntoli | A61N 1/0408 607/149 |
| 2003/0134545 | A1 | 7/2003 | McAdams et al. | |
| 2003/0153964 | A1 | 8/2003 | Al-Lamee et al. | |
| 2006/0276858 | A1 | 12/2006 | Palti | |
| 2009/0002067 | A1 | 1/2009 | Kronberg | |
| 2009/0043346 | A1 | 2/2009 | Palti et al. | |
| 2010/0191316 | A1* | 7/2010 | Buhlmann | A61N 1/0452 607/148 |
| 2010/0204560 | A1 | 8/2010 | Salahieh | |
| 2012/0149968 | A1 | 6/2012 | Brighton | |
| 2014/0073896 | A1 | 3/2014 | Hyatt et al. | |
| 2015/0321000 | A1 | 11/2015 | Rosenbluth et al. | |
| 2017/0157398 | A1 | 6/2017 | Wong et al. | |
| 2017/0165470 | A1 | 6/2017 | Jeffery | |
| 2018/0117302 | A1 | 5/2018 | Clegg | |
| 2018/0160933 | A1 | 6/2018 | Urman et al. | |
| 2019/0048193 | A1 | 2/2019 | Naier et al. | |
| 2019/0117956 | A1 | 4/2019 | Wenger et al. | |
| 2019/0217078 | A1 | 7/2019 | Yang et al. | |
| 2019/0217079 | A1 | 7/2019 | Kato et al. | |
| 2019/0307781 | A1 | 10/2019 | Krex et al. | |
| 2019/0308016 | A1 | 10/2019 | Wenger et al. | |
| 2019/0314638 | A1 | 10/2019 | Kreindel | |
| 2019/0321636 | A1 | 10/2019 | Law et al. | |
| 2020/0101278 | A1 | 4/2020 | Freeman et al. | |
| 2020/0324107 | A1 | 10/2020 | Nishizawa | |
| 2021/0213280 | A1 | 7/2021 | Kuwahata | |
| 2021/0290944 | A1* | 9/2021 | Hong | A61N 1/32 |
| 2022/0218983 | A1 | 7/2022 | Brooks et al. | |

FOREIGN PATENT DOCUMENTS

| | | | |
|---|---|---|---|
| EP | 3067073 | A1 | 9/2016 |
| JP | 2002501804 | A | 1/2002 |
| JP | 2004510481 | A | 4/2004 |
| JP | 2006513739 | A | 4/2006 |
| JP | 2010532644 | A | 10/2010 |
| JP | 2019524206 | A | 9/2019 |
| JP | 2022567156 | A | 6/2023 |
| KR | 1020100028761 | | 3/2010 |
| WO | WO 99/39635 | | 8/1999 |
| WO | WO 0228279 | A1 | 4/2002 |
| WO | WO 2004030760 | A3 | 4/2004 |
| WO | WO 2009003123 | A1 | 12/2008 |
| WO | WO 2018002879 | A1 | 1/2018 |
| WO | WO 2018/081423 | A1 | 5/2018 |
| WO | WO 2020070914 | A1 | 9/2020 |

OTHER PUBLICATIONS

Japanese Patent Office, Notification of Reasons for Refusal regarding Japanese Patent Application No. 2022-567156 (English machine translation from JPO J-PlatPat); Feb. 18, 2025; 16 pgs.

* cited by examiner

180

| Thermometer (184) | 100a | 100b | 164a | 164b |
|---|---|---|---|---|
| 184a | 23.7 | 23.3 | 39.6 | 31.8 |
| 184b | 23.7 | 22.6 | 35.5 | 32.7 |
| 184c | 23.9 | 23.1 | 36.6 | 33.1 |
| 184d | 22.9 | 23.3 | 30.6 | 33.6 |
| 184e | 23.3 | 22.8 | 34.0 | 34.8 |
| 184f | 23.3 | 23.3 | 36.4 | 35.5 |
| 184g | 23.5 | 23.1 | 36.8 | 34.8 |
| 184h | 22.8 | 23.3 | 39.3 | 36.1 |

TRANSDUCER ARRAY FLEXIBILITY AND METHODS OF PRODUCTION AND USE THEREOF

CROSS REFERENCE TO RELATED APPLICATIONS

This application is a continuation application claiming priority to U.S. application Ser. No. 17/313,114 filed May 6, 2021, which claims priority to: U.S. Provisional Application No. 63/020,636, filed May 6, 2020, U.S. Provisional Application No. 63/046,364, filed Jun. 30, 2020, U.S. Provisional Application No. 63/030,138, filed May 26, 2020, U.S. Provisional Application No. 63/068,213, filed Aug. 20, 2020, U.S. Provisional Application No. 63/061,316, filed Aug. 5, 2020, U.S. Provisional Application No. 63/061,419, filed Aug. 5, 2020, U.S. Provisional Application No. 63/085,476, filed Sep. 30, 2020, U.S. Provisional Application No. 63/141,315, filed Jan. 25, 2021, and U.S. Provisional Application No. 63/128,276, filed Dec. 21, 2020. The entire content of each of the above-referenced applications is hereby expressly incorporated herein by reference in its entirety.

STATEMENT OF FEDERALLY SPONSORED RESEARCH

Not Applicable.

BACKGROUND ART

Tumor Treating Fields (TTFields or TTFs) are low intensity (e.g., 1-3 V/cm) alternating electric fields within the intermediate frequency range (100-576 kHz) that target solid tumors by disrupting mitosis. This non-invasive treatment targets solid tumors and is described, for example, in U.S. Pat. Nos. 7,016,725; 7,089,054; 7,333,852; 7,565,205; 8,244,345; 8,715,203; 8,764,675; 10,188,851; and 10,441,776. TTFields are typically delivered through two pairs of transducer arrays that generate perpendicular fields within the treated tumor; the transducer arrays that make up each of these pairs are positioned on opposite sides of the body part that is being treated. More specifically, for the OPTUNE® system, one pair of electrodes of the transducer array is located to the left and right (LR) of the tumor, and the other pair of electrodes of the transducer array is located anterior and posterior (AP) to the tumor. TTFields are approved for the treatment of glioblastoma multiforme (GBM), and may be delivered, for example, via the OPTUNE® system (Novocure Limited, St. Helier, Jersey), which includes transducer arrays placed on the patient's shaved head.

Each transducer array used for the delivery of TTFields in the OPTUNE® device comprises a set of non-conductive ceramic disk electrodes, which are coupled to the patient's skin (such as, but not limited to, the patient's shaved head for treatment of GBM) through a layer of conductive medical gel. To form the ceramic disk electrodes, a conductive layer is formed on a top surface of nonconductive ceramic material. A bottom surface of the nonconductive ceramic material is coupled to the conductive medical gel. The nonconductive ceramic material is a safety feature to ensure that direct-current signals are blocked from unintentionally being transmitted to the patient by mistake.

By interposing a nonconductive ceramic material between the conductive layer and the conductive medical gel, the prior art system was thought to ensure the patient remains protected. The purpose of the medical gel is to deform to match the body's contours and to provide good electrical contact between the arrays and the skin; as such, the gel interface bridges the skin and reduces interference. The device is intended to be continuously worn by the patient for 2-4 days before removal for hygienic care and re-shaving (if necessary), followed by reapplication with a new set of arrays. As such, the medical gel remains in substantially continuous contact with an area of the patient's skin for a period of 2-4 days at a time, and there is only a brief period of time in which the area of skin is uncovered and exposed to the environment before more medical gel is applied thereto.

One approach to applying the TTField in different directions is to apply the field between a first set of electrodes for a period of time, then applying a field between a second set of electrodes for a period of time, then repeating that cycle for an extended duration (e.g., over a period of days or weeks).

In order to generate the TTFields, current is applied to each electrode of the transducer array. The application of current over a period of time causes each electrode to warm and eventually become hot, and thus uncomfortable or painful to the patient. In order to maintain the temperature of the transducer array, the current applied is lowered, resulting in a weaker TTField, or the transducer array is powered off, thus shortening the duration of treatment. Additionally, the prior art teaches electrodes made from rigid and/or inflexible materials, such as ceramics, which do not contour to the patient.

Because of this heating of the transducer array, new and improved array assemblies that reduce the temperature of the transducer array while generating a more powerful TTField is desired. It is to such assemblies and methods of producing and using the same, that the present disclosure is directed.

DETAILED DESCRIPTION

Figure 1:
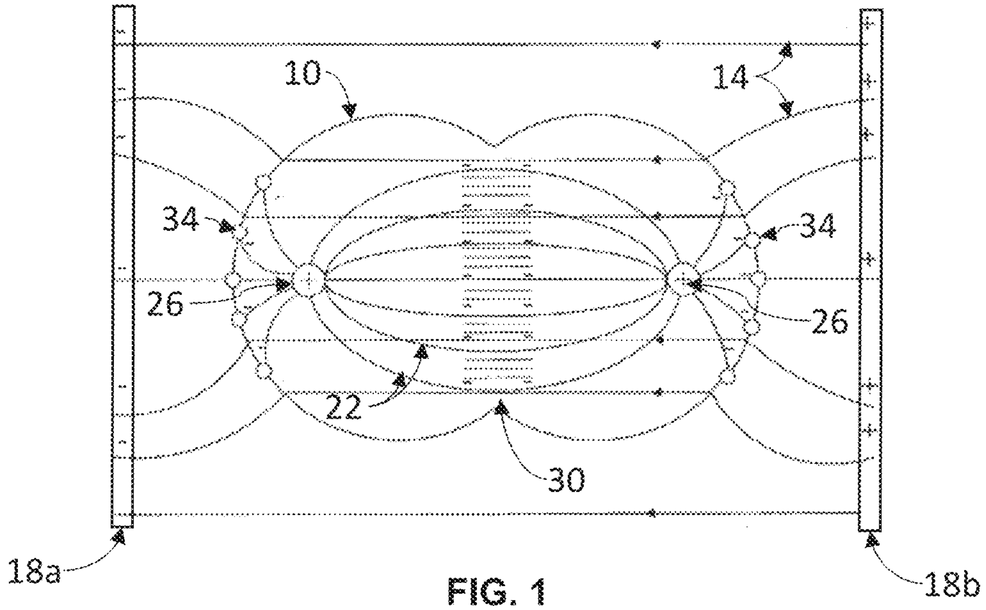
FIG. 1 is an exemplary embodiment of a schematic diagram of electrodes as applied to living tissue.

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which this presently disclosed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions, assemblies, systems, kits, and/or methods disclosed herein can be made and executed without undue experimentation in light of the present disclosure. While the compositions, assemblies, systems, kits, and methods of the inventive concept(s) have been described in terms of particular embodiments, it will be apparent to those of skill in the art that variations may be applied to the compositions and/or methods and in the steps or in the sequence of steps of the methods described herein without departing from the concept, spirit, and scope of the inventive concept(s). All such similar substitutions and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. For example, the term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The term "polypeptide" as used herein will be understood to refer to a polymer of amino acids. The polymer may include d-, l-, or artificial variants of amino acids. In addition, the term "polypeptide" will be understood to include peptides, proteins, and glycoproteins.

The term "polynucleotide" as used herein will be understood to refer to a polymer of two or more nucleotides. Nucleotides, as used herein, will be understood to include deoxyribose nucleotides and/or ribose nucleotides, as well as artificial variants thereof. The term polynucleotide also includes single-stranded and double-stranded molecules.

The terms "analog" or "variant" as used herein will be understood to refer to a variation of the normal or standard form or the wild-type form of molecules. For polypeptides or polynucleotides, an analog may be a variant (polymorphism), a mutant, and/or a naturally or artificially chemically modified version of the wild-type polynucleotide (including combinations of the above). Such analogs may have higher, full, intermediate, or lower activity than the normal form of the molecule, or no activity at all. Alternatively, and/or in addition thereto, for a chemical, an analog may be any structure that has the desired functionalities (including alterations or substitutions in the core moiety), even if comprised of different atoms or isomeric arrangements.

As used herein, the phrases "associated with" and "coupled to" include both direct association/binding of two moieties to one another as well as indirect association/binding of two moieties to one another. Non-limiting examples of associations/couplings include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "pharmaceutically acceptable" refers to compounds and compositions which are suitable for administration to humans and/or animals without undue adverse side effects such as (but not limited to) toxicity, irritation, and/or allergic response commensurate with a reasonable benefit/risk ratio.

The term "pharmaceutically-acceptable excipient" refers to any carrier, vehicle, and/or diluent known in the art or otherwise contemplated herein that may improve solubility, deliverability, dispersion, stability, and/or conformational integrity of the compositions disclosed herein.

The term "patient" as used herein includes human and veterinary subjects. "Mammal" for purposes of treatment refers to any animal classified as a mammal, including (but not limited to) humans, domestic and farm animals, nonhuman primates, and any other animal that has mammary tissue.

The term "treatment" refers to both therapeutic treatment and prophylactic or preventative measures. Those in need of treatment include, but are not limited to, individuals already having a particular condition/disease/infection as well as individuals who are at risk of acquiring a particular condition/disease/infection (e.g., those needing prophylactic/preventative measures). The term "treating" refers to administering an agent/element/method to a patient for therapeutic and/or prophylactic/preventative purposes.

A "therapeutic composition" or "pharmaceutical composition" refers to an agent that may be administered in vivo to bring about a therapeutic and/or prophylactic/preventative effect.

Administering a therapeutically effective amount or prophylactically effective amount is intended to provide a therapeutic benefit in the treatment, prevention, and/or management of a disease, condition, and/or infection. The specific amount that is therapeutically effective can be readily determined by the ordinary medical practitioner, and can vary depending on factors known in the art, such as (but not limited to) the type of condition/disease/infection, the patient's history and age, the stage of the condition/disease/infection, and the co-administration of other agents.

The term "effective amount" refers to an amount of a biologically active molecule or conjugate or derivative thereof, or an amount of a treatment protocol (i.e., an alternating electric field), sufficient to exhibit a detectable therapeutic effect without undue adverse side effects (such as (but not limited to) toxicity, electrolysis, irritation, and allergic response) commensurate with a reasonable benefit/risk ratio when used in the manner of the inventive concept(s). The therapeutic effect may include, for example but not by way of limitation, preventing, inhibiting, or reducing the occurrence of at least one tumor and/or cancer. The effective amount for a subject will depend upon the type of subject, the subject's size and health, the nature and severity of the condition/disease/infection to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "concurrent therapy" is used interchangeably with the terms "combination therapy" and "adjunct therapy," and will be understood to mean that the patient in need of treatment is treated or given another drug for the condition/disease/infection in conjunction with the treatments of the present disclosure. This concurrent therapy can be sequential therapy, where the patient is treated first with one treatment protocol/pharmaceutical composition and then the other treatment protocol/pharmaceutical composition, or the two treatment protocols/pharmaceutical compositions are given simultaneously.

The terms "administration" and "administering," as used herein, will be understood to include all routes of administration known in the art, including but not limited to, oral, topical, transdermal, parenteral, subcutaneous, intranasal, mucosal, intramuscular, intraperitoneal, intravitreal, and intravenous routes, and including both local and systemic applications. In addition, the compositions of the present disclosure (and/or the methods of administration of same) may be designed to provide delayed, controlled, or sustained release using formulation techniques which are well known in the art.

Circuitry, as used herein, may be analog and/or digital components, or one or more suitably programmed processors (e.g., microprocessors) and associated hardware and software, or hardwired logic. Also, "components" may perform one or more functions. The term "component," may include hardware, such as a processor (e.g., microprocessor), an application specific integrated circuit (ASIC), a field programmable gate array (FPGA), a combination of hardware and software, and/or the like. The term "processor" as used herein means a single processor or multiple processors working independently or together to collectively perform a task.

Turning now to the inventive concept(s), certain non-limiting embodiments thereof include a system and method of implementing the system, the system comprising a generator configured to generate an electrical signal having an alternating current waveform at a frequency in a range from 50 kHz to 576 kHz; a first conductive lead electrically coupled to the generator, the first conductive lead configured to carry the electrical signal; and an a pad electrically coupled to the first conductive lead. Various aspects of the present disclosure are provided in detail below.

Referring now to the drawings and in particular to FIG. 1, shown therein is an exemplary embodiment of a dividing cell 10, under the influence of external TTFields (e.g., alternating fields in the frequency range of about 100 kHz to about 300 kHz), generally indicated as lines 14, generated by a first electrode 18*a* having a negative charge and a second electrode 18*b* having a positive charge. Further shown are microtubules 22 that are known to have a very strong dipole moment. This strong polarization makes the microtubules 22, as well as other polar macromolecules and especially those that have a specific orientation within the cell 10 or its surroundings, susceptible to electric fields. The microtubules 22 positive charges are located at two centrioles 26 while two sets of negative poles are at a center 30 of the dividing cell 10 and point of attachment 34 of the microtubules 22 to the cell membrane. The locations of the charges form sets of double dipoles and therefore are susceptible to electric fields of differing directions. In one embodiment, the cells go through electroporation, that is, DNA or chromosomes are introduced into the cells using a pulse of electricity to briefly open pores in the cell membranes.

Figure 2:
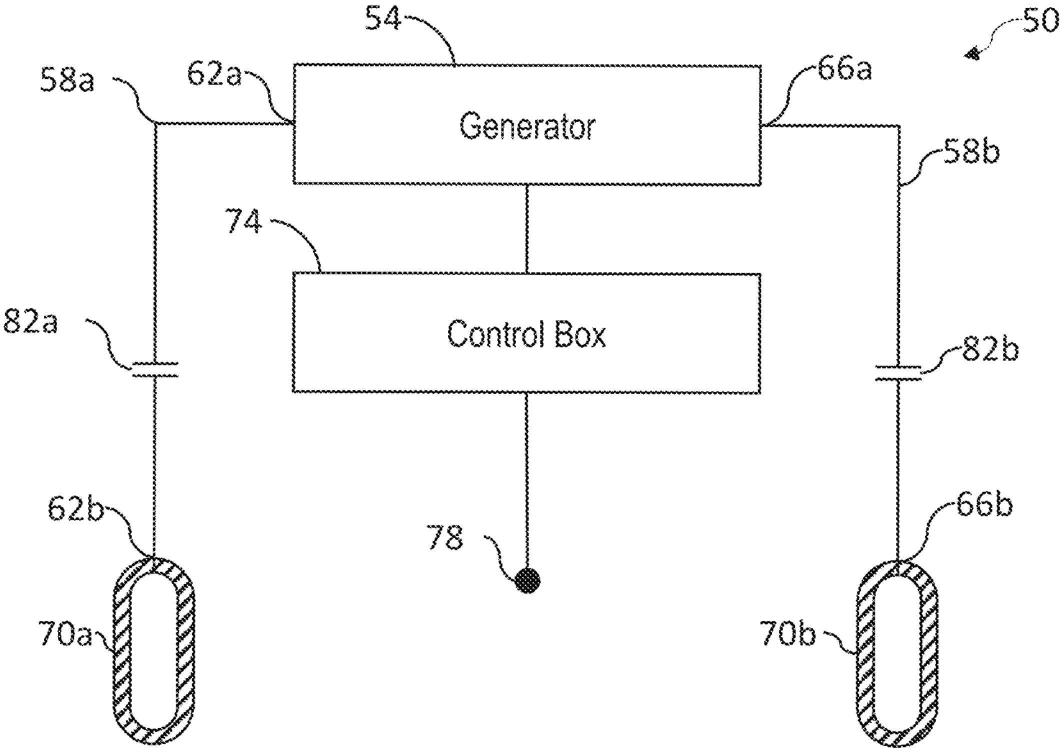
FIG. 2 is an exemplary embodiment of an electronic device configured to generate a TTField.

Turning now to FIG. 2, the TTFields described above that have been found to advantageously destroy tumor cells are generated by an electronic apparatus 50. FIG. 2 is a simple schematic diagram of the electronic apparatus 50 illustrating major components thereof. The electronic apparatus 50 includes a generator 54 and a pair of conductive leads 58, including first conductive lead 58*a* and second conductive lead 58*b*. The first conductive lead 58*a* includes a first end 62*a* and a second end 62*b*. The second conductive lead 58*b* includes a first end 66*a* and a second end 66*b*. The first end 62*a* of the first conductive lead 58*a* is conductively attached to the generator 54 and the first end 66*a* of the second conductive lead 58*b* is conductively attached to the generator 54. The generator 54 generates desirable electric signals (TT signals) in the shape of waveforms or trains of pulses as an output. The second end 62*b* of the first conductive lead 58*a* is connected to a first pad 70*a* and the second end 66*b* of the second conductive lead 58*b* is connected to a second pad 70*b*, that is activated by the electric signals (e.g., wave forms). The first pad 70*a* and the second pad 70*b*, being activated by the electric signals, causes an electrical current to flow between the first pad 70*a* and the second pad 70*b*. The electrical current generates an electric field (i.e., TTField), having a frequency and an amplitude, to be generated between the first pad 70*a* and the second pad 70*b*.

The generator 54 generates an alternating voltage wave form at frequencies in the range from about 50 kHz to about 576 kHz (preferably from about 100 kHz to about 300 kHz) (i.e., the TTFields). The required voltages are such that an electric field intensity in tissue within the treatment area is in the range of about 0.1 V/cm to about 10V/cm. To achieve this field, the potential difference between the two conductors 18, (i.e., electrode element 124 described in detail below and shown in FIG. 4) in each of the first pad 70*a* or second pad 70*b* is determined by the relative impedances of the system components, i.e., a fraction of the electric field on each component is given by that component's impedance divided by a total circuit impedance.

In certain particular (but non-limiting) embodiments, the first pad 70*a* and the second pad 70*b* generate an alternating electric current and field within a target region of a patient. The target region typically comprises at least one tumor, and the generation of the alternating electric current and field selectively destroys or inhibits growth of the tumor. The alternating electric current and field may be generated at any frequency that selectively destroys or inhibits growth of the tumor. For example (but not by way of limitation), the alternating electric current and field may have a frequency of about 50 kHz, about 75 kHz, about 100 kHz, about 125 kHz, about 150 kHz, about 175 kHz, about 200 kHz, about 225 kHz, about 250 kHz, about 275 kHz, about 300 kHz, about 325 kHz, about 350 kHz, about 375 kHz, about 476 kHz, about 425 kHz, about 450 kHz, about 475 kHz, or about 576 kHz, as well as a range formed from any of the above values (i.e., a range of from about 50 kHz to about 576 kHz, a range of from about 100 kHz to about 150 kHz, a range of from about 150 kHz to about 300 kHz, etc.), and a range that combines two integers that fall between two of the above-referenced values (i.e., a range of from about 32 kHz to about 333 kHz, a range of from about 78 kHz to about 298 kHz, etc.).

In certain particular (but non-limiting) embodiments, the alternating electric current and field may be imposed at two or more different frequencies. When two or more frequencies are present, each frequency is selected from any of the above-referenced values, or a range formed from any of the above-referenced values, or a range that combines two integers that fall between two of the above-referenced values. As used herein, the alternating electric field may be referred to as the electric field or at the TTField.

In order to optimize the electric field (i.e., TTField) distribution, the first pad 70*a* and the second pad 70*b* (pair of pads) may be configured differently depending upon the application in which the pair of pads 70*a* and 70*b* are to be used. The pair of pads 70*a* and 70*b*, as described herein, are externally applied to a patient, that is, are generally applied to the patient's skin, in order to apply the electric current, and electric field (TTField) thereby generating current within the patient's tissue. Generally, the pair of pads 70*a* and 70*b* are placed on the patient's skin by a user such that the electric field is generated across patient tissue within a treatment area. TTFields that are applied externally can be of a local type or widely distributed type, for example, the treatment of skin tumors and treatment of lesions close to the skin surface.

In one embodiment, the user may be a medical professional, such as a doctor, nurse, therapist, or other person acting under the instruction of a doctor, nurse, or therapist. In another embodiment, the user may be the patient, that is, the patient may place the pad 70*a* and the pad 70*b* on their treatment area.

Optionally and according to another exemplary embodiment, the electronic apparatus 50 includes a control box 74 and a temperature sensor 78 coupled to the control box 74, which are included to control the amplitude of the electric field so as not to generate excessive heating in the treatment area.

When the control box 74 is included, the control box 74 controls the output of the generator 54 causing the output to remain constant at a value preset by the user. Alternatively, the control box 74 sets the output at the maximal value that does not cause excessive heating of the treatment area. In either of the above cases, the control box 74 may issue a warning, or the like, when a temperature of the treatment area (as sensed by temperature sensor 78) exceeds a preset limit. The temperature sensor 78 may be mechanically connected to and/or otherwise associated with the first pad 70*a* or the second pad 70*b* so as to sense the temperature of the treatment area at either one or both of the first pad 70*a* or the second pad 70*b*.

The conductive leads 58 are standard isolated conductors with a flexible metal shield, preferably grounded thereby preventing spread of any electric field generated by the conductive leads 58. the pad 70*a* and the pad 70*b* may have specific shapes and positioning so as to generate the TTField of a desired configuration, direction, and intensity at the treatment area and only there so as to focus the treatment.

The specifications of the electronic apparatus 50 as a whole and its individual components are largely influenced by the fact that at the frequency of the TTFields (50 kHz-576 kHz), living systems behave according to their "Ohmic", rather than their dielectric properties.

In one embodiment, to protect the patient from any current due to DC voltage or DC offset voltage passing through the patient, leads 58*a* and 58*b* may include a DC blocking component, such as blocking capacitor 82*a* and blocking capacitor 82*b*, to block DC current from passing to the pad 70*a* and the pad 70*b*. Without being bound by theory, the inventor now believes that the DC blocking component, while important for safety reasons, does not have to be located at the patient interface, i.e., within an electrode of the transducer array, or for that matter, be the non-conductive ceramic disk described above. The blocking capacitors 82*a* and 82*b* pass AC voltage to the pad 70*a* and the pad 70*b*, and also prevent any DC voltage or DC offset generated by the generator 54 or otherwise present in the electrical signal from passing to or through the patient. DC voltage, when applied to a patient, may have undesirable consequences, such as electrolysis or excessive heating of the first pad 70*a* and second pad 70*b* without the benefit of contributing to the power of the TTField. Thus, the blocking capacitors 82*a* and 82*b* can prevent electrolysis due to DC offsets or DC voltage. In one embodiment, the blocking capacitors 82*a* and 82*b* are non-polarized capacitors. In one embodiment, the blocking capacitors 82*a* and 82*b* have a capacitance of about 1 μF. In one embodiment, the blocking capacitor is a "Goldmax, 300 Series, Conformally Coated, X7R Dielectric, 25-250 VDC (Commercial Grade)" leaded non-polarized ceramic capacitor by KEMET Electronics Corporation (Fort Lauderdale, FL).

Electrically isolating the patient from the generator 54 may be very important, and so providing the blocking capacitors 82*a* and 82*b* outside of the generator 54 enhances the safety of the patient. The blocking capacitors 82*a* and 82*b* may be a component of the leads 58*a* and 58*b*, or an additional component at any position between the electrode element 124 of the first pad 70*a* and second pad 70*b* and the generator 54. For example, the blocking capacitors 82*a* and 82*b* may be intermediate the first end 60*a* of the lead 58*b* and the generator 54, or intermediate the second end 60*b* of the lead 58*b* and the second pad 70*b*. The inventor believes that the blocking capacitor 82*a* and 64*b* can be provided remote from the pad 70*a* and the pad 70*b* and still provide for safety of the patient. The blocking capacitors 82*a* and 82*b* can be located on a non-patient side of the electrode element 124.

In other embodiments, the blocking capacitors 82*a* and 82*b* may be components of the generator 54, that is, the blocking capacitors 82*a* and 82*b* may be integrated into the generator 54 such that prior to the electrical signal being passed into the leads 58*a* and 58*b*, the electrical signal passes through the blocking capacitors 82*a* and 82*b*. Alternatively, in a second embodiment, the blocking capacitors 82*a* and 82*b* may be a component of the first pad 70*a* and second pad 61*b*, the leads 58*a* and 58*b*, or an additional component at any position between conductive gel element 128 of the first pad 70*a* and second pad 70*b* and the generator 54. For example, the blocking capacitors 82*a* and 82*b* may be intermediate the first end 66*a* of the lead 58*b* and the generator 54, intermediate the second end 66*b* of the lead 58*b* and the second pad 70*b*, or an element of the second pad 70*b*.

One potential safety concern conventional systems were designed to minimize was the possibility of harmful electrolysis. In an electrolysis experiment wherein the blocking capacitors 82*a* and 82*b* are integrated into the generator 54 and no blocking capacitor is present in the first pad 70*a* or second pad 70*b*, little to no electrolysis was shown while using the first pad 70*a* and second pad 70*b* as described herein. In the electrolysis experiment, the first pad 70*a* and the second pad 70*b* were placed within a saline solution and connected to the generator 54. The generator 54 supplied a first electric signal of 2,194 mA and 21 V at 148 kHz to the first pad 70*a* and the second pad 70*b*. When the first electric signal was applied, no electrolysis was observed, that is, there was no apparent decomposition of the water in the saline solution into its constituent components, hydrogen and oxygen, as observed by a lack of gas formation on the first pad 70*a* or the second pad 70*b* as would be expected during electrolysis. Without being bound by theory, these preliminary experiments have led the inventor to consider the possibility that the risk of electrolysis occurring in a patient using such a system is minimal. Moreover, in the event a degree of electrolysis does occur, the side effects may be acceptable when weighed against the overall therapeutic efficacy of the system. It may be further possible to treat/manage such a side effect using alternative therapeutic regimes which specifically target electrolysis.

First Mode: Gel Compositions Comprising Bulk Electron Transport Agents

A first mode of the present disclosure includes a conductive gel composition for application to a patient's skin during treatment with a TTField-generating system. The conductive gel composition contains a semi-solid conductive gel in combination with at least one bulk electron transport agent (such as, but not limited to, carbon black, graphene, or graphite), which dramatically enhances the electrical and/or thermal conductivity of the semi-solid conductive gel.

Certain non-limiting embodiments of the present disclosure are directed to a composition that includes a semi-solid conductive gel for application to a patient's skin and for placement between the patient's skin and at least one insulated electrode that generates an alternating electric field within a patient (such as, but not limited to, an insulated electrode that generates an alternating electric field having a frequency in a range of from about 50 kHz to about 500 kHz). The composition further includes at least one bulk electron transport agent, which is disposed upon at least a portion of a surface of the semi-solid conductive gel and/or disposed within at least a portion of the semi-solid conductive gel.

Any carbon blacks known in the art or otherwise contemplated herein may be utilized in accordance with the present disclosure. One non-limiting example of a carbon black that may be utilized in accordance with the present disclosure is acetylene black.

Another particular (but non-limiting) example of a carbon black that can be utilized in accordance with the present disclosure is Ketjenblack (such as, but not limited to, Ketjenblack EC300J and Ketjenblack EC600JD); Ketjenblack possesses the same level of electro-conductivity at a much lower loading quantity when compared to conventional carbon blacks. As such, a desired level of volume resistivity is obtained at a much lower density of Ketjenblack when compared to the density required to obtain the same level of volume resistivity with conventional carbon blacks.

Another form of carbon black that may be utilized in accordance with the present disclosure is an amalgamation of carbon black with at least one substantially inert metal. Any substantially inert metals known in the art or otherwise contemplated herein can be utilized in accordance with the present disclosure, so long as the substantially inert metal will not substantially interact with salt present in the hydrogel. Non-limiting examples of substantially inert metals that can be utilized in accordance with the present disclosure include copper, gold, silver, alum, and combinations thereof.

Other examples of substances that can be utilized as bulk electron transport agents in accordance with the present disclosure include, but are not limited to, conductive polymers such as, but not limited to, Poly(3,4-ethylenedioxythiophene) (PEDOT) and polypyrrole; tetracyanoquinodimethane (TCNQ) salt; transition metal oxides or hydroxides, such as, but not limited to, manganese dioxide; sulphuric acid; ceramic substances such as, but not limited to, ceramic dust and MXenes; transition metal dichalcogenides; combinations of any of the above with one or more of any of the other bulk electron transport agent(s) described herein; or the like.

When the bulk electron transport agent is disposed within at least a portion of the semi-solid conductive gel, the bulk electron transport agent may be disposed within the conductive gel by any methods known in the art or otherwise contemplated herein. For example (but not by way of limitation), the bulk electron transport agent may be incorporated within the conductive gel and/or impregnated within the conductive gel. In certain non-limiting embodiments, the bulk electron transport agent is disposed within the conductive gel prior to curing/polymerization to form the semi-solid conductive gel. For example (but not by way of limitation), one or more bulk transport agents may be placed in a suspension that is mixed with another immiscible liquid containing the conductive gel prior to formation of the semi-solid gel.

When the bulk electron transport agent is disposed upon at least a portion of the surface of the semi-solid conductive gel, the bulk electron transport agent may be in the form of a powder or granules that are controlled or randomly positioned upon the surface; for example (but not by way of limitation), a carbon black, graphene, and/or graphite may simply be "sprinkled" or otherwise deposited upon the surface. Alternatively, the bulk electron transport agent may be provided in a layer or film that is positioned adjacent to the surface of the semi-solid conductive gel. For example (but not by way of limitation), the use of a carbon black layer/film as the bulk electron transport agent provides a more controlled and uniform disposal of the carbon black upon the entire surface of the semi-solid conductive gel that is in contact with the carbon black layer/film when compared to application of a powder or granules thereto. In addition, it will be understood that multiple layers/coatings of the same or different bulk electron transport agents may be present on and/or within the semi-solid conductive gel.

The composition may be loaded with any amount of bulk electron transport agent that allows the composition to function in accordance with the present disclosure. For example (but not by way of limitation), the bulk electron transport agent may be loaded in the composition at a concentration (wt) of about 0.01%, about 0.05%, about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 65%, about 70%, about 75%, about 80%, or higher, or a value that falls within a range of two of the above values (i.e., a range of from about 0.1% to about 40% (wt), a range of from about 1% to about 50% (wt), etc.).

The conductive gel may be in any form that allows the composition to function in accordance with the present disclosure. For example (but not by way of limitation), the conductive gel may be in the form of a hydrogel or a hydrocolloid.

In certain particular (but non-limiting) embodiments, the gel is sterile. In addition, in certain non-limiting embodiments, the gel will not substantially degrade upon exposure to sterilization conditions that include gamma rays or ethylene oxide gas.

The gel may be formed of any hydrophilic polymer that allows the gel to function in accordance with the present disclosure. For example (but not by way of limitation), the gel may be a polyacrylic acid gel, a povidone gel, or a cellulose gel. In addition, the gel may comprise at least one of chitosan, alginate, agarose, methylcellulose, hyaluronan, collagen, laminin, matrigel, fibronectin, vitronectin, poly-1-lysine, proteoglycans, fibrin glue, gels made by decellularization of engineered and/or natural tissues, as well as any combinations thereof. Further, the gel may comprise at least one of polyglycolic acid (PGA), polylactic acid (PLA), poly-caprolactone (PCL), polyvinyl alcohol (PVA), polyethylene glycol (PEG), methyl methacrylate, poly(methyl methacrylate) (PMMA), poly(2-hydroxyethyl methacrylate) (PolyHEMA), poly(glycerol sebacate), polyurethanes, poly (isopropylacrylamide), poly(N-isopropylacrylamide), or any combination thereof.

In certain non-limiting embodiments, the conductive gel comprises one or more of the following chemical and structural features/properties: a polymer chain length in a range of from about 1 nm to about 200 nm; a free salt present at a concentration in a range of from about 0.1 mM to about 1 M; a pH in a range of from about 6 to about 8; a volume resistivity of less than about 100 Ohm-in; a skin adhesion rate of at least about 100 g/inch; and a thickness in a range of from about 10 mil to about 50 mil.

In addition, given the prolonged exposure of the gel composition to the patient's skin, the gel should be optimized for use at body temperature (i.e., in a range of from about 34° C. to about 40° C.).

The polymers of the gel may be provided with any polymer chain length that allows the gel compositions to function as described herein. For example (but not by way of limitation), the polymer chain length may be about 1 nm, about 2 nm, about 3 nm, about 4 nm, about 5 nm, about 6 nm, about 7 nm, about 8 nm, about 9 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, about 150 nm, about 155 nm, about 160 nm, about 165 nm, about 170 nm, about 175 nm, about 180 nm, about 185 nm, about 190 nm, about 195 nm, about 200 nm, and above, as well as a range that combines any two of the above-referenced values (i.e., a range of from about 3 nm to about 175 nm, a range of from about 5 nm to about 150 nm, or a range of from about 10 nm to about 125 nm, a range of from about 15 nm to about 100 nm, etc.), and a range that combines two integers that fall between two of the above-referenced values (i.e., a range of from about 3 nm to about 157 nm, etc.).

In other non-limiting embodiments, the range of the polymer chain length is dependent upon the frequency(ies) of the alternating electric field. For example (but not by way of limitation), the range of the polymer chain length may be based upon a range of frequencies of the alternating electric field. Non-limiting examples include a range of from about 5 nm to about 50 nm when the alternating electric field has a frequency in a range of from about 50 kHz to about 150 kHz, a range of from about 50 nm to about 100 nm when the alternating electric field has a frequency in a range of from about 150 kHz to about 300 kHz, etc.

In certain non-limiting embodiments, the conductive gel has at least one of a decreased polymer chain length and an added free salt when compared to existing gel compositions; the decrease in polymer chain length and increase in free salt concentration further enhances the conductivity of the gel while reducing the occurrence of skin irritation caused by the gel. In a particular (but non-limiting) embodiment, the conductive gel comprises a free salt present via incorporation within the gel or as one layer of a multi-layered gel (i.e., a bilayered gel). The term "free salt" refers to salt molecules that are not incorporated as part of the polymerized chain structure but rather are floating substantially freely within the gel and thus are a source of free ions that conduct electricity and thus reduce impedance.

When free salt is present in the gel, the free salt may be any salt or other substance that serves as a source of free ions that are capable of floating substantially freely within the gel, wherein the free ions serve to conduct electricity and thus reduce impedance. In certain particular (but non-limiting) embodiments, the free salt present in the gel is a source of chloride ions, citrate ions, silver ions, iodide ions, etc., or any other ions that are known to be good conductors. Non-limiting examples of free salts that may be utilized in accordance with the present disclosure are salts that contain potassium (K), ammonium (NH4+), sodium (Na), nitrate, bicarbonate, and the like. Particular non-limiting examples of free salts that may be utilized in accordance with the present disclosure are NaCl, KCl, CaCl2), MgCl2, ZnCl2, iodine, silver iodide (AgI), silver dihydrogen citrate (SDC), sodium dihydrogen citrate, combinations thereof, and the like.

The free salt present in the gel may be provided with any concentration that allows the gel compositions to function as described herein. For example (but not by way of limitation), the free salt concentration may be at least about 0.1 mM, about 0.5 mM, about 1 mM, about 2 mM, about 3 mM, about 4 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 150 mM, about 200 mM, about 250 mM, about 300 mM, about 350 mM, about 400 mM, about 450 mM, about 500 mM, about 550 mM, about 600 mM, about 650 mM, about 700 mM, about 750 mM, about 800 mM, about 850 mM, about 900 mM, about 950 mM, about 1 M, or higher, as well as any range that combines any two of the above-referenced values (i.e., a range of from about 0.1 mM to about 100 mM, a range of from about 1 mM to about 50 mM, etc.), and a range that combines two integers that fall between two of the above-referenced values (i.e., a range of from about 12 mM to about 550 mM, etc.).

In other non-limiting embodiments, the free salt concentration is dependent upon the frequency(ies) of the alternating electric field. For example (but not by way of limitation), the range of the free salt concentration may be based upon a range of frequencies of the alternating electric field. Non-limiting examples include a range of from about 0.1 mM to about 50 mM when the alternating electric field has a frequency in a range of from about 50 kHz to about 150 kHz, a range of from about 50 mM to about 100 mM when the alternating electric field has a frequency in a range of from about 150 kHz to about 300 kHz, etc.

The gel may be provided with any pH that does not damage the skin of a patient or cause chemical irritation of the skin upon prolonged exposure to the gel. For example (but not by way of limitation), the gel may have a pH of about 6, about 6.5, about 7, about 7.5, about 8, as well as a range formed from any of the above values (i.e., a range of from about 6 to about 8, a range of from about 6.5 to about 7.5, etc.).

The gel may be provided with any level of volume resistivity that maximizes the conductiveness of the gel. For example (but not by way of limitation), the gel may have a volume resistivity of less than about 100 Ohm-in, less than about 95 Ohm-in, less than about 90 Ohm-in, less than about 85 Ohm-in, less than about 80 Ohm-in, less than about 75 Ohm-in, less than about 70 Ohm-in, less than about 65 Ohm-in, less than about 60 Ohm-in, less than about 55 Ohm-in, less than about 50 Ohm-in, less than about 45 Ohm-in, less than about 40 Ohm-in, less than about 35 Ohm-in, less than about 30 Ohm-in, less than about 25 Ohm-in, less than about 20 Ohm-in, less than about 15 Ohm-in, less than about 10 Ohm-in, or lower, as well as a range formed of any of the above values (i.e., a range of from about 10 Ohm-in to about 100 Ohm-in, etc.) and a range that combines two integers that fall between two of the above-referenced values (i.e., a range of from about 13 Ohm-in to about 96 Ohm-in, etc.).

The gel may be provided with any skin adhesion rate that allows the gel to function in accordance with the present disclosure. For example (but not by way of limitation), the skin adhesion rate of the gel may be at least about 100 g/inch, at least about 110 g/inch, at least about 120 g/inch, at least about 130 g/inch, at least about 140 g/inch, at least about 150 g/inch, at least about 160 g/inch, at least about 170 g/inch, at least about 180 g/inch, at least about 190 g/inch, at least about 200 g/inch, at least about 210 g/inch, at least about 220 g/inch, at least about 230 g/inch, at least about 240 g/inch, at least about 250 g/inch, at least about 260 g/inch, at least about 270 g/inch, at least about 280 g/inch, at least about 290 g/inch, at least about 300 g/inch, or higher, as well as a range of any of the above values (a range of from about 120 g/inch to about 300 g/inch, etc.), and a range that combines two integers that fall between two of the above-referenced values (i.e., a range of from about 115 g/inch to about 295 g/inch, etc.).

The gel may be provided with any thickness that allows the gel to function in accordance with the present disclosure. Non-limiting examples of thicknesses that may be utilized in accordance with the present disclosure include about 1 mil, about 5 mil, about 10 mil, about 15 mil, about 20 mil, about 25 mil, about 30 mil, about 35 mil, about 40 mil, about 45 mil, about 50 mil, about 55 mil, about 60 mil, about 65 mil, about 70 mil, about 75 mil, about 80 mil, about 85 mil, about 90 mil, about 95 mil, about 100 mil, or higher, as well as a range that combines any two of the above-referenced values (i.e., a range of from about 10 mil to about 50 mil, etc.), and a range that combines two integers that fall between two of the above-referenced values (i.e., a range of from about 12 mil to about 48 mil, etc.).

In certain particular (but non-limiting) embodiments, the gel has a shelf life of at least about six months. For example (but not by way of limitation), the gel has a shelf life of at least about 9 months or at least about 12 months.

In certain particular (but non-limiting) embodiments, the composition is a multi-layer structure that comprises: a scrim having a first and a second side with a gel tie layer attached to the first side of the scrim, and a gel skin layer attached to the second side of the scrim. The gel tie layer is designed for contact with the insulated electrode, while the gel skin layer is designed for contact with the patient's skin. The gel tie and gel skin layers are both formed of any of the conductive gels described or otherwise contemplated herein, and may be formed of the same or different conductive gels. The scrim may be formed of any material that allows the composition to function in accordance with the present disclosure; in particular, the material from which the scrim is formed is typically selected to optimize conductivity and minimize resistance of the composition. A non-limiting example of a material from which the scrim can be formed is spun nylon.

When this multi-layer structure is present, the bulk electron transport agent may be disposed within the gel tie layer and/or the gel skin layer. Alternatively (and/or in addition thereto), the bulk electron transport agent may be disposed (1) between the scrim and the gel tie layer, and/or (2) between the gel tie layer and the gel skin layer.

In addition, the composition may further include a removable top liner attached to the gel tie layer for protecting the gel tie layer until use, and/or a removable bottom liner attached to the gel skin layer for protecting the gel skin layer until use.

In certain particular (but non-limiting) embodiments, the alternating electric field is generated within a target region of the patient. The target region typically comprises at least one tumor, and the generation of the alternating electric field selectively destroys or inhibits growth of the tumor. The alternating electric field may be generated at any frequency that selectively destroys or inhibits growth of the tumor. For example (but not by way of limitation), the alternating electric field may have a frequency of about 50 kHz, about 75 kHz, about 100 kHz, about 125 kHz, about 150 kHz, about 175 kHz, about 200 kHz, about 225 kHz, about 250 kHz, about 275 kHz, about 300 kHz, about 325 kHz, about 350 kHz, about 375 kHz, about 400 kHz, about 425 kHz, about 450 kHz, about 475 kHz, or about 500 kHz, as well as a range formed from any of the above values (i.e., a range of from about 50 kHz to about 500 kHz, a range of from about 100 kHz to about 150 kHz, a range of from about 150 kHz to about 300 kHz, etc.), and a range that combines two integers that fall between two of the above-referenced values (i.e., a range of from about 32 kHz to about 333 kHz, a range of from about 78 kHz to about 298 kHz, etc.).

In certain particular (but non-limiting) embodiments, the alternating electric field may be imposed at two or more different frequencies. When two or more frequencies are present, each frequency is selected from any of the above-referenced values, or a range formed from any of the above-referenced values, or a range that combines two integers that fall between two of the above-referenced values.

Certain non-limiting embodiments of the present disclosure are directed to a kit that includes any of the conductive gel-containing compositions disclosed or otherwise contemplated herein.

In certain particular (but non-limiting) embodiments, the kit may further include at least one insulated electrode (such as, but not limited to, at least one insulated electrode utilized in a TTField-generating system). The at least one electrode comprises (for example, but not by way of limitation) at least one non-conducting layer, at least one conducting layer, and a high capacitance layer having an upper surface and a lower surface; in addition, at least one opening is disposed between the upper surface and the lower surface of the high capacitance layer. The conductive gel is for placement between the at least one electrode and a patient's skin and has a first surface and a second surface; the first surface of the conductive gel adheres to the lower surface of the high capacitance layer of the electrode, and the second surface of the conductive gel is for application to a patient's skin. The bulk electron transport agent is disposed within the conductive gel and/or disposed on at least a portion of the first surface of the conductive gel. The assembly may optionally further include a liner that is disposed on the second surface of the conductive gel to maintain the sterility thereof until use.

Any type of electrode(s) utilized in generating TTFields that is known in the art or otherwise contemplated herein may be utilized in accordance with the present disclosure. Examples of electrodes (and transducer arrays containing same) that function as part of a TTField system are known in the art and are described, for example but not by way of limitation, in U.S. Pat. Nos. 7,016,725; 7,089,054; 7,333,852; 7,565,205; 8,244,345; 8,715,203; 8,764,675; 10,188,851; and 10,441,776; and in US Patent Application Nos. US 2018/0160933; US 2019/0117956; US 2019/0307781; and US 2019/0308016. Therefore, no further description thereof is deemed necessary.

In certain particular (but non-limiting) embodiments, the at least one electrode may be further defined as at least one pair of transducer arrays that generates an alternating electric field having a frequency in a range of from about 50 kHz to about 500 kHz upon application to a patient's skin in combination with the conductive gel-containing composition (i.e., transducer arrays that function as part of a TTField-generating system). For example (but not by way of limitation), the kit may include at least about two pairs of transducer arrays, at least about four pairs of transducer arrays, at least about six pairs of transducer arrays, at least about eight pairs of transducer arrays, at least about ten pairs of transducer arrays, at least about 12 pairs of transducer arrays, at least about 14 pairs of transducer arrays, at least about 16 pairs of transducer arrays, at least about 18 pairs of transducer arrays, at least about 20 pairs of transducer arrays, at least about 22 pairs of transducer arrays, at least about 24 pairs of transducer arrays, at least about 26 pairs of transducer arrays, at least about 28 pairs of transducer arrays, at least about 30 pairs of transducer arrays, at least about 32 pairs of transducer arrays, at least about 34 pairs of transducer arrays, at least about 36 pairs of transducer arrays, at least about 38 pairs of transducer arrays, at least about 40 pairs of transducer arrays, at least about 42 pairs of transducer arrays, at least about 44 pairs of transducer arrays, at least about 46 pairs of transducer arrays, at least about 48 pairs of transducer arrays, at least about 50 pairs of transducer arrays, or more, as well as a range of pairs of transducer arrays that combines any two of the above-referenced values (i.e., a range of from about two pairs of transducer arrays to about 50 pairs of transducer arrays, a range of from about two pairs of transducer arrays to about 20 pairs of transducer arrays, etc.), and a range that combines two integers that fall between two of the above-referenced values (i.e., a range of from about one pair of transducer arrays to about 15 pairs of transducer arrays, etc.).

The composition may be present in the kit in any form that allows the kit to perform in accordance with the present disclosure. For example, but not by way of limitation, the composition may be provided in the form of one or more sheets or one or more rolls. In addition, the gel composition may be provided in a single, individual unit/amount, or multiple units/amounts of the composition may be provided within the kit.

When one or more electrodes (or transducer arrays containing same) are present in the kit, two or more components of the kit may be assembled for use thereof. For example (but not by way of limitation), the conductive gel-containing composition may be disposed upon the surface of the electrode(s) and this combination sealed together (either with or without a removable liner disposed upon the conductive gel) prior to placement of the combination within the kit. Alternatively, the conductive gel-containing composition may be disposed in the kit separate from the electrode(s).

In addition to the components described in detail herein above, the kits may further contain other component(s)/reagent(s) for performing any of the particular methods described or otherwise contemplated herein. For example (but not by way of limitation), the kits may additionally include: (i) components for preparing the skin prior to disposal of the gel composition and electrode(s) thereon (i.e., a razor, a cleansing composition or wipe/towel, etc.); (ii) components for removal of the gel/electrode(s); (iii) components for cleansing of the skin after removal of the gel/electrode(s); (iv) liquid hydrogel (as described in greater detail herein below); and/or (v) one or more dermatological therapeutic agents that may enhance the hydrogel/skin interface, enhance skin conductivity, enhance adhesiveness, and/or reduce or prevent the occurrence of dAEs (such as, but not limited to, an anti-microbial agent, an antibiotic, an anti-viral agent, an anti-fungal agent, an anti-inflammatory agent, an anesthetic, an emollient, a cleansing agent, an astringent, and combinations thereof, and the like).

The nature of these additional component(s)/reagent(s) will depend upon the particular treatment format and/or area/organ to be treated, and identification thereof is well within the skill of one of ordinary skill in the art; therefore, no further description thereof is deemed necessary. Also, the components/reagents present in the kits may each be in separate containers/compartments, or various components/reagents can be combined in one or more containers/compartments, depending on the sterility, cross-reactivity, and stability of the components/reagents.

In addition, the kit can further include a set of written instructions explaining how to use one or more components of the kit. A kit of this nature can be used in any of the methods described or otherwise contemplated herein.

In certain non-limiting embodiments, the kit has a shelf life of at least about six months, such as (but not limited to), at least about nine months, or at least about 12 months.

Certain non-limiting embodiments of the present disclosure are directed to an assembly that includes any of the conductive gel-containing compositions disclosed or otherwise contemplated herein disposed upon any of the insulated electrodes disclosed or otherwise contemplated herein.

In a particular (but non-limiting) embodiment, the assembly may further include a layer of liquid hydrogel disposed upon at least a portion of the second surface of the conductive gel (i.e., the surface that is applied to the patient's skin). The liquid hydrogel may be used when the bulk electron transport agent is disposed within the semi-solid conductive gel, or when the bulk electron transport agent is disposed on a surface of the conductive gel other than the second surface to which the liquid hydrogel may be applied.

The liquid hydrogel may have a similar formulation and/or similar structural characteristics to those described above for the semi-solid conductive gel (with the exception of cross-linking of the polymer), or the liquid hydrogel may have a different formulation and/or different structural characteristics from the semi-solid conductive gel. The only requirements for the liquid hydrogel are that the liquid hydrogel should be: (1) conductive; (2) hypoallergenic; and (3) have an osmolality that is substantially similar to the semi-solid conductive gel (so that there is no substantial shrinking or swelling of the semi-solid conductive gel in response to exposure to the liquid hydrogel). For example (but not by way of limitation), the osmolality of the liquid hydrogel may be substantially identical to an osmolality of the semi-solid conductive gel or may vary therefrom by less than about 25%, or less than about 20%, or less than about 15%, or less than about 14%, or less than about 13%, or less than about 12%, or less than about 11%, or less than about 10%, or less than about 9%, or less than about 8%, or less than about 7%, or less than about 6%, or less than about 5%, or less than about 4%, or less than about 3%, or less than about 2%, or less than about 1%.

One non-limiting example of a commercially available liquid hydrogel that may be utilized in accordance with the present disclosure is CARRASYN® V hydrogel wound dressing (Medline Industries, Inc., Northfield, IL). This product contains aloe barbadensis leaf juice, carbomer, citric acid, disodium EDTA, glutamic acid, imidazolidinyl urea, methylparaben, panthenol, potassium sorbate, PVP, sodium benzoate, sodium chloride, sodium metabisusulfite, triethanolamine, and water. However, this hydrogel formulation is provided for illustrative purposes only. Any other hydrogel formulations that can function in the assemblies/transducer arrays as described herein also falls within the scope of the present disclosure.

In certain non-limiting embodiments, the semi-solid conductive gel may be provided with one or more types of modifications that extend inwardly or outwardly from a surface thereof and that affect the thickness of certain portions of the semi-solid conductive gel; in addition, bulk electron transport agents, air, liquid hydrogel, and/or other agents (such as, but not limited to, dermatological therapeutic agents) may be disposed in at least a portion of the modifications. Non-limiting examples of modifications that may be utilized in accordance with the present disclosure include openings, perforations, recesses, indentations, and channels; wells or voids formed between protrusions; and one or more compartments extending from a surface thereof. These modifications serve at least two purposes. First, they provide a reservoir in which bulk electron transport agent(s), liquid hydrogel, and/or dermatological therapeutic agent(s) may be disposed. Second, the modifications may alternatively be filled with air so as to allow for increased air flow between a patient's skin and the conductive gel and thereby reducing, if not eliminating, dAEs such as (but not limited to) macerations, lesions/ulcers, and dermatitis. In addition, the presence of air in one or more modifications allows for a decrease in operating temperature when a TTField is applied to the assembly containing the modified semi-solid conductive gel. In addition, the presence of one or more modifications in the hydrogel can actually increase adhesion of the hydrogel to the patient's skin.

Certain non-limiting embodiments of the present disclosure are directed to a method that includes: (1) applying any of the conductive gel-containing compositions disclosed or otherwise contemplated herein to a skin of a patient; (2) applying at least one electrode (or at least one transducer array containing same) to the gel-containing composition disposed upon the patient's skin; and (3) generating an alternating electric field (such as, but not limited to, an alternating electric field having a frequency in a range of from about 50 kHz to about 500 kHz for a period of time).

In certain particular (but non-limiting) embodiments, step (2) includes the application of at least two insulated electrodes to the gel-containing composition disposed upon the patient's skin.

In certain particular (but non-limiting) embodiments, the alternating electric field is generated within a target region of the patient. The target region typically comprises at least one tumor, and the generation of the alternating electric field selectively destroys or inhibits growth of the tumor. The alternating electric field may be generated at any frequency that selectively destroys or inhibits growth of the tumor. For example (but not by way of limitation), the alternating electric field may have a frequency of about 50 kHz, about 75 kHz, about 100 kHz, about 125 kHz, about 150 kHz, about 175 kHz, about 200 kHz, about 225 kHz, about 250 kHz, about 275 kHz, about 300 kHz, about 325 kHz, about 350 kHz, about 375 kHz, about 400 kHz, about 425 kHz, about 450 kHz, about 475 kHz, or about 500 kHz, as well as a range formed from any of the above values (i.e., a range of from about 100 kHz to about 300 kHz, a range of from about 100 kHz to about 150 kHz, a range of from about 150 kHz to about 300 kHz, etc.), and a range that combines two integers that fall between two of the above-referenced values (i.e., a range of from about 32 kHz to about 333 kHz, a range of from about 78 kHz to about 298 kHz, etc.).

In certain particular (but non-limiting) embodiments, the alternating electric field may be generated at two or more different frequencies. When two or more frequencies are present, each frequency is selected from any of the above-referenced values, or a range formed from any of the above-referenced values, or a range that combines two integers that fall between two of the above-referenced values.

In certain particular (but non-limiting) embodiments, the composition and the at least one insulated electrode are maintained upon the patient's skin for at least about three days.

In certain particular (but non-limiting) embodiments, the method includes the steps of: (4) removing the at least one insulated electrode and the gel-containing composition from the patient's skin; (5) preparing the patient's skin for another treatment (such as, but not limited to, cleansing of the skin and shaving of the skin, if necessary); and (6) repeating steps (1)-(3). In addition, this cycle of steps (1)-(6) can be repeated as many times as necessary.

When steps (1)-(3) are repeated, the gel-containing composition and at least one insulated electrode may be placed in different positions than their original placement; relocation of the electrode(s) in this manner treatment functions to minimize any dAEs that may occur.

EXAMPLE

An Example is provided hereinbelow. However, the present disclosure is to be understood to not be limited in its application to the specific experimentation, results, and laboratory procedures disclosed herein after. Rather, the Example is simply provided as one of various embodiments and are meant to be exemplary, not exhaustive.

In this Example, Ketjenblack EC600JD was applied to the surface of a semi-solid conductive hydrogel (AG625 Sensing Gel from Axelgaard Manufacturing Co Ltd, Fallbrook, CA), and this assembly was subsequently applied to an electrode of a TTField generating system; then, the volume resistivity and capacitance of the assembly were examined, as shown in Table 1. As can be seen, the addition of Ketjenblack EC600JD greatly increased the conductivity and capacitance of the hydrogel.

TABLE 1

| | Volume Resistivity | Capacitance |
|---|---|---|
| Hydrogel Alone | 180 ohms | 5,500 nF |
| Hydrogel plus Ketjenblack EC600JD | 14 ohms | 7,500 nF |

Therefore, the addition of one or more bulk electron transport agents to a semi-solid polymerized hydrogel served to reduce impedance and increase capacitance of the system.

The following is a number list of non-limiting illustrative embodiments of the inventive concept of the first mode disclosed herein:

233. A composition, comprising:

a semi-solid conductive gel for application to a patient's skin and for placement between the patient's skin and at least one insulated electrode; and at least one bulk electron transport agent disposed upon at least a portion of a surface of the semi-solid conductive gel and/or disposed within at least a portion of the semi-solid conductive gel, wherein the bulk electron transport agent is selected from the group consisting of an ionic compound, a metal, a non-metal, and combinations thereof.

234. The composition of illustrative embodiment 233, wherein the bulk electron transport agent is disposed within the conductive gel prior to curing to form the semi-solid conductive gel.

235. The composition of illustrative embodiment 233 or illustrative embodiment 234, wherein the bulk electron transport agent is disposed upon at least a portion of the surface of the semi-solid conductive gel.

236. The composition of any one of illustrative embodiments 233 to illustrative embodiment 235, wherein the bulk electron transport agent comprises an amorphous carbon and/or a crystalline carbon.

237. The composition of illustrative embodiment 236, wherein the bulk electron transport agent comprises at least one of carbon black, graphene, and graphite.

238. The composition of illustrative embodiment 237, wherein the carbon black is further defined as being a carbon black film that is disposed upon at least a portion of the surface of the semi-solid conductive gel.

239. The composition of illustrative embodiment 237, wherein the carbon black is in the form of an amalgamation with at least one substantially inert metal.

240. The composition of illustrative embodiment 239, wherein the substantially inert metal is selected from the group consisting of copper, gold, silver, alum, and combinations thereof.

241. The composition of any one of illustrative embodiments 237 to 240, wherein the carbon black is Ketjenblack.

242. The composition of any one of illustrative embodiments 233 to 241, wherein the bulk electron transport agent is selected from the group consisting of a conductive polymer; tetracyanoquinodimethane (TCNQ) salt; a transition metal oxide or hydroxide; sulphuric acid; a ceramic substance; transition metal dichalcogenides; combinations thereof.

243. The composition of any one of illustrative embodiments 233 to 242, wherein the bulk electron transport agent is loaded in the composition at a concentration in a range of from about 1% to about 50% (wt).

244. The composition of any one of illustrative embodiments 233 to 243, wherein the gel is a hydrogel.

245. The composition of any one of illustrative embodiments 233 to 244, wherein the gel is sterile.

246. The composition of any one of illustrative embodiments 233 to 245, wherein the conductive gel comprises at least one of:

a polymer chain length in a range of from about 1 nm to about 200 nm;

a pH in a range of from about 6 to about 8;

a volume resistivity of less than about 100 Ohm-in;

a skin adhesion rate of at least about 100 g/inch;

a free salt present at a concentration in a range of from about 0.1 mM to about 1 M; and a thickness in a range of from about 10 mil to about 50 mil.

247. The composition of any one of illustrative embodiments 233 to 246, wherein the gel has a shelf life of at least about six months.

248. The composition of any one of illustrative embodiments 233 to 247, further defined as being a multi-layer structure that comprises:

a scrim having a first and a second side;

a gel tie layer attached to the first side of the scrim, wherein the gel tie layer is designed for contact with the at least one insulated electrode; and a gel skin layer attached to the second side of the scrim, wherein the gel skin layer is designed for contact with the patient's skin.

249. The composition of illustrative embodiment 248, wherein the bulk electron transport agent is disposed within at least one of the gel tie layer and the gel skin layer.

250. The composition of illustrative embodiment 248, wherein the bulk electron transport agent is disposed between the scrim and the gel tie layer.

251. The composition of illustrative embodiment 248, wherein the bulk electron transport agent is disposed between the scrim and the gel skin layer.

252. A kit, comprising:

the composition of any one of illustrative embodiments 233-251.

253. The kit of illustrative embodiment 252, further comprising at least one insulated electrode that generates an alternating electric field upon application to a patient's skin in combination with the composition.

254. A method, comprising the steps of:

(1) applying the composition of any one of illustrative embodiments 1-19 to a skin of a patient;

(2) applying at least one insulated electrode to the composition disposed upon the patient's skin; and (3) generating an alternating electric field in a target region of the patient.

255. The method of illustrative embodiment 254, wherein the alternating electric field has a frequency in a range of from about 50 kHz to about 500 kHz for a period of time.

256. The method of illustrative embodiment 254 or 255, wherein the composition and the at least one insulated electrode are maintained upon the patient's skin for at least about three days.

257. The method of any one of illustrative embodiments 254-256, further comprising the steps of:

(4) removing the at least one insulated electrode and the gel-containing composition from the patient's skin;

(5) preparing the patient's skin for another treatment; and (6) repeating steps (1)-(3).

258. The method of any one of illustrative embodiments 254 to 257, wherein the target region comprises at least one tumor, and wherein the generation of the alternating electric field selectively destroys or inhibits growth of the tumor.

Second Mode: Flexible Conductive Pad

A second mode of the present disclosure includes a conductive pad. The conductive pad has a topcoat layer, an electrode element and a conductive gel element. The electrode element is connected to the topcoat layer, and configured to receive an electrical signal from a generator producing an electric signal as a TTField. The conductive gel element is directly connected to the electrode element so as to receive an electrical current from the electrode element. The conductive gel element is configured to be in contact with a patient's skin. The electrode element and the conductive gel element can be constructed of a plurality of flexible films bonded together so as to provide the conductive pad with sufficient flexibility to conform to a patient's body.

Figure 3:
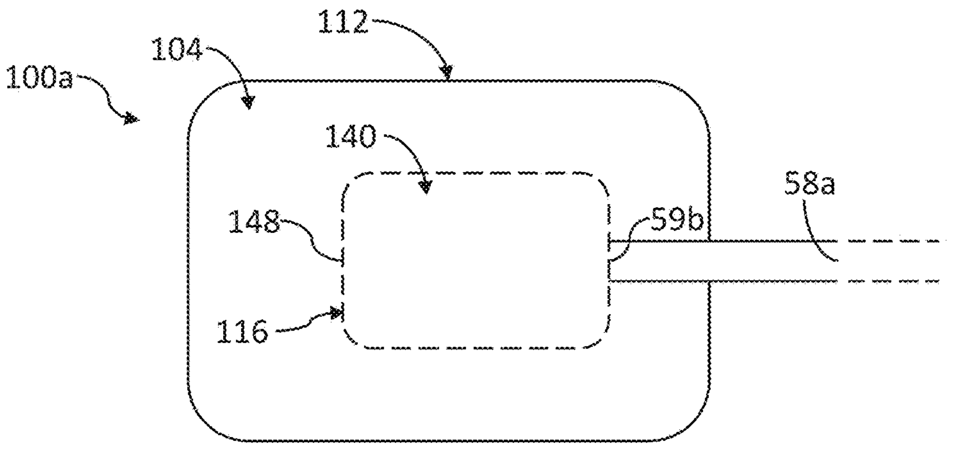
FIG. 3 is a top plan view of a first conductive pad constructed in accordance with the present disclosure.

Referring now to FIG. 3, shown therein is a top plan view of an exemplary embodiment of a first conductive pad 100*a*. The first conductive pad 100*a* is an exemplary embodiment of the pad 70*a* and the pad 70*b*. For purposes of brevity, the construction of the first conductive pad 100*a* will be described herein. The first conductive pad 100*a* may be provided with a top 104, a bottom 108 (shown in FIG. 4), an outer peripheral edge 112, and a conductive region 116 bounded by the outer peripheral edge 112. As shown, the first conductive pad 100*a* is connected to the second end 62*b* of the conductive lead 58*a*. The first conductive pad 100*a* is constructed so as to have sufficient flexibility so as to be able to conform to a portion of the patient, such as a portion of the patient's head, the patient's knee, or the like. The first conductive pad 100*a* may also be constructed so that the conductive region 116 is continuous, and extends to the outer peripheral edge 112. In the example shown, the first conductive pad 100*a* is provided with a rectangular shape. However, it should be understood that the first conductive pad 100*a* can be provided with any type of shape such as a polygon, circle, or fanciful shape. Further, the first conductive pad 100*a* may be constructed so as to be cut and/or shaped at a point of use so as to be custom fitted for a particular part of a particular patient.

Figure 4:
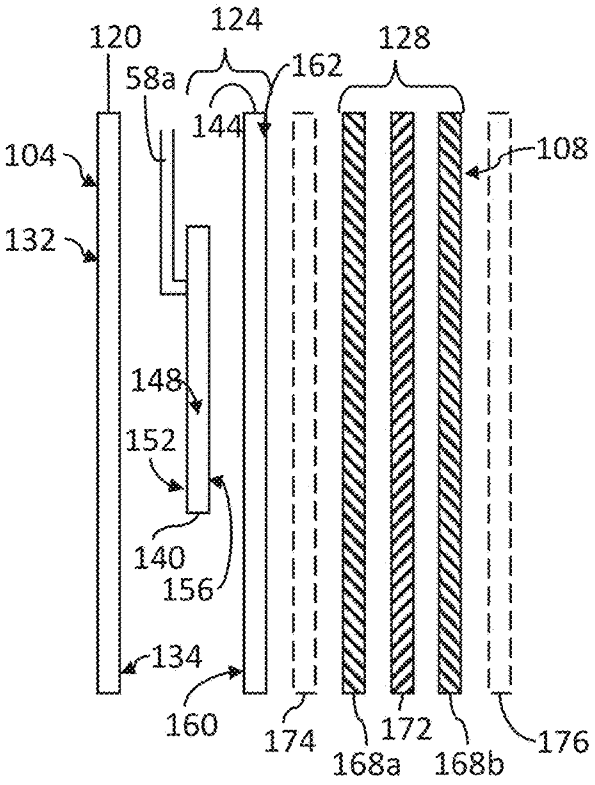
FIG. 4 is an exploded side view of an exemplary embodiment of the first conductive pad depicted in FIG. 3.
Figure 5:
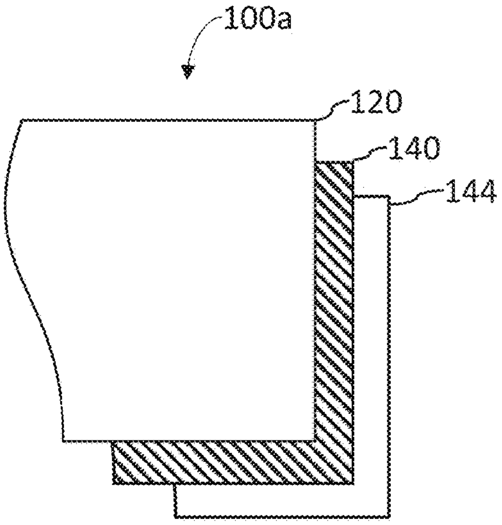
FIG. 5 is an exploded top perspective view of the first conductive pad depicted in FIG. 3.

Referring now to FIG. 3 in combination with FIG. 4 and FIG. 5, shown in FIG. 4 is an exploded side view of one embodiment of the first conductive pad 100*a* constructed in accordance with the present disclosure. FIG. 5 is a partial exploded top plan view of the first conductive pad 100*a*. The first conductive pad 100*a* may be provided with a durable topcoat layer 120, an electrode element 124, and a conductive gel element 128. The electrode element 124 is positioned between the durable topcoat layer 120 and the conductive gel element 128. The durable topcoat layer 120, the electrode element 124, and a conductive gel element 128 may be bonded together to form a composite structure that has the sufficiently flexible qualities discussed above. In some embodiments, the electrode element 124 is electrically coupled to the conductive gel element 128 so as to supply an electrical current from the electrode element 124 to the conductive gel element 128. In this embodiment, the first conductive pad 100*a* does not include a dielectric layer electrically isolating the electrode element 124 from the conductive gel element 128.

In one embodiment, the durable topcoat layer 120 is a non-woven, non-conductive fabric. The durable topcoat layer 120 provides a safe handling surface for the first conductive pad 100*a* to electrically isolate the electrode element 124 from the top 104 of the first conductive pad 100*a*. In some embodiments, the durable topcoat layer 120 is colored to match or approximate skin color of the patient. The durable topcoat layer 120 includes a first surface 132 forming the top 104 of the first conductive pad 100*a* and a second surface 134 in contact with and bonded to an electrode layer 140 and the conductive support layer 144.

In one embodiment, the durable topcoat layer 120 may be "breathable", that is, the durable topcoat layer 120 includes one or more perforation or the like extending from the first surface to the second surface to enable air-flow to other layers. The one or more perforation may have the same or different dimension(s) as one or more other perforation, as well as the same or different shape as one or more other perforation.

The electrode element 124 may include an electrode layer 140, and a conductive support layer 144 connected to the electrode layer 140. The electrode layer 140 overlaps the conductive support layer 144. The electrode layer 140 includes an outer peripheral electrode edge 148. The conductive support layer 144 may extend beyond the outer peripheral electrode edge 148 of the electrode layer 140. The first conductive pad 100*a* may also be referred to as an electrode, such as the first electrode 18*a* or the second electrode 18*b*, or electrode pad.

Figures 6, 7:
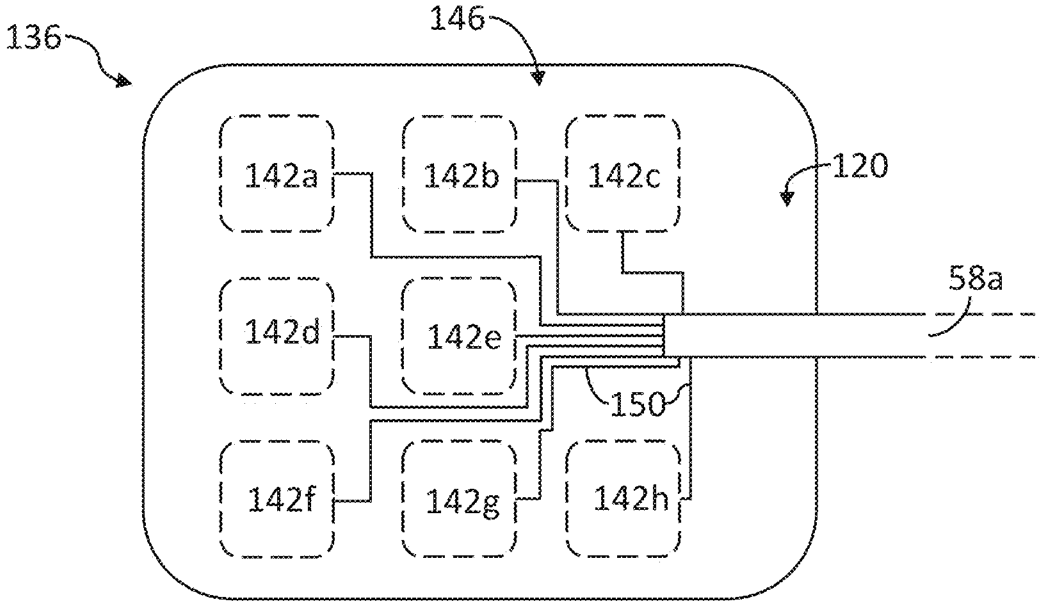
FIG. 6 is a top plan view of another embodiment of a conductive pad constructed in accordance with the present disclosure.
FIG. 7 is table showing experimental test results comparing a transducer array from prior art and the conductive pad of the present disclosure.

In one embodiment, the electrode element 124 has a surface area corresponding to an area of the conductive region 116 and the durable topcoat layer 120 has a surface area. In one embodiment, the area of the conductive region 116 is at least about 50% of the size of the surface area of the durable topcoat layer 120. In another embodiment, the area of the conductive region 116 is at least about 90% of the surface area of the durable topcoat layer 120. In yet another embodiment, the area of the conductive region 116 is about 100% the size of the surface area of the durable topcoat layer 120. In other embodiments, the area of the conductive region 116 is between 50% and 90% of the surface area of the durable topcoat layer 120 and/or the area of the conductive region 116 is between about 90% and about 100% of the surface area of the durable topcoat layer 120. In one embodiment, the increased area of the conductive region 116 relative to the durable topcoat layer 120 in combination with the flexibility of the first conductive pad 100*a* to conform and/or contour to that patient provides an increase in contact area and electrical conductivity between the conductive region 116 and the patient, thus resulting in a lower resistance and enabling the generator 54 to provide over four-times (4) more power into the patient without reaching a comfortability threshold as shown in FIG. 7 and described in more detail below.

In some embodiments, the area of the conductive region 116 is between 30 square inches and 75 square inches). The first conductive pad 100*a* has the advantage of having more surface area through which TTFs can be delivered to the patient. In contrast, the prior are non-conductive arrays transmit TTFs through small, circular ceramics—because TTFs are focused on these points, they are prone to overheating. Overheating can be managed by adding more ceramics disks, but the conventional transducer arrays are limited to the available exposed skin on a person that is able to receive a ceramic disk as well as trying to maintain patient comfort.

The electrode layer 140 may be selected from any conductive material having desirable properties such as, but not limited to, high conductivity, strong biocompatibility, and low reactivity with other layers or components of the first conductive pad 100*a*. In one embodiment, the electrode layer 140 is selected from one or more of the following: silver, tin, aluminum, titanium, platinum, an alloy thereof, and/or some combination thereof. The electrode layer 140 includes a first surface 152 in contact with the second surface 134 of the durable topcoat layer 120 and a second surface 156 in contact with the conductive support layer 144.

In one embodiment, the electrode layer 140 may be bonded to the conductive support layer 144. The conductive support layer 144 may include a first surface 160 attached to or otherwise coupled to the second surface 156 of the electrode layer 140 and a second surface 162 in direct contact with the conductive gel element 128. In some embodiments, an entirety of the second surface 162 is in direct contact with the conductive gel element 128. The conductive support layer 144 may be formed of a conductive carbon film configured to support the electrode layer 140 while also conductively coupling the electrode layer 140 to the conductive gel element 128. In one embodiment, the conductive support layer 144 may be electroplated, or otherwise bonded, to the electrode layer 140.

In one embodiment, a thickness of the electrode layer 140, or alternatively the thickness of the electrode layer 140 and the conductive support layer 144, may be determined based on the current and the frequency of the electric signal used to generate the TTField. The thickness may also be set based on other desirable properties such as heat dissipation and/or flexibility requirements of the first conductive pad 100*a*, for example. For example, if the thickness is too thin, the patient may experience hot spots, that is, the patient may experience portions of the first conductive pad 100*a* heating more rapidly than other portions of the first conductive pad 100*a*, which may be due, at least in part, to the thickness slowing thermal conductivity within the electrode layer 140, thus causing an increase in temperature differentials across the first conductive pad 100*a*. In one embodiment, the thickness is between 25 mil and 75 mil.

In one embodiment, the conductive gel element 128 includes one or more conductive gel layer 168 having a bulk electron transport agent providing a source of free ions therein to enable electrical conductivity. In one embodiment, the one or more conductive gel layer 168 is formed primarily of a conductive gel or a semi-solid conductive gel. In the embodiment depicted in FIG. 4, the conductive gel element 128 includes two conductive gel layers 168*a* and 168*b* bonded to a support layer 172. When present, the source of free ions in the gel may be any salt or other substance that serves as a source of free ions that are capable of floating substantially freely within the gel, wherein the free ions serve to conduct electricity and thus reduce impedance. In one embodiment, the conductive gel layers 168*a* and 168*b* include a polymeric hydrogel. In one embodiment, the conductive gel layers 168*a* and 168*b* have adhesive properties, thus the first conductive pad 100*a* when placed at a particular location on the patient has a tendency to remain at that particular location. The conductive gel layer 168*a* may be constructed of a same or different material as the conductive gel layer 168*b*. The support layer 172 may be constructed of a woven or nonwoven material such as a material known as Reemay (spun nylon). The support layer 172 can either be constructed of a conductive material, or the support layer 172 may be constructed of a nonconductive material but with a structure so as to permit the conductive gel layers 168*a* and 168*b* to become embedded into the structure and facilitate conductivity across the support layer 172.

The bulk electron transport agent(s) may be any substance that is capable of enhancing the electrical and/or thermal conductivity of the conductive gel. In certain non-limiting embodiments, the bulk electron transport agent(s) includes one or more ionic compounds, one or more metals, or one or more non-metals, as well as any combinations thereof. In certain non-limiting embodiments, the bulk electron transport agent comprises an amorphous carbon and/or a crystalline carbon. Particular (but non-limiting) examples of bulk electron transport agents that may be utilized in accordance with the present disclosure include carbon black, graphene, and graphite.

In one embodiment, the conductive gel element 128 and/or the one or more conductive gel layer 168 are formed primarily of a conductive gel or semi-solid conductive gel such as described below. The conductive gel element 128 may be in any form that allows the first conductive pad 100*a* to function in accordance with the present disclosure. The exact thickness of the conductive gel element 128 is not important so long as the conductive gel element 128 is of sufficient thickness that the conductive gel element 128 does not dry out during the treatment. Preferably, the conductive gel element 128 has high conductivity, is tacky, and is biocompatible for extended periods of time. One suitable gel is AG603 Hydrogel, which is available from AmGel Technologies, 1667 S. Mission Road, Fallbrook, Calif. 92028-4115, USA. The conductive gel element 128 taught therein may be used with modified hydrogels (which includes not only perforations but also recesses, protrusions, etc.) as disclosed in detail in U.S. Patent Application No. 63/020,636 entitled "Conductive Gel Compositions Comprising Bulk Electron Transport Agents and Methods of Production and Use Thereof", which is hereby incorporated in its entirety.

The conductive gel may be in any form that allows the composition to function in accordance with the present disclosure. For example (but not by way of limitation), the conductive gel may be in the form of a hydrogel or a hydrocolloid.

In certain particular (but non-limiting) embodiments, the conductive gel is sterile. In addition, in certain non-limiting embodiments, the conductive gel will not substantially degrade upon exposure to sterilization conditions that include gamma rays or ethylene oxide gas.

The conductive gel may be formed of any hydrophilic polymer that allows the conductive gel to function in accordance with the present disclosure. For example (but not by way of limitation), the conductive gel may be a polyacrylic acid gel, a povidone gel, or a cellulose gel. In addition, the conductive gel may comprise at least one of chitosan, alginate, agarose, methylcellulose, hyaluronan, collagen, laminin, matrigel, fibronectin, vitronectin, poly-1-lysine, proteoglycans, fibrin glue, gels made by decellularization of engineered and/or natural tissues, as well as any combinations thereof. Further, the conductive gel may comprise at least one of polyglycolic acid (PGA), polylactic acid (PLA), poly-caprolactone (PCL), polyvinyl alcohol (PVA), polyethylene glycol (PEG), methyl methacrylate, poly(methyl methacrylate) (PMMA), poly(2-hydroxyethyl methacrylate) (PolyHEMA), poly(glycerol sebacate), polyurethanes, poly (isopropylacrylamide), poly(N-isopropylacrylamide), or any combination thereof.

In certain non-limiting embodiments, the conductive gel comprises one or more of the following chemical and structural features/properties: a polymer chain length in a range of from about 1 nm to about 200 nm; a free salt present at a concentration in a range of from about 0.1 mM to about 1 M; a pH in a range of from about 6 to about 8; a volume resistivity of less than about 100 Ohm-in; a skin adhesion rate of at least about 100 g/inch; and a thickness in a range of from about 10 mil to about 50 mil.

In addition, given the prolonged exposure of the conductive gel composition to the patient's skin, the conductive gel should be optimized for use at body temperature (i.e., in a range of from about 34° C. to about 40° C.).

The polymer(s) of the conductive gel may be provided with any polymer chain length that allows the conductive gel composition(s) to function as described herein. For example (but not by way of limitation), the polymer chain length may be about 1 nm, about 2 nm, about 3 nm, about 4 nm, about 5 nm, about 6 nm, about 7 nm, about 8 nm, about 9 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, about 150 nm, about 155 nm, about 160 nm, about 165 nm, about 170 nm, about 175 nm, about 180 nm, about 185 nm, about 190 nm, about 195 nm, about 200 nm, and above, as well as a range that combines any two of the above-referenced values (i.e., a range of from about 3 nm to about 175 nm, a range of from about 5 nm to about 150 nm, or a range of from about 10 nm to about 125 nm, a range of from about 15 nm to about 100 nm, etc.), and a range that combines two integers that fall between two of the above-referenced values (i.e., a range of from about 3 nm to about 157 nm, etc.).

In other non-limiting embodiments, the range of the polymer chain length is dependent upon the frequency(ies) of the alternating electric field. For example (but not by way of limitation), the range of the polymer chain length may be based upon a range of frequencies of the alternating electric field. Non-limiting examples include a range of from about 5 nm to about 50 nm when the alternating electric field has a frequency in a range of from about 50 kHz to about 150 kHz, a range of from about 50 nm to about 100 nm when the alternating electric field has a frequency in a range of from about 150 kHz to about 300 kHz, etc.

In certain non-limiting embodiments, the conductive gel has at least one of a decreased polymer chain length and an added free salt when compared to existing gel compositions; the decrease in polymer chain length and increase in free salt concentration further enhances the conductivity of the conductive gel while reducing the occurrence of skin irritation caused by the conductive gel. In a particular (but non-limiting) embodiment, the conductive gel comprises a free salt present via incorporation within the conductive gel or as one layer of a multi-layered gel (i.e., a bilayered gel). The term "free salt" refers to salt molecules that are not incorporated as part of the polymerized chain structure but rather are floating substantially freely within the conductive gel and thus are a source of free ions that conduct electricity and thus reduce impedance.

When free salt is present in the conductive gel, the free salt may be any salt or other substance that serves as a source of free ions that are capable of floating substantially freely within the conductive gel, wherein the free ions serve to conduct electricity and thus reduce impedance. In certain particular (but non-limiting) embodiments, the free salt present in the conductive gel is a source of chloride ions, citrate ions, silver ions, iodide ions, etc., or any other ions that are known to be good conductors. Non-limiting examples of free salts that may be utilized in accordance with the present disclosure are salts that contain potassium (K), ammonium ($NH_4^+$), sodium (Na), nitrate, bicarbonate, and the like. Particular non-limiting examples of free salts that may be utilized in accordance with the present disclosure are NaCl, KCl, $CaCl_2$), $MgCl_2$, $ZnCl_2$, iodine, silver iodide (AgI), silver dihydrogen citrate (SDC), sodium dihydrogen citrate, combinations thereof, and the like.

The free salt present in the gel may be provided with any concentration that allows the conductive gel compositions to function as described herein. For example (but not by way of limitation), the free salt concentration may be at least about 0.1 mM, about 0.5 mM, about 1 mM, about 2 mM, about 3 mM, about 4 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 150 mM, about 200 mM, about 250 mM, about 300 mM, about 350 mM, about 476 mM, about 450 mM, about 576 mM, about 550 mM, about 676 mM, about 650 mM, about 776 mM, about 750 mM, about 876 mM, about 850 mM, about 976 mM, about 950 mM, about 1 M, or higher, as well as any range that combines any two of the above-referenced values (i.e., a range of from about 0.1 mM to about 100 mM, a range of from about 1 mM to about 50 mM, etc.), and a range that combines two integers that fall between two of the above-referenced values (i.e., a range of from about 12 mM to about 550 mM, etc.).

In other non-limiting embodiments, the free salt concentration is dependent upon the frequency(ies) of the alternating electric field. For example (but not by way of limitation), the range of the free salt concentration may be based upon a range of frequencies of the alternating electric field. Non-limiting examples include a range of from about 0.1 mM to about 50 mM when the alternating electric field has a frequency in a range of from about 50 kHz to about 150 kHz, a range of from about 50 mM to about 100 mM when the alternating electric field has a frequency in a range of from about 150 kHz to about 300 kHz, etc.

The conductive gel may be provided with any pH that does not damage the skin of a patient or cause chemical irritation of the skin upon prolonged exposure to the conductive gel. For example (but not by way of limitation), the conductive gel may have a pH of about 6, about 6.5, about 7, about 7.5, about 8, as well as a range formed from any of the above values (i.e., a range of from about 6 to about 8, a range of from about 6.5 to about 7.5, etc.).

The conductive gel may be provided with any level of volume resistivity that maximizes the conductivity of the gel. For example (but not by way of limitation), the conductive gel may have a volume resistivity of less than about 100 Ohm-in, less than about 95 Ohm-in, less than about 90 Ohm-in, less than about 85 Ohm-in, less than about 80 Ohm-in, less than about 75 Ohm-in, less than about 70 Ohm-in, less than about 65 Ohm-in, less than about 60 Ohm-in, less than about 55 Ohm-in, less than about 50 Ohm-in, less than about 45 Ohm-in, less than about 40 Ohm-in, less than about 35 Ohm-in, less than about 30 Ohm-in, less than about 25 Ohm-in, less than about 20 Ohm-in, less than about 15 Ohm-in, less than about 10 Ohm-in, or lower, as well as a range formed of any of the above values (i.e., a range of from about 10 Ohm-in to about 100 Ohm-in, etc.) and a range that combines two integers that fall between two of the above-referenced values (i.e., a range of from about 13 Ohm-in to about 96 Ohm-in, etc.).

The conductive gel may be provided with any skin adhesion rate that allows the conductive gel to function in accordance with the present disclosure. For example (but not by way of limitation), the skin adhesion rate of the gel may be at least about 100 g/inch, at least about 110 g/inch, at least about 120 g/inch, at least about 130 g/inch, at least about 140 g/inch, at least about 150 g/inch, at least about 160 g/inch, at least about 170 g/inch, at least about 180 g/inch, at least about 190 g/inch, at least about 200 g/inch, at least about 210 g/inch, at least about 220 g/inch, at least about 230 g/inch, at least about 240 g/inch, at least about 250 g/inch, at least about 260 g/inch, at least about 270 g/inch, at least about 280 g/inch, at least about 290 g/inch, at least about 300 g/inch, or higher, as well as a range of any of the above values (a range of from about 120 g/inch to about 300 g/inch, etc.), and a range that combines two integers that fall between two of the above-referenced values (i.e., a range of from about 115 g/inch to about 295 g/inch, etc.).

The conductive gel may be provided with any thickness that allows the conductive gel to function in accordance with the present disclosure. Non-limiting examples of thicknesses that may be utilized in accordance with the present disclosure include about 1 mil, about 5 mil, about 10 mil, about 15 mil, about 20 mil, about 25 mil, about 30 mil, about 35 mil, about 40 mil, about 45 mil, about 50 mil, about 55 mil, about 60 mil, about 65 mil, about 70 mil, about 75 mil, about 80 mil, about 85 mil, about 90 mil, about 95 mil, about 100 mil, or higher, as well as a range that combines any two of the above-referenced values (i.e., a range of from about 10 mil to about 50 mil, etc.), and a range that combines two integers that fall between two of the above-referenced values (i.e., a range of from about 12 mil to about 48 mil, etc.).

In certain particular (but non-limiting) embodiments, the conductive gel has a shelf life of at least about six months. For example (but not by way of limitation), the conductive gel has a shelf life of at least about 9 months or at least about 12 months.

In one embodiment, the conductive gel element 128 is separate from the first conductive pad 100*a*. When the conductive gel element 128 is separate from the first conductive pad 100*a*, the conductive gel element 128 may have a first removeable protection layer 174 covering at least a portion of the electrode element 124 or the conductive gel layer 168*a* that, when removed, such as by the user, allows the user to attach the conductive gel layer 168*a* to the electrode element 124 of the first conductive pad 100*a*, and more specifically, to directly connect either the electrode layer 140 or the conductive support layer 144 to the conductive gel element 128. The first removeable protection layer 174 permits the electrode element 124 and the conductive gel element 128 to be constructed separately and adhered together at a later time. The step of adhering the electrode element 124 to the conductive gel element 128 can be accomplished by the patient or healthcare provider at a point of care, or by a manufacturer of the first conductive pad 100*a*. Additionally, the conductive gel element 128 may include a second removeable protection layer 176 covering at least a portion of the conductive gel layer 168*b* that when removed, such as by the user, allows the user to attach the conductive gel layer 168*b* to the patient, such as to the patient's skin on or over the target area.

In one embodiment, the first conductive pad 100*a* may be shaped at a point of use (e.g., with scissors) to correspond to the target area of the patient. For example only and not by way of limitation, the first conductive pad 100*a* may be cut, or otherwise modified, to remove a portion of the first conductive pad 100*a* in order to accommodate an ear wherein the portion removed would otherwise be over the ear. By doing so, better adhesion of the first conductive pad 100*a* to the patient's head may be achieved as well as an increase in comfort of the patient. As another example, the first conductive pad 100*a* may be cut or otherwise modified to fit around a joint of the patient, such as, and not limited to, cutting the first conductive pad 100*a* that is placed on a patient's knee in a manner that would allow the patient to continue to use their knee while the first conductive pad 100*a* is attached, or, further, use their knee while undergoing treatment from TTFields. Shaping of the first conductive pad 100*a* can be pre-structured or the first conductive pad 100*a* can be made sufficiently flexible so that shaping of the first conductive pad 100*a* is readily achievable. One important consideration when modifying the first conductive pad 100*a* is any cut through the electrode layer 140 such that a portion of the first conductive pad 100*a* is electrically isolated from the remainder of the first conductive pad 100*a* may have adverse therapeutic consequences.

Referring to FIG. 6, shown therein is another embodiment of a conductive pad 136. The conductive pad 136 is identical in construction and function as the first conductive pad 100*a* described above, with the exception that the electrode element 124 and the conductive gel element 128 are arranged to form a plurality of conductive regions 142*a-h* connected to the lead 58*a*. Eight conductive regions 142*a-h* are shown in FIG. 6 by way of example. The conductive pad 136 includes the durable topcoat layer 120 extending over and between the conductive regions 142*a-h*. In this embodiment, the durable topcoat layer 120 may be formed of a non-conductive material, or be formed of an electrically conductive material that does not receive electrical current from the conductive regions 142*a-h*. The conductive regions 142*a-h* are electrically isolated by one or more dielectric region 146 extending between each adjacently disposed pair of conductive regions 142*a-h*. The dielectric region 146 can be formed by interleaving a dielectric element laterally between each pair of adjacently disposed conductive regions 142*a-h*. The lead 58*a* may include two or more isolated conductor 150 such that each conductive region 142*a-h* is coupled to the generator 54 independently, thus allowing the generator 54 to independently control the TTField generated by each conductive region 142*a-h*. In such an embodiment, the electronic apparatus 50 may alternate between one or more conductive region 142*a-h* of the conductive pad 136, thus creating and shaping TTFields with increased specificity and precision. A single conductive pad 136 having multiple conductive regions 142*a-h*, can be used as a substitute or in conjunction with the pads 70*a* and 70*b*.

In one embodiment, the generator 54, connected to the conductive pad 136, may supply a first electric signal having a first power and a first frequency to a first group of one or more conductive region 142*a-h* (e.g., conductive region 142*a* and conductive region 142*b*, for example) at a first instance in time to generate a first TTField. The generator 54, at a second instance in time, may supply a second electric signal having a second power, the same as or different from the first power, and a second frequency, the same as or different from the first frequency, to a second group of one or more conductive region 142*a-h* (e.g., conductive region 142*b* and conductive region 142*c*, for example) to generate a second TTField. The second group may include one or more conductive region 142*a-h* included in the first group, or may not include one or more conductive region 142*a-h* included in the first group. The first TTField and the second TTField may target the same target area or may target different target areas. In one embodiment, the first instance in time and the second instance in time may overlap, that is, the generator 54 may supply the second electric signal to the second group while also supplying the first electric signal to the first group. In such an embodiment, the first group and the second group may be mutually exclusive.

In one embodiment, the generator 54, connected to the conductive pad 136, may supply a first electrical signal having a first power and a first frequency to a first group of one or more conductive region 142*a-h* (e.g., conductive region 142*a* and conductive region 142*b*, for example) and supply a second electrical signal having a second power and a second frequency to a second group of one or more conductive region 142*a-h* (e.g. conductive region 142*b* and conductive region 142*c*, for example) at the same instance in time. That is, the generator 54, may simultaneously supply the first electric signal to the first group and the second electric signal to the second group. While the above embodiments describe only the first group and the second group, it is understood that there may be more than two groups. In one embodiment, the number of groups is dependent on the number of combinations of the conductive regions 142*a-h*.

In one embodiment, the generator 54 may be connected to the conductive pad 136 and another pad, such as the pad 70*b*. In such an embodiment, the generator 54 may supply the electric signal to the one or more conductive region 142*a-h* of the conductive pad 136. The one or more conductive region 142*a-h* receiving the electric signal may then generate a TTField between each of the one or more conductive region 142*a-h* of the conductive pad 136 and the pad 70*b*.

Referring now to FIG. 7, shown therein is a 780 of experimental data of a first experiment of an exemplary embodiment of the first conductive pad 100*a* being used as the pad 70*a* and the pad 70*b* and a second experiment of a conventional non-conductive electrode array 164, having electrodes with a non-conductive ceramic disk separating a conductive layer from a conductive gel layer, for example, similar to the electrode array disclosed in U.S. Pat. No. 8,715,203 titled "Composite Electrode". Shown in the table 180 is a temperature reading in degrees Celsius measured by a plurality of temperature sensor 184*a-h*, each temperature sensor corresponding to a specific location on the pad 70*a*, the pad 70*b*, a first electrode array 164*a*, and a second electrode array 164*b*. In these experiments, the pad 70*a*, the pad 70*b* were attached to a watermelon. At a separate instant of time, the pad 70*a* and the pad 70*b* were removed from the watermelon, and a first electrode array 164*a*, and a second electrode array 164*b* were attached to the watermelon. In both experiments, the electrode array 164 having temperature sensors 154 was used to measure a temperature at eight (8) predetermined locations.

For the first experiment, the generator 54 was set to provide 218 Volts at a current of 3597 mA and a frequency of 149 kHz to the first conductive pad 100*a* and the second conductive pad 100*b*. For the first experiment, the current was increased until one or more of the temperature sensor 184*a-h* associated with either the pad 70*a* or the pad 70*b* and placed at predetermined locations read about 40 degrees Celsius or until the test equipment could no longer increase the provided power, that is, when the provided current is about 3600 mA. As shown, a temperature of 23.9 degrees Celsius was measured by temperature sensor 184*c* on the first conductive pad 100*a*. Thus, the current of 3597 mA provided to the pad 70*a* and the pad 70*b* does not cause the pad 70*a* or the pad 70*b* to reach a comfortability threshold. In one embodiment, the comfortability threshold is the temperature at which a patient would be made uncomfortable while using the pads 70*a* and 70*b*. In one embodiment, the comfortability threshold is a temperature at or about 40 degrees Celsius.

For the second experiment, the generator 54 was set to provide 168 Volts at a current of 1203 mA and a frequency of 149 kHz to the first electrode array 164*a* and the second electrode array 164*b*. For the second experiment, the current was increased until one or more of the temperature sensor 184*a-h* of either the first electrode array 164*a* or the second electrode array 164*b* and placed at the predetermined locations read about 40 degrees Celsius or until the test equipment could no longer increase the provided power. As shown, a temperature of 39.3 degrees Celsius was measured by temperature sensor 184*h* on the second electrode array 164*b*. Thus, the current of 1203 mA provided to the first electrode array 164*a* and the second electrode array 164*b* is the maximum provided current before the electrode array 164 surpasses a comfortability threshold. In one embodiment, the comfortability threshold is the temperature at which a patient would be made uncomfortable while using the electrode array 164. In one embodiment, the comfortability threshold is a temperature at or about 40 degrees Celsius.

The temperature sensors 154*a-h* were integrated into each electrode array 164. In order to measure the temperature of the pad 70*a* and the pad 70*b*, which in the experimental embodiment did not include a temperature sensor, an electrode array 164 was placed over the pad 70*a* and the second conductive pad 70*b*. It should be noted that, while the experimental embodiment of the pad 70*a* and the pad 70*b* does not include a temperature sensor, in another embodiment, the pad 70*a* and the pad 70*b* may include one or more temperature sensor 184. In yet another embodiment, the pad 70*a* and the pad 70*b* may include temperature sensors 154 located at various positions to measure a temperature at such various locations to, for example, determine whether a hot-spot is forming in a particular part of the first conductive pad 70*a* and second conductive pad 70*b*.

In a preferred embodiment, the generator 54 is adapted to provide only an AC signal to the leads 58*a* and 58*b* without any DC signal or DC offset voltage. In this embodiment, there is no need for any DC blocking component in the leads 58*a* and 58*b*, or the pad 70*a* and the pad 70*b* to prevent a DC signal or DC offset voltage from passing into the patient. In the event of a malfunction of the generator 54 or the like, however, a DC blocking component should be provided to protect the patient from an inadvertent DC signal or DC offset voltage as a safety measure.

Figure 8:
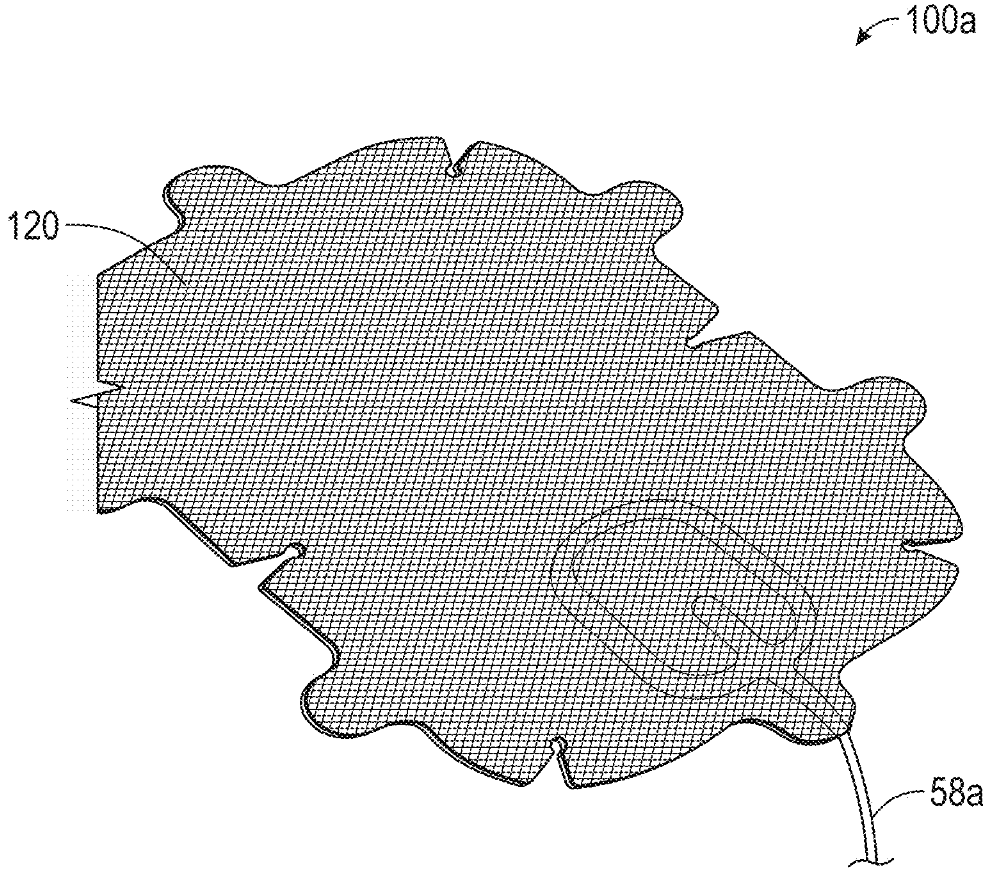
FIG. 8 is a perspective view of an exemplary embodiment of the first conductive pad depicted in FIG. 3.

Referring now to FIG. 8, shown therein is an exemplary embodiment of a perspective view of the first conductive pad 100*a* coupled to the lead 58*a* and having the durable topcoat layer 120 visible. From the perspective view, additional components of the first conductive pad 100*a*, such as the electrode element 124, or the conductive gel element 128 are not visible.

Certain non-limiting embodiments of the present disclosure are related to kits that include any of the components of the TTField generating systems, such as the electronic apparatus 50, described herein. In one embodiment, one or more of the pad 70*a* and the pad 70*b* may be packaged as part of a kit. In one embodiment, the kit may include the pad 70*a* and the lead 58*a* connected to the electrode element 124. In another embodiment, the kit may include the pad 70*a* and the pad 70*b*, and the leads 58*a* and 58*b*. In each of the above embodiments, the lead 58*a* may be mechanically coupled to the pad 70*a*, and the lead 58*b* may be mechanically coupled to the pad 70*b*, for example, by a rivet, by solder, by adhesive, by welding, or other electrically conductive coupling means. In each of the above embodiments, the kit may further include the blocking capacitor 82*a* or the blocking capacitor 82*b* positioned such that the electric signal passes through the blocking capacitor 82*a* or the blocking capacitor 82*b*. In each of the above embodiments, the first conductive pad 100*a* when used as the pad 70*a* and/or the pad 70*b* may include the second removeable protection layer 176 attached to and covering at least a portion of (or the entire) the conductive gel element 128 such that the second removeable protection layer 176 protects the conductive gel element 128 from potential damage, such as loss of adhesion or disruption of or discontinuities. The second removeable protection layer 176 may be easily removed by the user before the first conductive pad 100*a* is applied to the patient. In one embodiment, the second removeable protection layer 176 is an electric insulator, such that the second removeable protection layer 176 prevents or substantially reduces accidental application of the electric signal before the first conductive pad 100*a* is attached to the patient. In each of the above embodiments, the kit may include a plurality of the first conductive pad 100*a*, and may include a number of conductive pads (constructed in accordance with the present disclosure) that, when applied to the patient, have a therapeutic benefit. In addition, the kit can further include a set of written instructions explaining how to use one or more components of the kit. A kit of this nature can be used in any of the methods described or otherwise contemplated herein.

Figure 9:
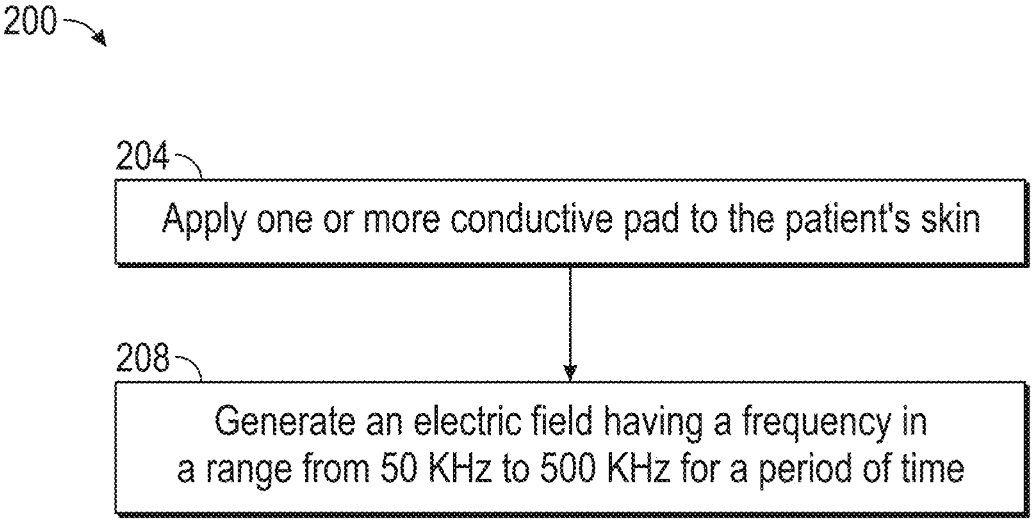
FIG. 9 is a diagram of an exemplary embodiment of a process of treating a tumor utilizing the conductive pads of the present disclosure.

Referring now to FIG. 9, shown therein is an exemplary embodiment of a process 200 of using the electronic apparatus 50 and the first conductive pad 100*a* as the pad 70*a* and the pad 70*b*, or the conductive pad 136 to apply a TTField to a patient. The process 200 generally comprises the steps of: applying the first conductive pad 100*a* as the pad 70*a* and the first conductive pad 100*a* as the pad 70*b* to the patient's skin and/or the conductive pad 136 (step 204) and generating an alternating electric field having a frequency in a range of from about 50 kHz to about 576 kHz for a period of time (step 208).

The step of applying the first conductive pad 100*a* to the patient's skin 179 may be performed by the user. In one embodiment, before applying the first conductive pad 100*a* to the patient's skin, the patient's skin may need to be cleaned (e.g., such as but not limited to, cleansing of the skin of foreign matter or biological matter and shaving of the skin, if necessary) to enable the conductive gel element 128 to adhere to the patient's skin.

The step of generating an alternating electric field (TTField) (step 208) may be performed by the generator 54 and may be instantiated by an operation performed by the user or control box 66. In one embodiment, step 208 may be performed more than one time and the period of time for which the step 208 is performed a first time may be the same as or different from the period of time for which the step 208 is performed a second time (or other period(s) of time beyond the second time). In some embodiments, step 208 is only performed once before the process 200 is repeated. There may be a time period between each time the process 200 is repeated. Each time the process 200 is repeated, the time period may be the same as or different from the previous time period. Each time the process 200 is repeated, the first conductive pad 100*a* and the second conductive pad 100*b* may be placed in the same or a different position on the patient's skin.

The following is a number list of non-limiting illustrative embodiments of the inventive concept of the second mode disclosed herein:

1. A system, comprising:
 a generator configured to generate an electrical signal having an alternating current waveform at a frequency in a range from 50 kHz to 500 kHz;
 a first conductive lead electrically coupled to the generator, the first conductive lead configured to carry the electrical signal;
 a first conductive pad having a first electrode element directly connected to a conductive gel element, and the first hydrogel element is configured to be in contact with a patient's skin;
 a second conductive lead electrically coupled to the generator, the second conductive lead configured to carry the electrical signal; and
 a second conductive pad having a second electrode element directly connected to a second conductive gel element, and the second conductive gel element being configured to be in contact with a patient's skin.
2. The system of illustrative embodiment 1, wherein the first electrode element includes an electrode layer electrically coupled to a conductive support layer, the conductive support layer being intermediate to the electrode layer and the conductive gel element.
3. The system of illustrative embodiment 2, wherein the second electrode element includes an electrode layer electrically coupled to a conductive support layer, the conductive support layer being intermediate to the electrode layer and the conductive gel element.
4. The system of illustrative embodiment 1, further comprising a blocking capacitor configured to block direct current in the electrical signal.
5. The system of illustrative embodiment 4, wherein the blocking capacitor is a non-polarized capacitor.
6. The system of illustrative embodiment 4, wherein the blocking capacitor has a capacitance of about 1 μF.
7. The system of illustrative embodiment 4, wherein the generator includes the blocking capacitor.
8. The system of illustrative embodiment 4, wherein either the first conductive pad, the second conductive pad, or both the first conductive pad and the second conductive pad include the blocking capacitor.
9. The system of illustrative embodiment 4, wherein the blocking capacitor is a first blocking capacitor and further comprising a second blocking capacitor configured to block direct current in the electrical signal.
10. The system of illustrative embodiment 9, wherein either the first conductive pad, the second conductive pad, or both the first conductive pad and the second conductive pad include the second blocking capacitor.
11. The system of illustrative embodiment 1, wherein the first conductive gel element further includes a first hydrogel layer, a support layer, and a second hydrogel layer, the first hydrogel layer being a first electrically conductive hydrogel and the second hydrogel layer being a second electrically conductive hydrogel.
12. The system of illustrative embodiment 11, wherein the first electrically conductive hydrogel and the second electrically conductive hydrogel are not the same hydrogel.
13. The system of illustrative embodiment 11, wherein the support layer is electrically conductive.
14. The system of illustrative embodiment 1, wherein the second hydrogel element further includes a first hydrogel layer, a support layer, and a second hydrogel layer, the first hydrogel layer being a first electrically conductive hydrogel and the second hydrogel layer being a second electrically conductive hydrogel.
15. The system of illustrative embodiment 14, wherein the first electrically conductive hydrogel and the second electrically conductive hydrogel are not the same hydrogel.
16. The system of illustrative embodiment 14, wherein the support layer is electrically conductive.

17. The system of illustrative embodiment 1, further comprising one or more temperature sensor configured to measure a temperature of the first conductive pad.
18. The system of illustrative embodiment 17, further comprising a control box configured to monitor the one or more temperature sensor and turn off the generator if the temperature exceeds a comfortability threshold.
19. The system of illustrative embodiment 18, wherein the comfortability threshold is about 40 degrees Celsius.
20. A conductive pad, comprising:
a topcoat layer;
an electrode element connected to the topcoat layer, and configured to receive an electrical signal from a generator producing an electric signal as a TTField; and
a conductive gel element directly connected to the electrode element so as to receive an electrical current from the electrode element, the conductive gel element configured to be in contact with a patient's skin.
21. The conductive pad of illustrative embodiment 20, further comprising a conductive lead configured to carry the electrical signal, the conductive lead configured to be electrically coupled to the generator, the conductive lead electrically coupled to the electrode element.
22. The conductive pad of illustrative embodiment 20, wherein the conductive gel element further includes a first conductive gel layer, a support layer, and a second conductive gel layer, the first hydrogel layer being a first electrically conductive gel and the second conductive gel layer being a second electrically conductive gel.
23. The conductive pad of illustrative embodiment 22, wherein the first electrically conductive gel and the second electrically conductive gel are not the same conductive gel.
24. The conductive pad of illustrative embodiment 22, wherein the support layer is electrically conductive.
25. The conductive pad of illustrative embodiment 22, further comprising a blocking capacitor configured to block direct current in the electrical signal.
26. The conductive pad of illustrative embodiment 25, wherein the blocking capacitor is a non-polarized capacitor.
27. The conductive pad of illustrative embodiment 25, wherein the blocking capacitor has a capacitance of about 1 μF.
28. The conductive pad of illustrative embodiment 20, wherein the topcoat layer, the electrode element, and the conductive gel element are constructed of flexible materials and configured to conform to a body of a patient.
29. A method, comprising:
applying at least two conductive regions to a patient;
coupling the conductive regions to a generator before or after applying the at least two conductive regions to the patient, the generator configured to generate an electrical signal having an alternating current waveform at frequencies in the range from 50 kHz to 500 kHz, each conductive region having an electrode element directly connected to a conductive gel element so as to supply an electrical current from the electrode element to the conductive gel element, the electrode elements being electrically coupled to the generator and, upon receiving the electrical signal supplies electrical current to the conductive gel element, the conductive gel element being in contact with a patient's skin; and
activating the generator to supply the electrical signal to the electrode elements, thereby supplying electrical current to the patient through the conductive gel element.
30. The method of illustrative embodiment 29 wherein at least one lead is provided to electrically couple the electrode elements to the generator.
31. The method of illustrative embodiment 29, wherein the electrical signal is passed through a blocking capacitor configured to block direct current in the electrical signal.
32. The method of illustrative embodiment 31, wherein the blocking capacitor is a non-polarized capacitor.
33. The method of illustrative embodiment 31, wherein the blocking capacitor has a capacitance of about 1 μF.
34. The method of illustrative embodiment 29, wherein the electrode element, and the conductive gel element are constructed of flexible materials and configured to conform to a body of a patient.

Third Mode: Conductive Pad with Air-Channels

A third mode of the present disclosure includes a system and method of implementing the system, the system comprising a generator configured to generate an electrical signal having an alternating current waveform at a frequency in a range from 50 kHz to 576 kHz; a first conductive lead electrically coupled to the generator, the first conductive lead configured to carry the electrical signal; a first conductive pad having a first electrode element electrically coupled to a first conductive gel element to supply electrical current to the first conductive gel element, wherein the first electrode element is electrically coupled to the first conductive lead, and the first conductive gel element is configured to be in contact with a patient's skin, the first conductive gel element having one or more first air-channel; a second conductive lead electrically coupled to the generator, the second conductive lead configured to carry the electrical signal; and a second conductive pad having a second electrode element electrically coupled to a second conductive gel element to supply electrical current to the second conductive gel element, wherein the second electrode element is electrically coupled to the second conductive lead, and the second conductive gel element is configured to be in contact with a patient's skin, the second conductive gel element having one or more second air-channel.

Referring back to FIG. 9, in one embodiment, during the process 200, applying the first conductive pad 100*a* as the pads 70*a* and 70*b*, and/or the conductive pad 136 to the patient's skin (step 204) may result in the first conductive pad 100*a* and/or the conductive pad 136 being attached to the patient's skin for an extended period of time. Certain undesirable symptoms may occur due to an extended application of the first conductive pad 100*a* and/or the conductive pad 136 being attached to the patient's skin for an extended period of time, such as, for example, maceration of a portion of the patient's skin in extended contact with the first conductive pad 100*a* and/or the conductive pad 136. Such undesirable symptoms may be mitigated by providing one or more air-channel 228 such as shown below in FIGS. 10-15.

Figure 10:
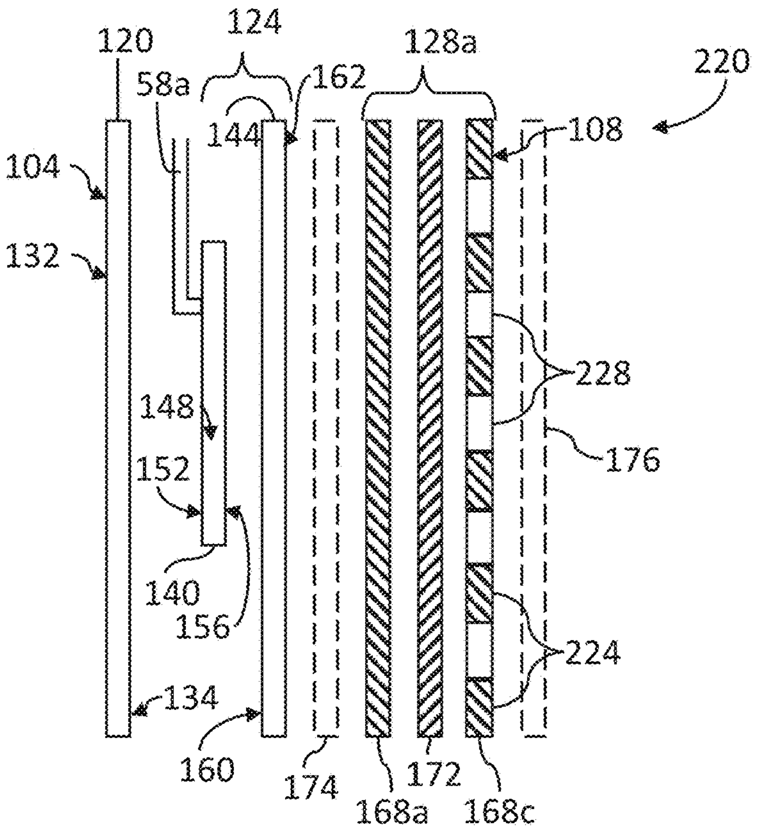
FIG. 10 is an exploded side view of another embodiment of a conductive pad having a plurality of spatially disposed conductive gel elements forming an air-channel between each adjacently disposed pair of conductive gel elements.

Referring now to FIG. 10, shown therein is an exploded side view of a first exemplary embodiment of a conductive pad 220 constructed in accordance with the present disclosure for use as the pad 70*a* and/or the pad 70*b*. As shown in FIG. 10, the conductive pad 220 is provided with a durable topcoat layer 120, an electrode element 124, and a conductive gel element 128*a*, similar to the conductive gel element 128 shown in FIG. 4. The electrode element 124 is positioned between the durable topcoat layer 120 and the conductive gel element 128*a*. The durable topcoat layer 120, the electrode element 124, and the conductive gel element 128*a* may be bonded together to form a composite structure that has the sufficiently flexible qualities discussed above. In some embodiments, the electrode element 124 is electrically coupled to the conductive gel element 128*a* so as to supply an electrical current from the electrode element 124 to the conductive gel element 128*a*. In this embodiment, the conductive pad 220 does not include a dielectric layer electrically isolating the electrode element 124 from the conductive gel element 128*a*.

In this embodiment, the conductive gel element 128*a* includes one or more conductive gel layer 168 having a bulk electron transport agent providing a source of free ions therein to enable electrical conductivity. As described above, the one or more conductive gel layer 168 is formed primarily of a conductive gel or a semi-solid conductive gel. In the embodiment depicted in FIG. 10, the conductive gel element 128 includes two conductive gel layers 168*a* and 168*c* bonded to a support layer 172. The support layer 172 can either be constructed of a conductive material, or the support layer 172 may be constructed of a nonconductive material but with a structure so as to permit the conductive gel layers 168*a* and 168*c* to become embedded into the structure and facilitate conductivity across the support layer 172. In this embodiment, the conductive gel layer 168*c* is formed of two or more conductive gel regions 224 separated such that adjacent conductive gel regions 224 do not intersect, thereby forming one or more air-channels 228. The one or more air-channels 228 allow air to contact the patient's skin at one or more location within the outer peripheral edge 148 of the conductive pad 220. In some embodiments, a support layer 172 is not present.

Figure 11:
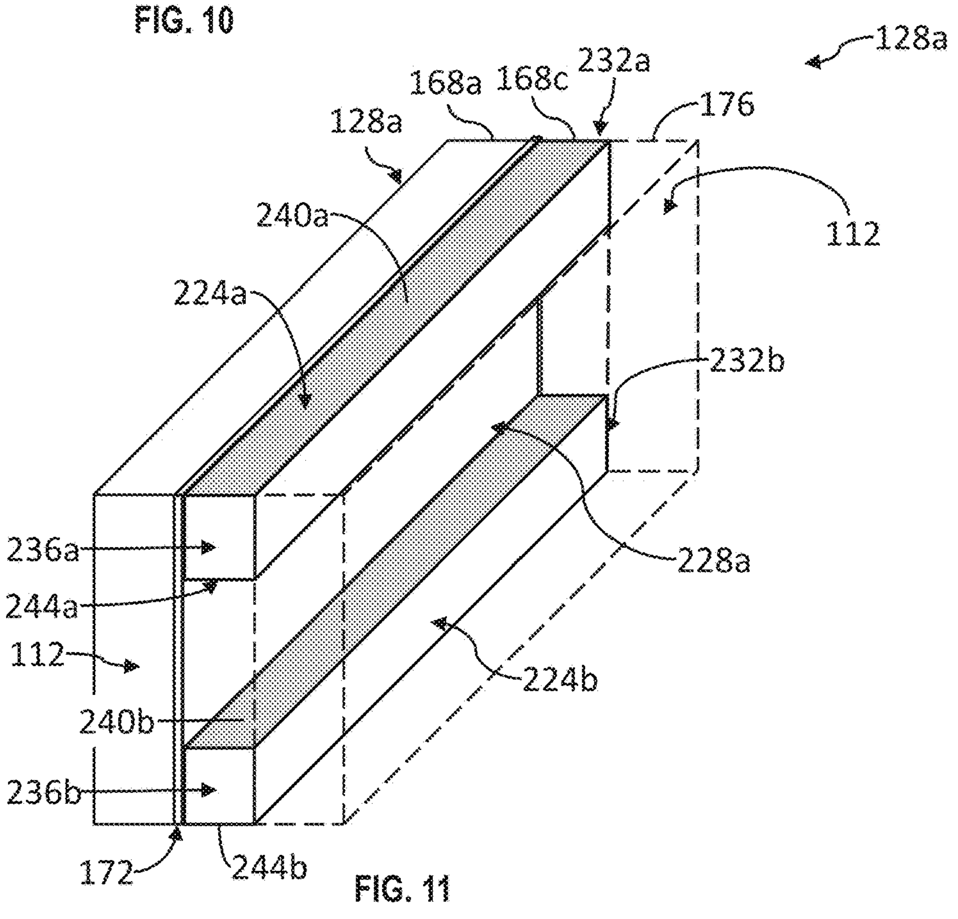
FIG. 11 is a perspective view of an exemplary embodiment of a portion of the conductive gel element and the second removeable protection layer of the conductive pad of FIG. 10.

Referring now to FIG. 11, shown therein is a perspective view of an exemplary embodiment of a portion of the conductive gel element 128*a* and the second removeable protection layer 176 of the conductive pad 220 of FIG. 10. Further shown is a first conductive gel region 224*a* adjacent a second conductive gel region 224*b* and spatially disposed to form a first air-channel 228*a*. The first conductive gel region 224*a* has a first end 232*a* and a second end 236*a*, both the first end 232*a* and the second end 236*a* coincidental to the outer peripheral edge 112 of the conductive pad 220. The second conductive gel region 224*b* has a first end 232*b* and a second end 236*b*, both the first end 232*b* and the second end 236*b* coincidental to the outer peripheral edge 112 of the conductive pad 220. The first conductive gel region 224*a* further includes a first wall portion 240*a* and a second wall portion 244*a* and the second conductive gel region 224*b* further includes a first wall portion 240*b* and a second wall portion 244*b*. The first air-channel 228*a* is thus bound by the conductive gel layer 168*a*, the second removeable protection layer 176, the first wall portion 240*b* of the second conductive gel region 224*b* and the second wall portion 244*a* of the first conductive gel region 224*a*, and extends from a first position on the outer peripheral edge 112, the first position being between the first end 232*a* of the first conductive gel region 224*a* and the first end 232*b* of the second conductive gel region 224*b*, to a second position on the outer peripheral edge 112, the second position being between the second end 236*a* of the first conductive gel region 224*a* and the second end 236*b* of the second conductive gel region 224*b*. It is understood that while the portion of the conductive gel layer 168*a*, the conductive gel layer 168*b*, and the second removeable protection layer 176 of the conductive pad 220 shown in FIG. 11 depicts only two conductive gel regions 224, the conductive gel layer 168*b* of the conductive pad 220 may include a plurality of conductive gel regions 224 spatially disposed to form two or more air-channels 228.

Figure 12:
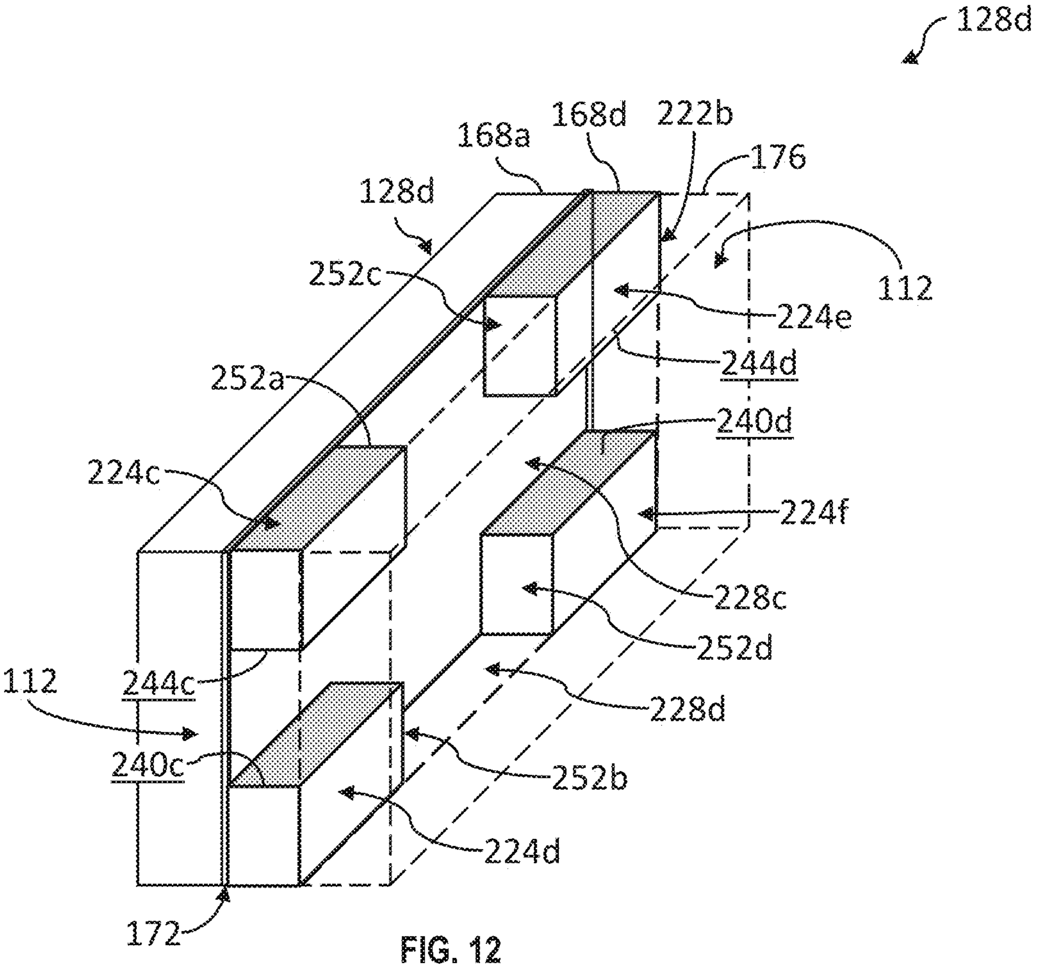
FIG. 12 is a perspective view of an alternative exemplary embodiment of a portion of the conductive gel element and the second removeable protection layer of the conductive pad of FIG. 10.

Referring now to FIG. 12, shown therein is a perspective view of an exemplary embodiment of a portion of a conductive gel element 128*d* and the second removeable protection layer 176 of the conductive pad 220 of FIG. 10. Shown therein is the conductive gel layer 168*a*, bonded to support layer 172, which is in turn bonded to conductive gel layer 168*d*. The support layer 172 is optional. In some embodiments, the conductive gel layer 168*d* is bonded directly to the conductive gel layer 168*a*. The conductive gel layer 168*d* is comprised of a plurality of spatially disposed conductive gel regions 224 which may be arranged in a grid pattern. In some embodiments, the conductive gel regions 224 include a first conductive gel region 224*c*, a second conductive gel region 224*d*, a third conductive gel region 224*e*, and a fourth conductive gel region 224*f*, each conductive gel region 224*c-f* is adjacent to another conductive gel region 224 and spatially disposed to form a first air-channel 228*c*, between the first conductive gel region 224*c* and the second conductive gel region 224*d* and extending between the third conductive gel region 224*e* and the fourth conductive gel region 224*f*, and a second air-channel 228*d*, between the first conductive gel region 224*c* and the third conductive gel region 224*e* and extending between the second conductive gel region 224*d* and the fourth conductive gel region 224*f*.

The first conductive gel region 224*c* further includes a first wall portion 244*c*, the second conductive gel region 224*d* further includes a second wall portion 240*c*, the third conductive gel region 224*e* further includes a third wall portion 244*d*, and the fourth conductive gel region 224*f* further includes a fourth wall portion 240*d*. The first air-channel 228*c* is thus bound by the conductive gel layer 168*a*, the second removeable protection layer 176, the first wall portion 244*c* and the second wall portion 240*c* and is further bound by the fourth wall portion 240*d* and the third wall portion 244*d*, and extends from a first position on the outer peripheral edge 112 to a second position on the outer peripheral edge 112.

The first conductive gel region 224*c* further includes a fifth wall portion 252*a*, the second conductive gel region 224*d* further includes a sixth wall portion 252*b*, the third conductive gel region 224*e* further includes a seventh wall portion 252*c*, and the fourth conductive gel region 224*f* further includes an eighth wall portion 252*d*. The second air-channel 228*d* is thus bound by the conductive gel layer 168*a*, the second removeable protection layer 176, the fifth wall portion 252*a* and the seventh wall portion 252*c* and is further bound by the sixth wall portion 252*b* and the eighth wall portion 252*d*, and extends from a third position on the outer peripheral edge 112 to a fourth position on the outer peripheral edge 112. It is understood that while the portion of the conductive gel layer 168*a*, the conductive gel layer 168*d*, and the second removeable protection layer 176 of the conductive pad 220 shown in FIG. 12 depicts only four conductive gel regions 224, the conductive gel layer 168*d* of the conductive pad 220 may include a plurality of conductive gel regions 224 spatially disposed to form a plurality of air-channels 228.

Figure 13:
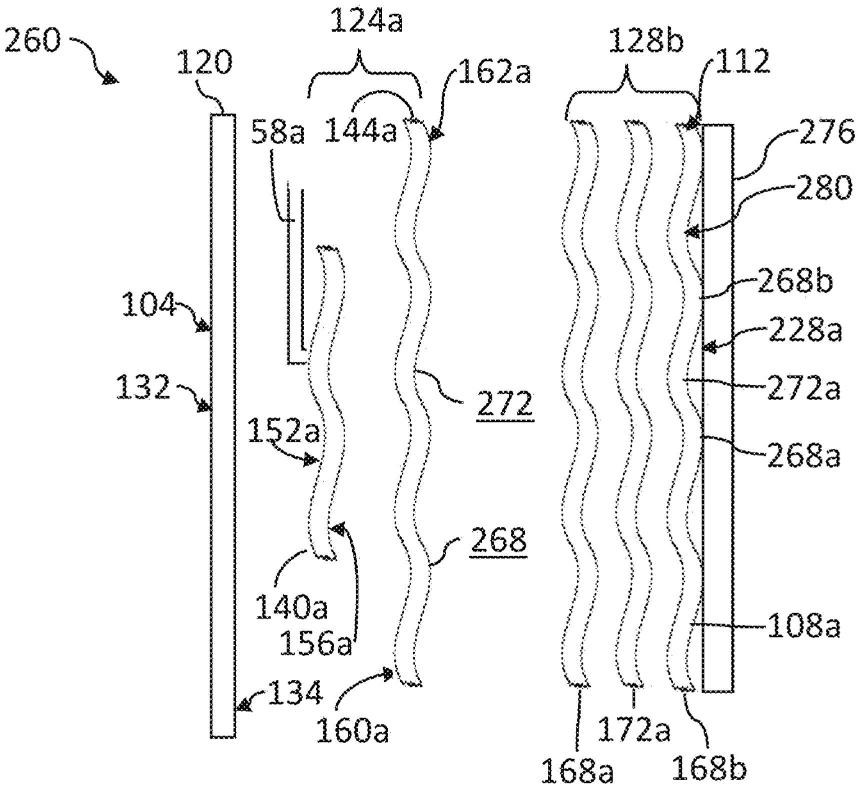
FIG. 13 is an exploded side view of another embodiment of a conductive pad having an electrode element and a conductive gel element formed into a non-planar shape (in this example a corrugated shape) configured to mate together thereby providing a patient engaging surface having a plurality of wall portions forming an air-channel between each adjacently disposed pair of wall portions in accordance with the present disclosure.

In one embodiment, when the conductive pad 220 is placed on the patient, the conductive pad 220 of FIGS. 10 and 11 form the first air-channel 228*a* bound by the conductive gel layer 168*a*, the patient, the first wall portion 240*b* of the second conductive gel region 224*b* and the second wall portion 244*a* of the first conductive gel region 224*a*, and extends from the first position on the outer peripheral edge 112 to the second position on the outer peripheral edge 112. As shown in FIG. 13, when the conductive pad 220 is placed on the patient, the second air-channel 228*d* is thus bound by the conductive gel layer 168*a*, the patient, the fifth wall portion 252*a* and the seventh wall portion 252*c* and is further bound by the sixth wall portion 252*b* and the eighth wall portion 252*d*, and extends from a third position on the outer peripheral edge 112 to a fourth position on the outer peripheral edge 112.

Referring now to FIG. 13, shown therein is an exploded side view of a second exemplary embodiment of a conductive pad 260 constructed in accordance with the present disclosure. As shown in FIG. 13, the conductive pad 260 is provided with the durable topcoat layer 120, an electrode element 124*a*, and a conductive gel element 128*b*, similar to the embodiment shown in FIG. 4, however, the electrode element 124*a* and/or the conductive gel element 128*b* is modified. The electrode element 124*a* is positioned between the durable topcoat layer 120 and the conductive gel element 128*b*. The durable topcoat layer 120, the electrode element 124*a*, and the conductive gel element 128*b* may be bonded together to form a composite structure that has the sufficiently flexible qualities discussed above. In some embodiments, the electrode element 124*a* is electrically coupled to the conductive gel element 128*b* so as to supply an electrical current from the electrode element 124*a* to the conductive gel element 128*b*. In this embodiment, the conductive pad 260 does not include a dielectric layer electrically isolating the electrode element 124*a* from the conductive gel element 128*b*. In one or more embodiment, the conductive gel element 128*b* may further include the first removeable protection layer 174 and the second removeable protection layer 176, not shown in FIG. 13 for purposes of brevity.

In one embodiment shown in FIG. 13, a conductive support layer 144*a* may include a first surface 160*a* attached to or otherwise coupled to a second surface 156*a* of an electrode layer 140*a* and a second surface 162*a* in contact or coupled to a conductive gel element 128*b*. The conductive support layer 144*a* may be formed of a conductive carbon film configured to support the electrode layer 140*a* while also conductively coupling the electrode layer 140*a* to the conductive gel element 128*b*. In this embodiment, the conductive support layer 144*a* may be formed such that the conductive gel element 128*b* coupled to the conductive support layer 144*a* forms the one or more air-channel 228*a*.

In one embodiment, the conductive support layer 144*a* is non-planar and may be, for example, corrugated, e.g. the first surface 160*a* and the second surface 162*a* may be formed to have striae of one or more ridge 268 and groove 272, thereby causing the conductive gel element 128*b* attached thereto to exhibit similar corrugation which form one or more air-channel 228 (e.g. first air-channel 228*a*) between a patient 276 and a patient engaging surface 280 of the conductive gel layer 168*b* (e.g. a bottom 108*a*) when the conductive pad 260 is attached to the patient 276. The similar corrugation is shown, for example, as the first ridge 268*a*, the second ridge 268*b*, and the first groove 272*a*. A portion of the patient engaging surface 280 of the conductive gel layer 168*b* forms a first wall portion defined by the intersection of the first ridge 268*a* and the patient 276 and extending to the first groove 272*a*, and a second wall portion defined by the intersection of the second ridge 268*b* and the patient 276 and extending to the first groove 272*a*. The first wall portion and the second wall portion are an adjacently disposed pair of wall portions extending to the outer peripheral edge 112*b* of a conductive pad 260, thereby forming the first air-channel 228*a*. While only the first air-channel 228*a* has been described in detail, it is understood that there may be more than one air-channel 228 and that any adjacently disposed pair of wall portions may form an air-channel 228.

While the one or more ridge 268 and groove 272 are depicted as having uniform, or nearly uniform, widths, it is understood that the width of the one or more ridge 268 and groove 272 may vary. Similarly, while it is shown that the striae of the one or more ridge 268 and groove 272 are parallel, it is understood that the one or more ridge 268 and groove 272 may form any pattern such that one or more air-channel 228 is formed between the conductive gel element 128 and the patient 276.

In one embodiment shown in FIG. 13, the conductive gel element 128*b* includes two conductive gel layers 168*a* and 168*b* bonded to a support layer 172*a*. The support layer 172*a* can either be constructed of a conductive material, or the support layer 172*a* may be constructed of a nonconductive material but with a structure so as to permit the conductive gel layers 168*a* and 168*b* to become embedded into the structure and facilitate conductivity across the support layer 172*a*. The support layer 172*a* may be non-planar and may be, for example, corrugated, e.g. the support layer 172*a* may be constructed such that the support layer 172*a* includes striae of one or more ridge 268 and groove 272, thereby causing the conductive gel layer 168*b* bonded thereto to exhibit similar corrugation which form one or more air-channel 228 (e.g. first air-channel 228*a*) between the patient 276 and a patient engaging surface 280 of the conductive gel layer 168*b* when the conductive pad 260 is attached to the patient 276. The similar corrugation is shown, for example, as the first ridge 268*a*, the second ridge 268*b*, and the first groove 272*a*. The portion of the patient engaging surface 280 of the conductive gel layer 168*b* forms the first wall portion defined by the intersection of the first ridge 268*a* and the patient 276 and extending to the first groove 272*a*, and the second wall portion defined by the intersection of the second ridge 268*b* and the patient 276 and extending to the first groove 272*a*. The first wall portion and the second wall portion are an adjacently disposed pair of wall portions extending to the outer peripheral edge 112 of the conductive pad 260, thereby forming the first air-channel 228*a*.

While only the first air-channel 228*a* has been described in detail, it is understood that there may be more than one air-channel 228 and that any adjacently disposed pair of wall portions may form the air-channel 228. While the one or more ridge 268 and groove 272 are depicted as having uniform, or nearly uniform, widths, it is understood that the width of the one or more ridge 268 and groove 272 may vary. Similarly, while it is shown that the striae of the one or more ridge 268 and groove 272 are parallel, it is understood that the one or more ridge 268 and groove 272 may form any pattern such that one or more air-channel 228 is formed between the conductive gel element 128*b* and the patient 276.

In one or more of the above embodiments, the conductive gel layers 168*a*, 168*b*, and/or 168*c* may be sprayed onto either the electrode element 124*a*, the first removeable protective layer 174, and/or the support layer 172*a* in a liquid state. In such an embodiment, the one or more of the conductive gel layers 168*a*, 168*b*, and/or 168*c* may be cured to a solid state having a uniform thickness (i.e., within manufacturing tolerances) to have a shape mimicking the shape of the electrode element 124*a*, the first removeable protective layer 174, and/or the support layer 172*a*. That is, the conductive gel layers 168*a*, 168*b*, and/or 168*c* may be exposed to an environment (e.g., UV light) causing the conductive gel layers 168*a*, 168*b*, and/or 168*c* to set. It is understood that the conductive gel layer **168*d* can be processed and formed in a similar manner to the conductive gel layer 168*c***.

Figure 14:
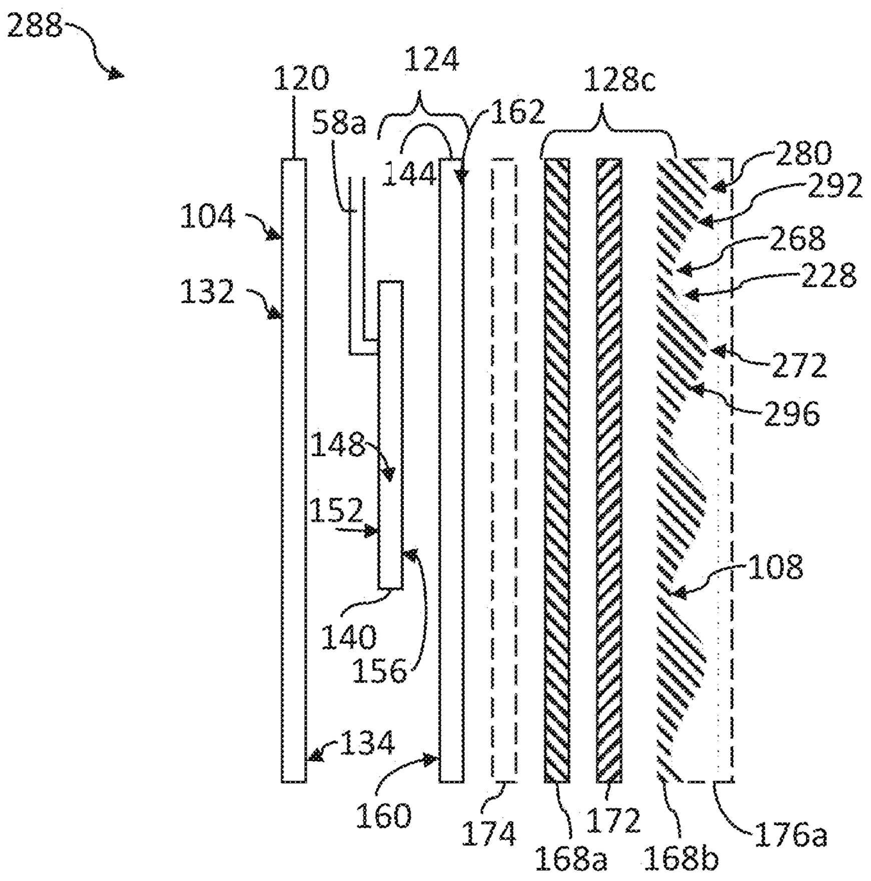
FIG. 14 is an exploded side view of another embodiment of the conductive pad in which a removeable protective layer is shaped so as to provide a non-planar form (in this example a corrugated shape) for receiving a conductive gel in liquid form thereby forming the patient engaging surface in the corrugated shape having a plurality of wall portions forming an air-channel between each adjacently disposed pair of wall portions in accordance with the present disclosure.

Referring now to FIG. 14, shown therein is an exploded side view of a third exemplary embodiment of the conductive pad 288 constructed in accordance with the present disclosure. As shown in FIG. 14, the conductive pad 288 is provided with the durable topcoat layer 120, the electrode element 124, and a conductive gel element **128*c*, similar to the embodiment shown in FIG. 4, however, a second removeable protection layer 176*a* is non-planar (e.g., stria) and configured to receive conductive gel in liquid state thereby shaping the conductive gel to follow the shape of the second removeable protection layer 176*a*. The electrode element 124 is positioned between the durable topcoat layer 120 and the conductive gel element 128*c*. The durable topcoat layer 120, the electrode element 124, and the conductive gel element 128*c* may be bonded together to form a composite structure that has the sufficiently flexible qualities discussed above. In some embodiments, the electrode element 124 is electrically coupled to the conductive gel element 128*c* so as to supply an electrical current from the electrode element 124 to the conductive gel element 128*c*. In this embodiment, the conductive pad 288 does not include a dielectric layer electrically isolating the electrode element 124 from the conductive gel element 128*c***.

In this embodiment, the conductive gel element **128*c* includes the first removeable protection layer 174 and the second removeable protection layer 176*a* attached to a patient engaging surface 280 of the conductive gel element 128*c* (e.g., the bottom 108). Here, the second removeable protection layer 176*a* may be formed such that one surface of the second removeable protection layer 176*a* being in contact with the patient engaging surface 280 is non-planar, such as, for example, by having one or more ridge 268 and groove 272. The ridge 268 in the second removable protection layer 176*a* forms a groove 292 in the patient engaging surface 280 of the conductive gel element 128*c*. Similarly, the groove 272 and the second removable protection layer 176*a* forms a ridge 296 in the patient engaging surface 280 of the conductive gel element 128*c*. An adjacent pair of the ridges 296 forms one or more air-channel 228 such as the formation of the one or more air-channel 228** described above in more detail.

Figure 15:
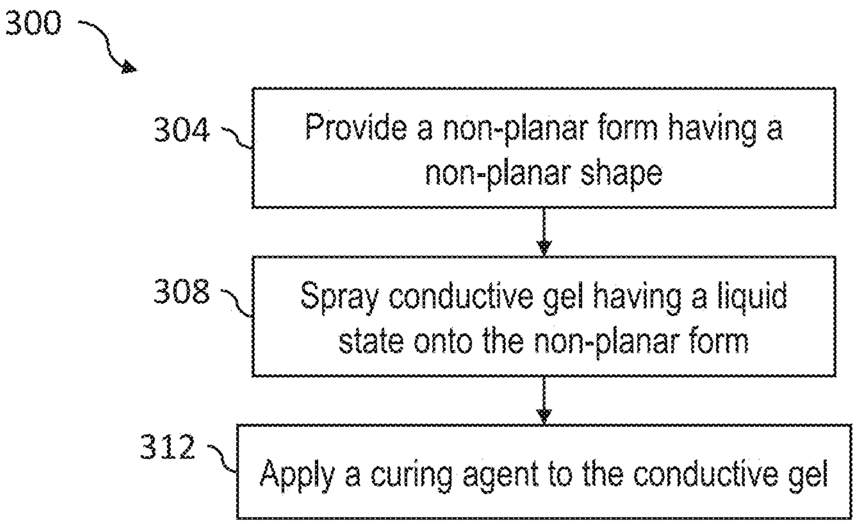
FIG. 15 is a process flow diagram of an exemplary embodiment of a process of forming the conductive gel element of the present disclosure.

Referring now to FIG. 15, shown therein is a process flow diagram of an exemplary embodiment of a process 300 for forming the conductive gel element of the present disclosure. The process 300 for forming the conductive gel element 128 generally comprises the steps of providing a non-planar form having a non-planar shape (step 304), spraying (or otherwise applying) conductive gel having a liquid state onto the non-planar form (step 308), and applying a curing agent to the conductive gel (step 312) to transform the liquid state of the conductive gel to a solid state.

In one embodiment, the form of step 304 may be one or more component of the conductive pad having a non-planar shape, such as, for example, the electrode element **124*a*, the conductive support layer 144*a*, the support layer 172*a*, the second removable protection layer 176*a***.

In one embodiment, spraying liquid conductive gel onto the non-planar form (step 308) may be performed by a person or may be performed by a conductive gel application system. The liquid conductive gel is conductive gel having a liquid state. In one embodiment, the liquid conductive gel may be applied to a substantially uniform thickness to the non-planar form.

In one embodiment, the step of applying a curing agent to the liquid conductive gel (step 312) may include exposing the liquid conductive gel to a UV light source, such exposure curing the liquid conductive gel. Curing the liquid conductive gel sprayed onto the non-planar form causes the liquid conductive gel to cure with a texture and/or shape that when applied to a patient, forms one or more air-channel 228 between the patient engaging surface 280 and the patient 276 such as those shown above in FIGS. 10-14.

In one embodiment, the cured conductive gel of step 312 is configured to mate with the conductive gel element 128 and/or one or more conductive gel layer 168.

In one embodiment, the process 300 for forming the conductive gel element of the present disclosure does not include step 304. In such an embodiment, performing the step of spraying liquid conductive gel onto a non-planar form (step 308) is instead performed by spraying liquid conductive gel to varying thicknesses with or without the non-planar form. In one embodiment, liquid conductive gel sprayed to varying thickness without the non-planar form may require performing step 312, applying a curing agent to the conductive gel, before the varying thickness levels to a substantially uniform thickness.

In one embodiment, the process 300 for forming the conductive gel element **128*a* of the present disclosure includes forming a first conductive gel layer, such as conductive gel layer 168*a* of conductive pad 220, and forming the conductive gel regions 224 of a desired thickness in a spaced apart manner on the conductive gel layer 168*a*** thereby providing a patient engaging surface having a plurality of wall portions forming an air-channel between each adjacently disposed pair of wall portions in accordance with the present disclosure.

The following is a number list of non-limiting illustrative embodiments of the inventive concept of the third mode disclosed herein:

35. A system, comprising:
- a generator configured to generate an electrical signal having an alternating current waveform at a frequency in a range from 50 kHz to 500 kHz;
- a first conductive lead electrically coupled to the generator, the first conductive lead configured to carry the electrical signal;
- a first conductive pad having a first electrode element electrically coupled to a first conductive gel element to supply electrical current to the first conductive gel element, wherein the first electrode element is electrically coupled to the first conductive lead, and the first conductive gel element is configured to be in contact with a patient's skin, the first conductive gel element having one or more first air-channel;
- a second conductive lead electrically coupled to the generator, the second conductive lead configured to carry the electrical signal; and
- a second conductive pad having a second electrode element electrically coupled to a second conductive gel element to supply electrical current to the second conductive gel element, wherein the second electrode element is electrically coupled to the second conductive lead, and the second conductive gel element is configured to be in contact with a patient's skin, the second conductive gel element having one or more second air-channel.

36. The system of illustrative embodiment 35, wherein the first conductive gel element is formed of a first conductive gel layer and a second conductive gel layer, the second conductive gel layer being formed of two or more non-intersecting conductive gel regions, and wherein the first air-channel is formed by spacing between the one or more non-intersecting conductive gel regions.

37. The system of illustrative embodiment 35, wherein the first electrode element has one or more first ridge and first groove that when coupled to the first conductive gel element form one or more second ridge and second groove on the first conductive gel element, and wherein the first air-channel is formed between the second groove and the patient's skin.

38. The system of illustrative embodiment 35, wherein the first conductive gel element comprises a first conductive gel layer, a support layer, and a second conductive gel layer, the support layer having one or more ridge and groove forming the first air-channel is between the second conductive gel layer and the patient's skin.

39. The system of illustrative embodiment 35, wherein the first conductive pad further comprises a protection layer attached to the first conductive gel layer, the protection layer having one or more ridge and groove causing the first conductive gel layer to form the first air-channel between the first conductive gel layer and the patient's skin.

40. A conductive pad, comprising:

a topcoat layer;

an electrode element connected to the topcoat layer, and configured to receive an electrical signal from a generator producing an electric signal as a TTField; and a conductive gel element electrically coupled to the electrode element so as to receive an electrical current from the electrode element, the conductive gel element configured to be in contact with a patient's skin and having one or more air-channel.

41. A method, comprising:

applying at least two conductive regions to a patient, the conductive regions being coupled to a generator, the generator configured to generate an electrical signal having an alternating current waveform at frequencies in the range from 50 kHz to 500 kHz, each conductive region having an electrode element electrically coupled with a conductive gel element so as to supply an electrical current from the electrode element to the conductive gel element, the electrode elements being electrically coupled to the generator and, upon receiving the electrical signal supplies electrical current to the conductive gel element, the conductive gel element being in contact with a patient's skin and having one or more air-channel; and activating the generator to supply the electrical signal to the electrode elements, thereby supplying electrical current to the patient through the conductive gel element.

Fourth Mode: Air-Channel with Shaping Member

A fourth mode of the present disclosure includes a system and method of implementing the system, the system comprising a generator configured to generate an electrical signal having an alternating current waveform at a frequency in a range from 50 kHz to 576 kHz; a first conductive lead electrically coupled to the generator, the first conductive lead configured to carry the electrical signal; a first conductive pad having a first electrode element electrically coupled to a first conductive gel element to supply electrical current to the first conductive gel element, wherein the first electrode element is electrically coupled to the first conductive lead, and the first conductive gel element is configured to be in contact with a patient's skin, the first conductive gel element having one or more first air-channel; a second conductive lead electrically coupled to the generator, the second conductive lead configured to carry the electrical signal; and a second conductive pad having a second electrode element electrically coupled to a second conductive gel element to supply electrical current to the second conductive gel element, wherein the second electrode element is electrically coupled to the second conductive lead, and the second conductive gel element is configured to be in contact with a patient's skin, the second conductive gel element having one or more second air-channel. The one or more first air-channel and/or the one or more second air-channel may be formed via insertion of one or more shaping member into the first conductive gel element and/or second conductive gel element with the first conductive gel element and second conductive gel element in a partially cured state, respectively.

Figure 16:
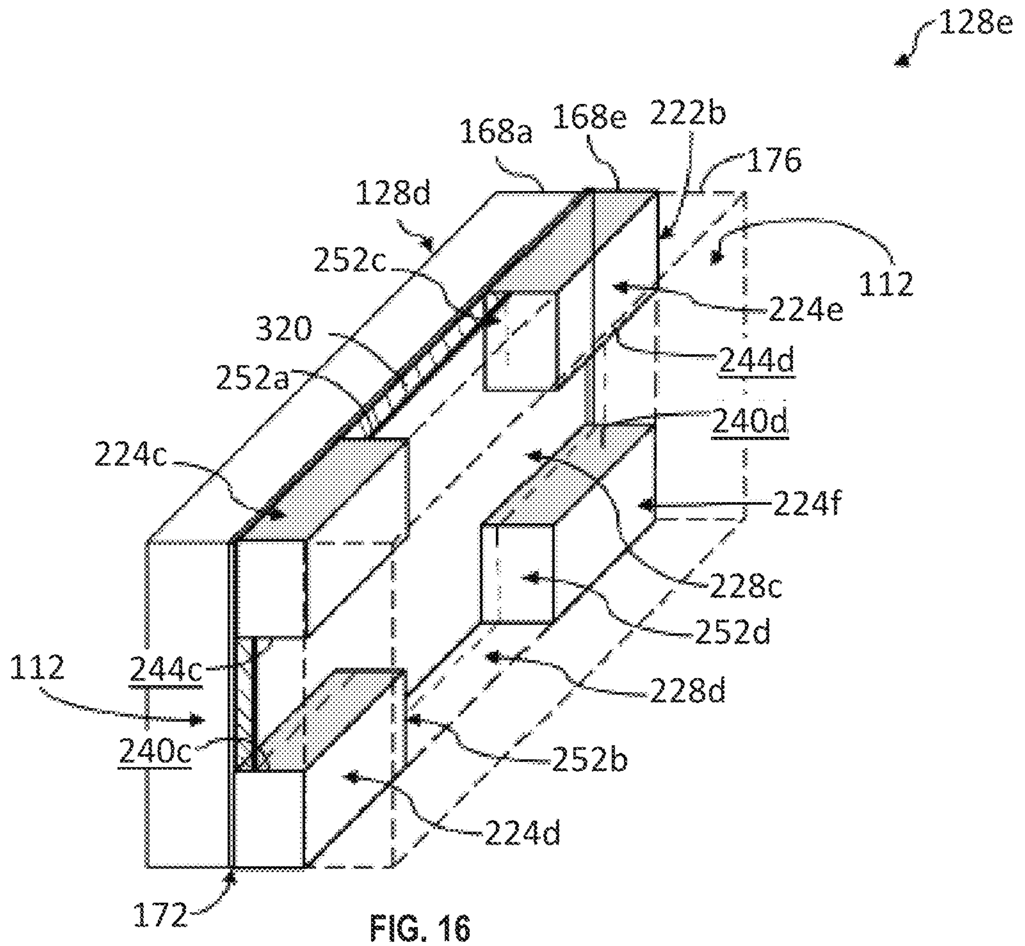
FIG. 16 is a perspective view of another exemplary embodiment of a portion of the conductive gel element and the second removeable protection layer of the conductive pad of FIG. 10 in which the conductive gel element is shaped by an insertion of a shaping member into the conductive gel element in a partially cured state.

Referring now to FIG. 16, shown therein is a perspective view of another exemplary embodiment of a portion of a conductive gel element 128*e* and the second removeable protection layer 176 of the conductive pad 220 of FIG. 10. The conductive pad 220 is an exemplary embodiment of the pad 70*a* and the pad 70*b*. Shown therein is the conductive gel layer 168*a*, bonded to support layer 172, which is in turn bonded to the conductive gel layer 168*e*. The support layer 172 is optional. In some embodiments, the conductive gel layer 168*e* is bonded directly to the conductive gel layer 168*a*.

Figure 17:
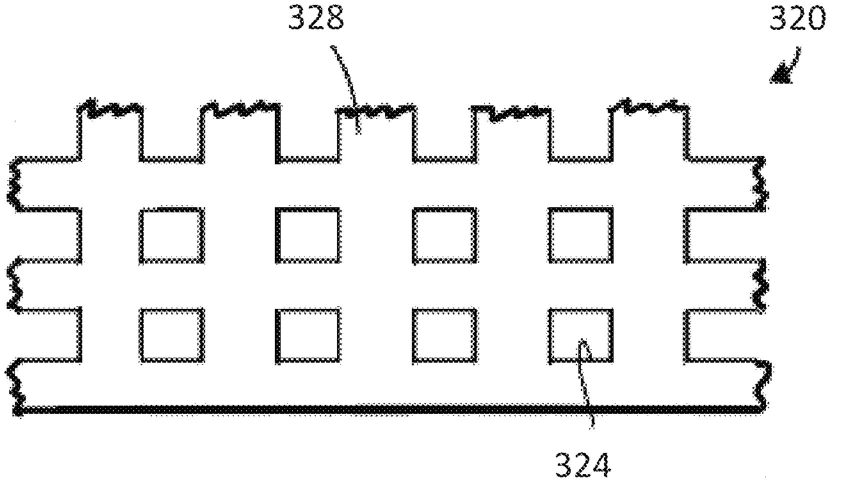
FIG. 17 is a top plan view of an exemplary shaping member constructed in accordance with the present invention.

Referring to FIGS. 16 and 17, the conductive gel layer 168*e* may be comprised of one or more conductive gel region 224 and one or more air-channel 228 formed by one or more shaping member 320. Generally, the one or more conductive gel region 224 of the conductive gel layer 168*e* may provide bulk electron transport agent configured to provide a source of free ions therein to enable electrical conductivity. The one or more air-channel 228 may provide fluid circulation (e.g., air circulation on skin).

Generally, the conductive gel layer 168*e* may be formed by the shaping member 320 while the conductive gel element 128*e* is in a partially cured state. At least a portion of the conductive gel element 128*e* in the partially cured state may be extruded through the shaping member 320 to create the one or more conductive gel regions 224, also referred to herein as spatially disposed protrusions, and one or more air-channel 228 adjacent to the shaping member 320 and in between an adjacently disposed pair of protrusions. In some embodiments, the shaping member 320 may remain within the conductive gel element 128*e* and form a component of the conductive pad 220. In some embodiments, the shaping member 320 may provide enhanced structural integrity to the conductive gel element 128*e*. For example, the shaping member 320 may be constructed of a flexible nylon mesh material that helps to prevent separation of the conductive gel element 128*e*. Once the shaping member 320 is placed into the conductive gel layer 168*e*, the conductive gel element 128*e* may be further cured forming the conductive gel layer 168*e* having a plurality of conductive gel regions 224 and one or more air-channel 228.

Figure 18:
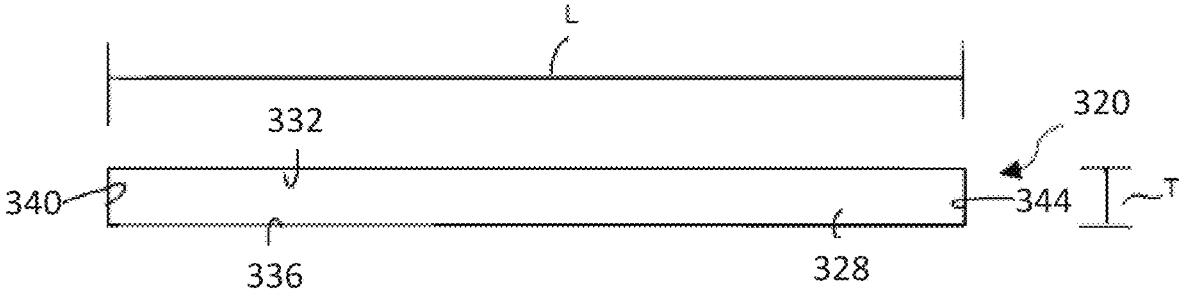
FIG. 18 is a side elevation view of the exemplary shaping member of FIG. 17.

Referring to FIGS. 17 and 18, generally, the shaping member 320 may include one or more aperture 324 within a mold 328. The mold 328 may be a matrix configured to give shape to the partially cured conductive gel element 128*e*, such as, for the formation of the one or more conductive gel regions 224 and/or the one or more air-channel 228. In some embodiments, the mold 328 may be formed of non-conductive material, such as a polymeric material. The one or more aperture 324 formed within the mold 328 may be any size or shape including, but not limited to, square, triangle, circle, or any fanciful shape. In some embodiments, differently sized and shaped apertures 324 may be provided within the same mold 328. In some embodiments, similarly sized and shaped apertures 324 may be provided within the same mold 328. In some embodiments, design considerations of the one or more aperture 324 may depend on size and shape of the desired air-channel 228 and/or the size and shape of the one or more conductive gel regions 224. In some embodiments, the shaping member 320 may include a plurality of apertures 324 such that extruding the conductive gel element 128*e* in the partially cured state through the one or more aperture 324 may extrude a plurality of conductive gel regions 224 (i.e., protrusions), for example. In some embodiments, the apertures 324 can have a length and/or width within a range from 0.105 mm (140 mesh) to 0.420 mm (40 mesh), for example.

Referring to FIGS. 16 and 18, the one or more mold 328 has a first side 332 and a second side 336. In some embodiments, the first side 332 may be positioned adjacent to the support layer 172 within the conductive gel element 128*e*. In some embodiments, the first side 332 may be positioned adjacent to the conductive gel layer 168*a* within the conductive gel element 128*e*. The second side 336 of the mold 328 may be adjacent to and open to the air-channels 228. The second side 336 of the shaping member 320 may be exposed to the one or more air-channel 228 without any intervening structure between the second side 336 of the shaping member 320 and the one or more air-channel 228. The second side 336 may form a boundary of the one or more air-channel 228 without any intervening structure between the second side 336 of the shaping member 320 and the one or more air-channel 228.

Thickness T between the first side 332 and the second side 336 of the mold 328 may be within a range from 0.01 mm to 3 mm. In some embodiments, the thickness T between the first side 332 and the second side 336 of the mold 328 may be designed to provide adequate air flow within the air-channels 228, for example. The one or more mold 328 has a first end 340 and a second end 344. In some embodiments, the mold 328 may extend from the first end 340 and the second end 344 in a length L approximate to the length of the conductive gel element 128*e*. In some embodiments, the length L of the mold 328 extending from the first end 340 to the second end 344 may be a portion of the length of the conductive gel element 128*e*.

Referring to FIGS. 16-18, the design and disposition of the one or more shaping member 320 may be any design configured to provide the one or more air-channel 228 while enabling electrical conductivity via the conductive gel regions 224. For example, in some embodiments, the shaping member 320 may be comprised of a lattice structure configured to provide the plurality of spatially disposed conductive gel regions 224 which may be arranged in a grid pattern similar to conductive gel layer 168*d* in FIG. 12. To that end, the conductive gel regions 224 include the first conductive gel region 224*c*, the second conductive gel region 224*d*, the third conductive gel region 224*e*, and the fourth conductive gel region 224*f*, each conductive gel region 224*c*-*f* is adjacent to another conductive gel region 224 and spatially disposed to form the first air-channel 228*c*, between the first conductive gel region 224*c* and the second conductive gel region 224*d* and extending between the third conductive gel region 224*e* and the fourth conductive gel region 224*f*, and the second air-channel 228*d*, between the first conductive gel region 224*c* and the third conductive gel region 224*e* and extending between the second conductive gel region 224*d* and the fourth conductive gel region 224*f*. The shaping member 320 may remain integral within the conductive gel layer 168*e* with the second side 336 of the shaping member 320 adjacent to the air-channels 228.

Figure 19:
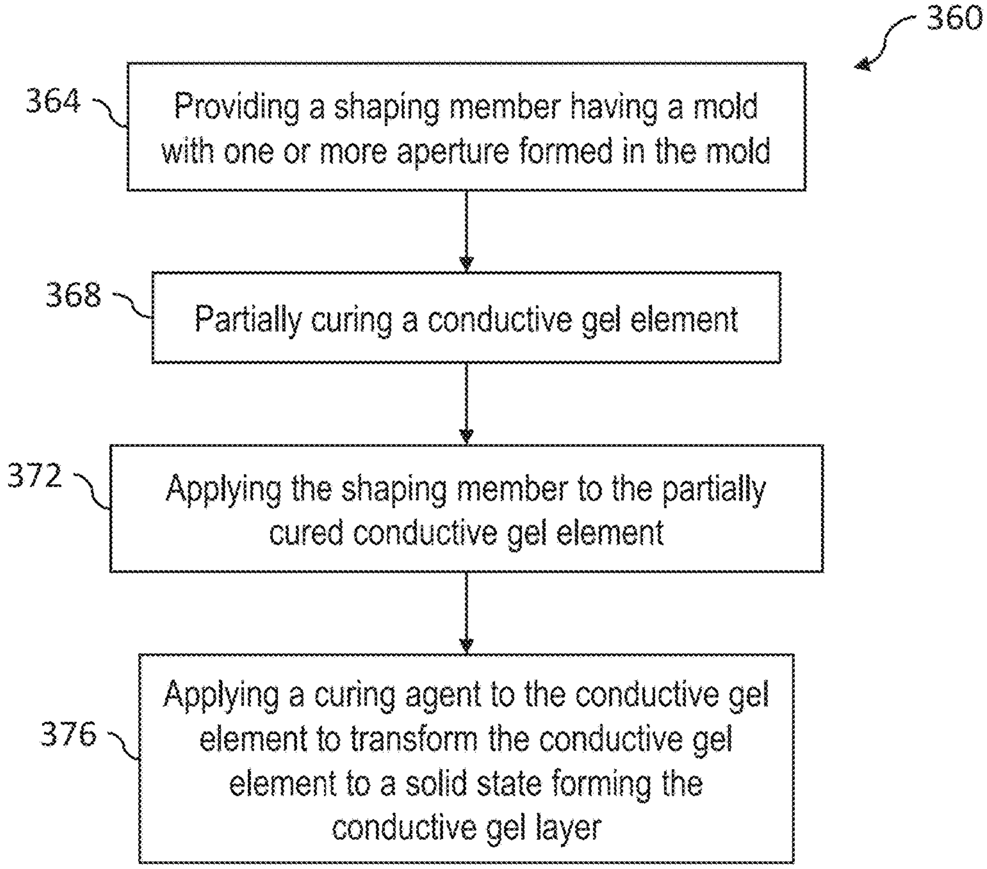
FIG. 19 is a process flow diagram of an exemplary embodiment of a process for forming a conductive gel element using the shaping member of the present disclosure.

FIG. 19 is a process flow diagram of an exemplary embodiment of a process 360 for forming the conductive gel layer 168*e* using the shaping member 320 of the present disclosure. The process 360 for forming the conductive gel layer 168*e* using the shaping member 320 generally comprises the steps of providing the shaping member 320 having the mold 328 and one or more aperture 324 formed in the mold 328, partially curing the conductive gel element 128*e*, applying the shaping member 320 to the partially cured conductive gel element 128*e*, and applying a curing agent to the conductive gel element 128*e* to transform the partially cured state of the conductive gel element 128*e* to a solid state.

In a step 364, the shaping member 320 may be provided and/or formed having the mold 328 with one or more aperture 324 formed in the mold 328. For example, the shaping member 320 may be a non-conductive screen, such as a nylon screen.

In a step 368, the conductive gel element 128*e* may be partially cured such as by providing a first predetermined amount of a curing agent, e.g., ultraviolet light, to the conductive gel element 128*e*.

In a step 372, the shaping member 320 may be applied to the partially cured conductive gel element 128*e* such that at least a portion of the partially cured conductive gel element 128*e* is extruded through the one or more aperture 324 of the shaping member 320.

In a step 376, a second predetermined amount of the curing agent may be applied to the conductive gel element 128*e* to transform the partially cured state of the conductive gel element 128*e* to a solid state forming the conductive gel layer 168*e* connected to and supporting encapsulating the shaping member 320, and being formed by the shaping member 320 into the one or more conductive gel region 224 and one or more air-channel 228.

Figure 20:
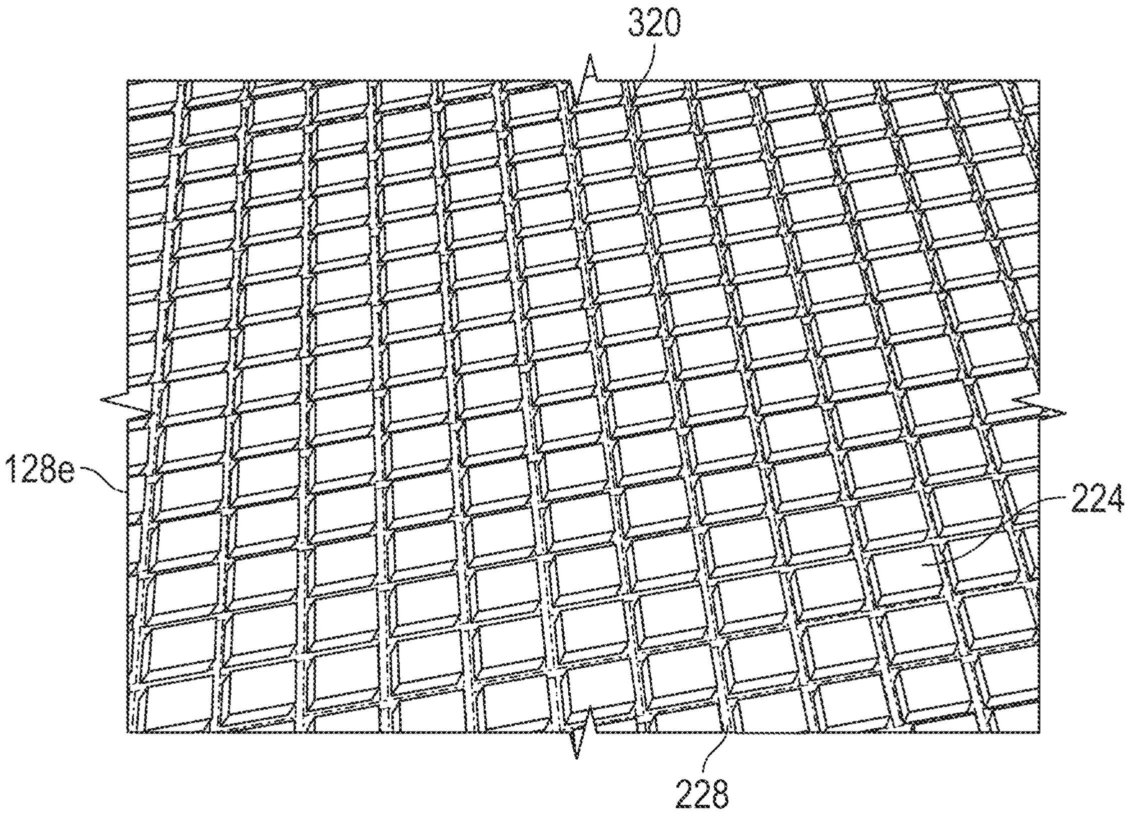
FIG. 20 is a perspective view of a portion of one embodiment of a conductive gel element shaped into a plurality of conductive gel regions or projections surrounded by air-channels by insertion of a shaping member, i.e., screen, into the conductive gel element.

FIG. 20 is a perspective view of a portion of the conductive gel element 128*e* shaped into a plurality of conductive gel regions 224. All of the conductive gel regions 224 are surrounded by the air-channels 228, with the exception of the conductive gel regions 224 bordering the edges of the conductive gel element 128*e*. As discussed above, the conductive gel regions 224 are formed by the insertion of the shaping member 320 into the conductive gel element 128*e* in a partially cured state.

The following is a number list of non-limiting illustrative embodiments of the inventive concept of the fourth mode disclosed herein:

42. A system, comprising:

a generator configured to generate an electrical signal having an alternating current waveform at a frequency in a range from 50 kHz to 500 kHz;

a first conductive lead electrically coupled to the generator, the first conductive lead configured to carry the electrical signal;

a first conductive pad having a first electrode element electrically coupled to a first conductive gel element to supply electrical current to the first conductive gel element, wherein the first electrode element is electrically coupled to the first conductive lead, and the first conductive gel element is configured to be in contact with a patient's skin, the first conductive gel element having a first conductive gel layer formed of a first shaping member and one or more first air-channel;

a second conductive lead electrically coupled to the generator, the second conductive lead configured to carry the electrical signal; and a second conductive pad having a second electrode element electrically coupled to a second conductive gel element to supply electrical current to the second conductive gel element, wherein the second electrode element is electrically coupled to the second conductive lead, and the second conductive gel element is configured to be in contact with a patient's skin, the second conductive gel element having one or more second air-channel.

43. The system of illustrative embodiment 42, wherein the first conductive gel layer has at least one protrusion configured to enable electrical conductivity.

44. The system of illustrative embodiment 43, wherein the first shaping member is a mold having a plurality of apertures formed in the mold.

45. The system of illustrative embodiment 44, wherein the apertures are positioned in the mold in a lattice pattern.

46. The system of illustrative embodiment 44, wherein the plurality of apertures in the mold of the first shaping member are configured to form protrusions and the one or more first air-channel in the first conductive gel layer.

47. The system of illustrative embodiment 42, wherein the first shaping member is integral with the first conductive gel element.

48. A conductive pad, comprising:

a topcoat layer;

an electrode element connected to the topcoat layer, and configured to receive an electrical signal from a generator producing an electric signal as a TTField; and a conductive gel element electrically coupled to the electrode element so as to receive an electrical current from the electrode element, the conductive gel element configured to be in contact with a patient's skin, the conductive gel element including a conductive gel layer and a shaping member, the shaping member positioned within the conductive gel layer and having a first side and a second side, wherein the conductive gel layer includes a plurality of protrusions and one or more air-channel on the second side of the shaping member.

49. The conductive pad of illustrative embodiment 48, wherein the shaping member includes a mold having a plurality of apertures.

50. The conductive pad of illustrative embodiment 48, wherein the shaping member is formed of a non-conductive material.

51. The conductive pad of illustrative embodiment 48, wherein the shaping member is formed of a mesh.

52. The conductive pad of illustrative embodiment 51, wherein the mesh is a polymeric material mesh.

53. The conductive pad of illustrative embodiment 52, wherein the polymeric material mesh is nylon mesh.

54. The conductive pad of illustrative embodiment 48, wherein the second side of the shaping member is open to the one or more air-channel.

55. The conductive pad of illustrative embodiment 48, wherein the second side of the shaping member is exposed to the one or more air-channel.

56. The conductive pad of illustrative embodiment 55, wherein the second side of the shaping member is exposed to the one or more air-channel without any intervening structure between the second side of the shaping member and the one or more air-channel.

57. The conductive pad of illustrative embodiment 55, wherein the second side of the shaping member defines a boundary of the one or more air-channel without any intervening structure between the second side of the shaping member and the one or more air-channel.

58. A method, comprising:

applying at least two conductive regions to a patient, the conductive regions being coupled to a generator, the generator configured to generate an electrical signal having an alternating current waveform at frequencies in a range from 50 kHz to 500 kHz, each conductive region having an electrode element electrically coupled with a conductive gel element so as to supply an electrical current from the electrode element to the conductive gel element, the electrode elements being electrically coupled to the generator and, upon receiving the electrical signal supplies electrical current to the conductive gel element, the conductive gel element being in contact with a patient's skin and having a conductive layer supporting a shaping member adjacent to one or more air-channel adjacent to the patient's skin; and activating the generator to supply the electrical signal to the electrode elements, thereby supplying electrical current to the patient through the conductive gel element.

Fifth Mode: Conductive Pad Made with Conductive Fabric

A fifth mode of the present disclosure includes a system for generating a TTField utilizing at least one conductive pad wherein the system comprises a generator configured to generate an electrical signal; a first lead coupled to the generator and a first conductive pad and configured to carry the electrical signal; the first conductive pad has a first electrode element comprising a first conductive fabric to supply electrical current to a patient; a second lead coupled to the generator and a second conductive pad and configured to carry the electrical signal; and the second conductive pad having a second electrode element comprising a second conductive fabric to supply electrical current to the patient.

Figure 21:
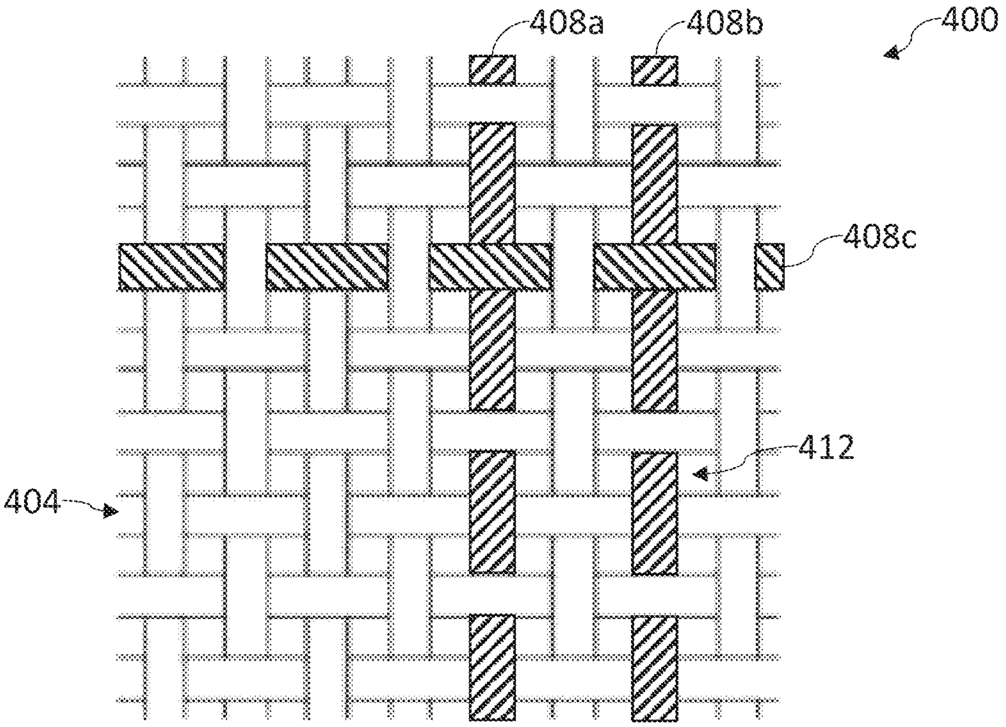
FIG. 21 is a top plan view of a conductive fabric constructed in accordance with the present disclosure.

Referring now to FIG. 21, shown therein is a top view of an exemplary embodiment of a conductive fabric 400 constructed in accordance with the present disclosure. Generally, the conductive fabric 400 comprises nonconductive threads 404 connected to one or more conductive thread 408*a-n*. For example, the nonconductive threads 404 can be interwoven with the one or more conductive thread 408*a-n* shown in FIG. 21 as conductive thread 408*a*, conductive thread 408*b*, and conductive thread 408*c*. Each of the conductive threads 408*a-n* can be woven with the nonconductive threads 404. In one embodiment, the conductive threads 408*a-n* extend across the conductive fabric 400 so as to create a substantially continuous conductive region across the conductive fabric 400. The conductive fabric 400 may include a plurality of perforations 412, which may be formed by a space between adjacently disposed nonconductive threads 404 and/or conductive threads 408 of the conductive fabric 400.

The nonconductive threads 404 and the conductive threads 408 can be connected together in a woven format or a non-woven format. In the non-woven format, the nonconductive threads 404 and the conductive threads 408 can be bonded together by entangling the nonconductive threads 404 and the conductive threads 408 mechanically, thermally or chemically. The nonconductive threads 404 and the conductive threads may be bonded together in a manner so that the conductive fabric 400 is flat or tufted. The conductive fabric 400 may be constructed of any type of fabric having conductive threads 408 and optionally nonconductive threads 404, such as woven fabric, non-woven fabric, or knit fabric, or any combination thereof.

In one embodiment, material for the nonconductive threads 404 may be selected from any non-conductive material having desirable properties such as, but not limited to, strong biocompatibility and low reactivity with other layers or components of conductive pad 100*f* shown in FIG. 22 and FIG. 23 and discussed in more detail below. In one embodiment, the conductive fabric 400 has an adhesive property such that the conductive fabric 400 has a propensity to, when placed at a particular location on a patient, stay at that particular location. In some embodiments, the conductive fabric 400 is sized to fit tightly and in an encircling, and form fitting manner onto a portion of the patient's body so as to maintain electrical conductivity between the conductive fabric 400 and the patient's skin. The conductive fabric 400 can be formed into a configuration suitable for use as tight-fitting garment or a brace. For example, the conductive fabric 400 can be formed into a tubular configuration and used as a knee brace which surrounds the patient's knee when the conductive fabric 400 is placed onto the patient's knee. In another embodiment, the conductive fabric 400 can be formed into a belt-like configuration having an attachment mechanism on one end, (e.g., buckle, Velcro or the like), suitable for use as a back brace.

In one embodiment, the conductive thread 408 may be constructed of a conductive material able to be bonded to and/or woven with the nonconductive threads 404 and able to withstand multiple distortions without compromising conductivity along the conductive thread 408. For example, the conductive thread 408 may be selected from any conductive material having desirable properties such as, but not limited to, high conductivity, strong biocompatibility, and low reactivity with other layers or components of the conductive pad 100*f*. In one embodiment, the conductive thread 408 is selected from a conductive material made from, bonded with, or coated with one or more of silver, tin, aluminum, titanium, platinum, carbon, an alloy thereof, and/or some combination thereof. In one embodiment, the conductive thread 408 is of a thickness sufficient to support conductivity of a voltage and an amperage suitable to generate TTFields and sufficient to cause flexible contouring of the conductive fabric 400.

FIG. 21 depicts three conductive threads 408*a-c*; however, it is understood that the number of conductive threads 408 within the conductive fabric 400 could be greater than or lesser than three. Further, while the conductive threads 408*a-n* are shown as being substantially evenly, spatially disposed within the conductive fabric 400 along with non-conductive threads, it is understood that the conductive threads 408*a-n* may be threaded, sewn, or otherwise disposed between non-conductive threads of the conductive fabric 400. In one embodiment, the conductive fabric 400 does not include the nonconductive threads 404.

Figure 22:
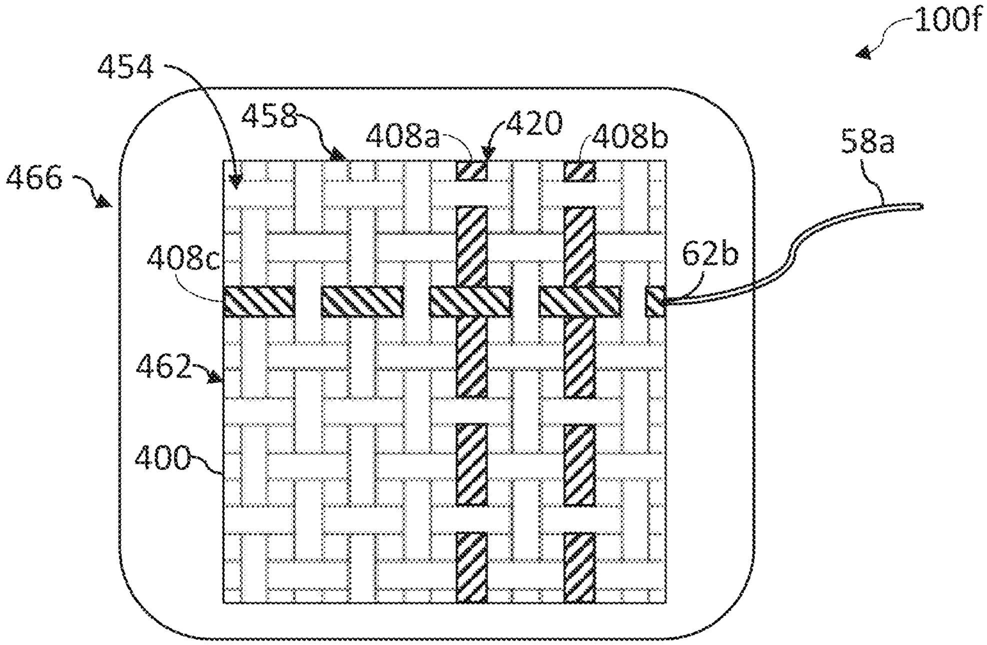
FIG. 22 is a top plan view of a first conductive pad constructed in accordance with the present disclosure.

Referring now to FIG. 22, shown therein is a top plan view of the conductive pad 100*f*. The conductive pad 100*f* is an exemplary embodiment of the pad 70*a* and the pad 70*b*. The conductive pad 100*f* may also be referred to as an electrode, such as the first electrode 18*a* or the second electrode 18*b*, or as an electrode pad. The conductive pad 100*f* may be provided with an electrode element 420, a top 450 (shown in FIG. 23), a bottom 454, an outer peripheral edge 458, and a conductive region 462 bounded by the outer peripheral edge 458. The conductive pad 100*f* may also be provided with a fabric support element 466 connected to the electrode element 420. The fabric support element 466 may extend beyond the outer peripheral edge 458. The electrode element 420 is formed, at least in part, of the conductive fabric 400. The conductive fabric 400 shown as part of the conductive pad 100*f* includes the conductive threads 408*a-c*. As shown, the conductive fabric 400 is connected to the second end 62*b* of the conductive lead 58*a*.

The conductive pad 100*f* is constructed so as to have sufficient flexibility so as to be able to conform to a portion of the patient, such as a portion of the patient's head, the patient's knee, or the like. The conductive pad 100*f* may also be constructed so that the conductive region 462 is continuous, and extends to the outer peripheral edge 458. In the example shown, the conductive fabric 400 of the conductive pad 100*f* is provided with a rectangular shape. However, it should be understood that the conductive fabric 400 of the conductive pad 100*f* can be provided with any type of shape such as a polygon, circle, or fanciful shape. Further, the conductive fabric 400 of the conductive pad 100*f* may be constructed so as to be cut and/or shaped at a point of use so as to be custom fitted for a particular part of a particular patient.

In one embodiment, the fabric support element 466, and/or conductive fabric 400 of the conductive pad 100*f* may be provided with the shape of an article of clothing. In some embodiments, the fabric support element 466 and/or the conductive fabric 400 is sized to fit tightly and in an encircling, and form fitting manner onto a portion of the patient's body so as to maintain electrical conductivity between the conductive fabric 400 and the patient's skin. The fabric support element 466 and/or the conductive fabric 400 can be formed into a configuration suitable for use as tight-fitting garment or a brace. For example, the fabric support element 466 and/or the conductive fabric 400 can be formed into a tubular configuration and used as a knee brace which surrounds the patient's knee when the conductive fabric 400 is placed onto the patient's knee.

In another embodiment, the fabric support element 466 and/or the conductive fabric 400 can be formed into a belt-like configuration having an attachment mechanism on one end, (e.g., buckle, Velcro or the like), suitable for use as a back brace. Non-limiting examples of articles of clothing formed by the fabric support element 466 and/or the conductive fabric 400 of the conductive pad 100*f* may include a hat, a shirt, a singlet, an undergarment, a brassiere, or any other form-fitting garment. In one embodiment, the conductive fabric 400 of the conductive pad 100*f* provided with the shape of an article of clothing, would lend itself to a surface area contoured to fit tight to a particular location on the patient's body and provide a substantial therapeutic benefit.

In one embodiment, the conductive fabric 400 of the conductive pad 100*f* may be constructed such that it may be formed into clothing for a particular patient. For example, the conductive fabric 400 of the conductive pad 100*f* may be constructed such that a tailor or seamstress, for example, can contour the conductive pad 100*f* for the particular patient. In one embodiment, the conductive fabric 400 of the conductive pad 100*f* formed into an article of clothing may be formed such that the conductive fabric 400 of the conductive pad 100*f* is held in place at a particular location on the patient by the form of the conductive fabric 400 or the fabric support element 466. For example, the form and/or size of the conductive fabric 400 may cause pressure to be exerted against the patient's skin where the patient's skin comes in contact with the conductive fabric 400.

In one embodiment, a surface area of the conductive fabric 400 is adjusted by the user such that operation of the conductive pad 100*f* does not exceed a comfortability threshold. In one embodiment, the comfortability threshold is a temperature at which a patient would be made uncomfortable while using the conductive pad 100*f*. In one embodiment, the comfortability threshold is a temperature at or about 40 degrees Celsius. In one embodiment, the comfortability threshold is a time before onset of maceration of a portion of the patient's skin in contact with the conductive pad 100*f*. In one embodiment, construction of the nonconductive threads 404 may be selected based on a comfortability threshold determined by a patient's tolerance for a texture of the nonconductive threads 404. For example, the non-conductive threads 404 may be constructed such that the texture is pleasant for a user. In one embodiment, the non-conductive threads 404 may be constructed of a fabric with the texture similar to that of silk.

In one embodiment, the fabric support element 466 and/or the conductive fabric 400 is constructed to exhibit flexible contouring such that when the conductive fabric 400 is placed on a patient's skin, the conductive fabric substantially conforms to contours of a portion of the patient's body.

Figure 23:
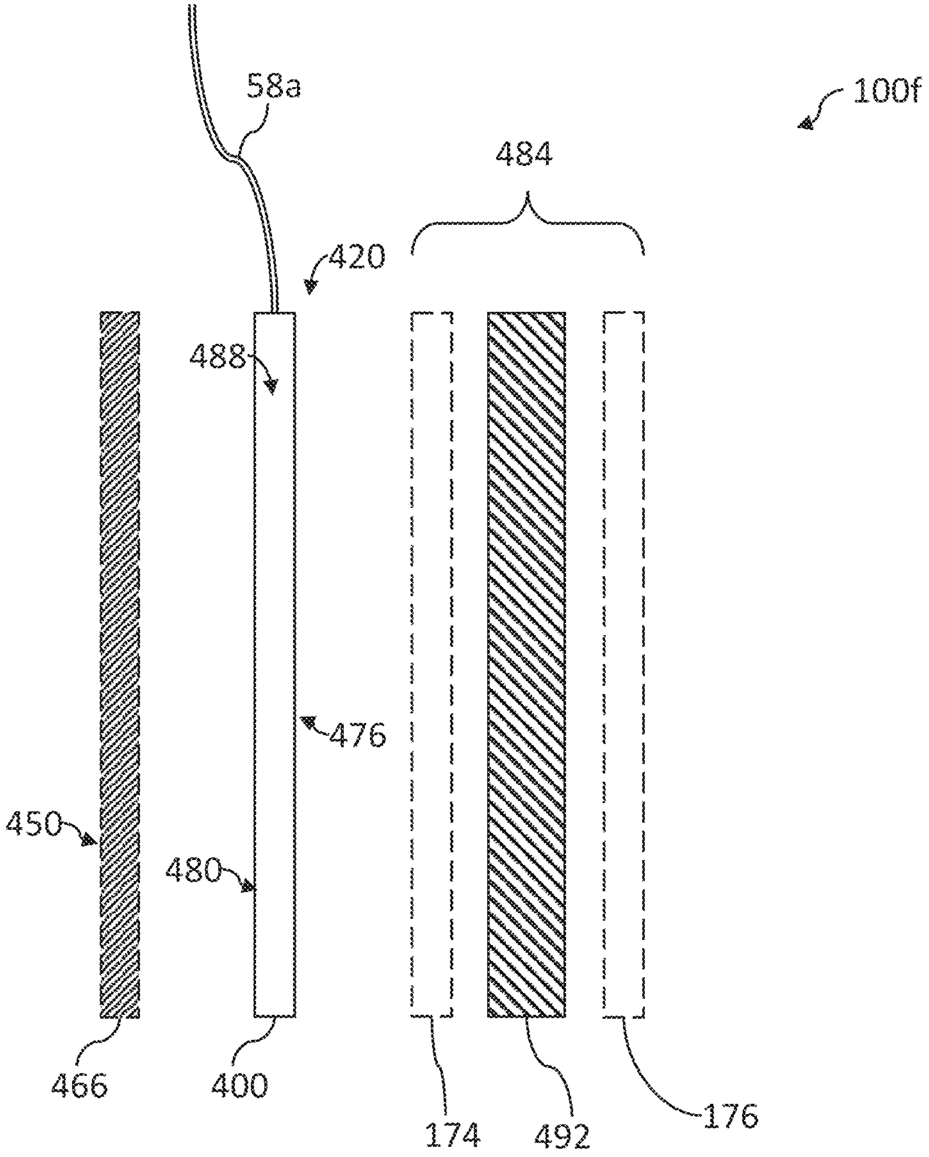
FIG. 23 is an exploded side view of an exemplary embodiment of the first conductive pad depicted in FIG. 22.

Referring now to FIG. 23, shown therein is an exploded side view of one embodiment of the conductive pad 100*f* constructed in accordance with the present disclosure. The conductive pad 100*f* generally comprises the conductive fabric 400 having a first side 476 disposed towards the patient's body and a second side 480 disposed away from the patient's body. In one embodiment, the conductive pad 100*f* further comprises a fabric support element 466 disposed on the second side 480 of the conductive fabric 400.

In another embodiment, the conductive pad 100*f* further comprises a conductive gel element 484. In one embodiment, the conductive gel element 484 is disposed on the first side 476 of the conductive fabric 400 whereas in another embodiment the conductive gel element 484 is disposed on the second side 480 of the conductive fabric 400 and may be passed through the conductive fabric 400 to form at least one region of the conductive gel element 484 on the first side 476.

In one embodiment, the conductive pad 100*f* does not include a dielectric layer electrically isolating the conductive fabric 400 from the conductive gel element 484. The conductive fabric 400 having the fabric support element 466 or the conductive gel element 484, or both, may be bonded together to form a composite structure that has the sufficiently flexible qualities discussed above. In some embodiments, the conductive fabric 400 is electrically coupled to the conductive gel element 484 so as to supply an electrical current from the conductive fabric 400 to the conductive gel element 484.

The conductive fabric 400 includes an outer peripheral edge 488. In one embodiment wherein the conductive fabric 400 includes the fabric support element 466 or the conductive gel element 484, or both, the fabric support element 466 or the conductive gel element 484, or both may extend beyond the outer peripheral edge 488 of the conductive fabric 400.

In one embodiment, the nonconductive threads 404 are woven or non-woven threads. The nonconductive threads 404 may provide a safe handling surface of the conductive fabric 400.

In some embodiments, the conductive fabric 400 is colored to match or approximate skin color of the patient. The conductive fabric 400 may be considered "breathable", that is, the conductive fabric 400 may have one or more perforation 412 and preferably has many distributed perforations 412, or the like, extending through the conductive fabric 400. In one embodiment, the one or more perforation 412 enables air-flow through the conductive fabric 400. The one or more perforation 412 may have the same or different dimension(s) as one or more other perforation 412, as well as the same or different shape as one or more other perforation 412. The one or more perforation 412 may be formed by a space between adjacently disposed threads of the conductive fabric 400.

In one embodiment, a thickness of the conductive fabric 400 may be determined based on the current and the frequency of the electric signal used to generate the TTField. The thickness may also be set based on other desirable properties such as heat dissipation and/or flexibility requirements of the conductive pad 100*f*, for example. For example, if the thickness is too thin, the patient may experience hot spots, that is, the patient may experience portions of the conductive pad 100*f* heating more rapidly than other portions of the conductive pad 100*f*, which may be due, at least in part, to the thickness slowing thermal conductivity, thus causing an increase in temperature differentials across the conductive pad 100*f*. In one embodiment, the thickness is between 25 mil and 75 mil.

In one embodiment, the conductive gel element 484 includes one or more conductive gel layer 492 having a bulk electron transport agent providing a source of free ions therein to enable electrical conductivity. In one embodiment, the one or more conductive gel layer 492 is formed primarily of a conductive gel or a semi-solid conductive gel. In the embodiment depicted in FIG. 23, the conductive gel element 484 includes the conductive gel layer 492. When present, the source of free ions in the gel may be any salt or other substance that serves as a source of free ions that are capable of floating substantially freely within the gel, wherein the free ions serve to conduct electricity and thus reduce impedance. In one embodiment, the conductive gel layer 492 includes a polymeric hydrogel. In one embodiment, the conductive gel layer 492 has adhesive properties, thus the conductive pad 100*f*, having the conductive fabric 400 bonded to the conductive gel layer 492, when placed at a particular location on the patient has a tendency to remain at that particular location. In one embodiment, the conductive gel element 484 is used in conjunction with the conductive fabric 400 to increase contact and increase conductivity between the conductive fabric 400 and the patient's skin. In one embodiment, the conductive gel element 484 is operable to reduce impedance between the conductive fabric 400 and the patient's skin.

In one or more embodiment, the conductive gel layer 492 may be sprayed onto either the conductive fabric 400 or a first removeable protection layer 174 in a liquid state. In such an embodiment, the one or more conductive gel layer 492 may be cured to a solid state having a uniform thickness (i.e., within manufacturing tolerances) to have a shape covering an entirety of the conductive fabric. In some embodiments, the conductive gel layer 492 may mimic the shape of the conductive fabric 400 or the first removeable protection layer 174.

After the conductive gel layer 492 is applied, then the conductive gel layer 492 may be exposed to an environment (e.g., UV light) causing the conductive gel layer 492 to set. In some embodiments, the conductive gel layer 492 may be applied directly to the first side 476 of the conductive fabric 400 in a predetermined pattern covering first regions of the first side 476 and not covering second regions of the first side 476 so that when the conductive pad 100*f* is applied to the patient's skin, the patient's skin is contacted by the conductive gel layer 492 in the first regions, and the patient's skin is exposed to the conductive fabric 400 in the second regions.

The bulk electron transport agent(s) may be any substance that is capable of enhancing the electrical and/or thermal conductivity of the conductive gel. In certain non-limiting embodiments, the bulk electron transport agent(s) includes one or more ionic compounds, one or more metals, or one or more non-metals, as well as any combinations thereof. In certain non-limiting embodiments, the bulk electron transport agent comprises an amorphous carbon and/or a crystalline carbon. Particular (but non-limiting) examples of bulk electron transport agents that may be utilized in accordance with the present disclosure include carbon black (e.g., as described above), graphene, and graphite.

In one embodiment, the conductive gel element 484 and/or the conductive gel layer 492 are formed primarily of a conductive gel or semi-solid conductive gel such as described above. The conductive gel element 484 may be in any form that allows the conductive pad **100*f* to function in accordance with the present disclosure. The exact thickness of the conductive gel element 484 is not important so long as the conductive gel element 484 is of sufficient thickness that the conductive gel element 484 does not dry out during the treatment. Preferably, the conductive gel element 484 has high conductivity, is tacky, and is biocompatible for extended periods of time. One suitable gel is AG603 Hydrogel, which is available from AmGel Technologies, 1667 S. Mission Road, Fallbrook, Calif. 92028-4115, USA. The conductive gel element 166 taught therein may be used with modified hydrogels (which includes not only perforations 412** but also recesses, protrusions, etc.) such as those described in U.S. Patent Application 63/020,636 filed May 6, 2020 entitled "CONDUCTIVE GEL COMPOSITIONS COMPRISING BULK ELECTRON TRANSPORT AGENTS AND METHODS OF PRODUCTION AND USE THEREOF" the entire content of which is hereby incorporated by reference in its entirety.

In one embodiment, the conductive gel element 484 is separate from the conductive pad **100*f*. When the conductive gel element 484 is separate from the conductive pad 100*f*, the conductive gel element 484 may have the first removeable protection layer 174 covering at least a portion of the conductive gel layer 492 that, when removed, such as by the user, allows the user to attach the conductive gel layer 492 to the conductive pad 100*f*, and more specifically, to either the first side 476 or the second side 480 of the conductive fabric 400. Additionally, the conductive gel element 484 may include a second removeable protection layer 500 covering at least a portion of the conductive gel layer 492 that when removed, such as by the user, allows the user to attach the conductive gel layer 492** to the patient, such as to the patient's skin on or over the target area.

In one embodiment, the conductive gel element 484 may first be placed in position on the patient's skin, then the conductive fabric 400 may be placed over the conductive gel element 484 such that the first side 476 of the conductive fabric 400 is in contact with the conductive gel element 484. In such an embodiment, the conductive gel element 484 may cause a wetting of the conductive fabric 400. In such an embodiment, the impedance between the patient's skin and the conductive fabric 400 may be lower than an impedance of the conductive fabric 400 in direct contact with the patient's skin.

In one embodiment, the conductive gel element 484 is formed, at least in part, with liquid hydrogel. In such an embodiment, impedance between the conductive fabric 400 and the patient's skin may be even further lowered.

In one embodiment, the conductive gel element 484 is in contact with the second side 480 of the conductive fabric 400. In such an embodiment, an amount of conductive gel from the conductive gel layer 492 may pass through the one or more perforation 412 and contact the patient's skin and may aid in limiting or eliminating maceration of the patient's skin. In such an embodiment, the amount of hydrogel between the conductive fabric 400 and the patient's skin is minimized compared to an amount of conductive gel in the conductive gel layer 492. Further, by placing the conductive gel element 484 on the second side 480 of the conductive fabric 400, the conductive gel within the conductive gel layer 492 is extruded through the one or more perforation 412 thereby forming a plurality of protrusions with one or more air-channel between each adjacent pair of protrusions as described in U.S. Patent Application No. 63/061,316 entitled "CONDUCTIVE PAD WITH IMPROVED AIR FLOW AND METHODS OF PRODUCTION AND USE THEREOF" filed on Aug. 5, 2020 the entire content of which is hereby incorporated by reference in its entirety.

In one embodiment, the conductive pad **100*f* may be shaped at a point of use (e.g., with scissors) to correspond to the target area of the patient. For example only and not by way of limitation, the conductive pad 100*f* may be cut, or otherwise modified, to remove a portion of the conductive pad 100*f* in order to accommodate an ear wherein the portion removed would otherwise be over the ear. By doing so, better adhesion of the conductive pad 100*f* to the patient's head may be achieved as well as an increase in comfort of the patient. As another example, the conductive pad 100*f* may be cut or otherwise modified to fit around a joint of the patient, such as, and not limited to, cutting the conductive pad 100*f* that is placed on a patient's knee in a manner that would allow the patient to continue to use their knee while the conductive pad 100*f* is attached, or, further, use their knee while undergoing treatment from TTFields. Shaping of the conductive pad 100*f* can be pre-structured or the conductive pad 100*f* can be made sufficiently flexible so that shaping of the conductive pad 100*f* is readily achievable. One important consideration when modifying the conductive pad 100*f* is any cut through a conductive region such that a portion of the conductive pad 100*f* is electrically isolated from the remainder of the conductive pad 100*f*** may have adverse therapeutic consequences.

In one embodiment, the conductive pad **100*f* does not include the conductive gel element 484. In such an embodiment, the conductive pad 100*f* may be increased in size, thus increasing surface area of the conductive fabric 400 in contact with the patient's skin in order to lower impedance between the conductive fabric 400** and the patient's skin.

In one embodiment, the conductive gel element 484 may be placed on the conductive fabric 400 such that the conductive gel element 484 does not extend to the outer peripheral edge 488 of the conductive fabric 400. In another embodiment, more than one separate conductive gel element 484 may be placed on the conductive fabric 400. For example, the one or more conductive gel element 484 may be spatially disposed such that one or more air-channel is formed between adjacently disposed pairs of the conductive gel element 484.

In one embodiment, the fabric support element 466 is formed of a non-conductive material providing support and/or structure to the conductive fabric 400. In one embodiment, the fabric support element 466 is a non-woven, non-conductive material. The fabric support element 466 may provide a safe handling surface for the conductive pad 100*f* to electrically isolate the conductive fabric 400 from the top 450 of the conductive pad 100*f*. In some embodiments, the fabric support element 466 is colored to match or approximate skin color of the patient. The fabric support element 466 may be bonded to the second side 480 of the conductive fabric 400. In one embodiment, the fabric support element 466 may be "breathable", that is, the fabric support element 466 may include one or more perforation and preferably many distributed perforations or the like extending through the fabric support element 466 to enable air-flow to other layer(s) including but not limited to the conductive fabric 400. The perforation(s) may have the same or different dimension(s) as another perforation, as well as the same or different shape as the other perforation. In one embodiment, the fabric support element 466 may be sewn or otherwise mechanically, thermally or chemically coupled to the conductive fabric 400. In one embodiment, a non-conductive fabric may be used to attach the fabric support element 466 to the conductive fabric 400. In one embodiment, the fabric support element 466 is constructed, at least in part, by garment foam or garment padding.

Figure 24:
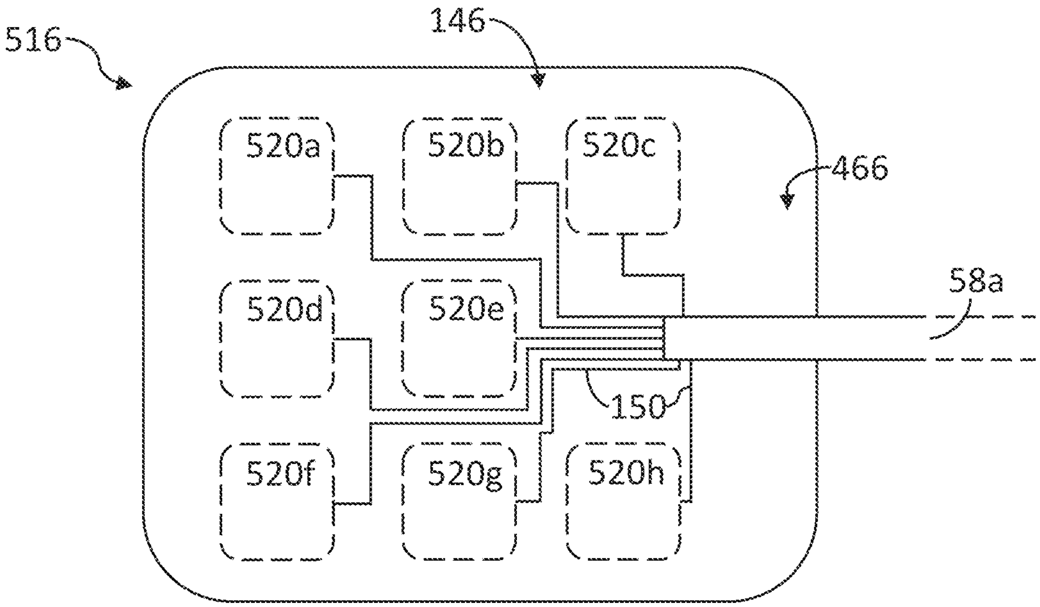
FIG. 24 is a bottom plan view of another exemplary embodiment of a conductive pad constructed in accordance with the present disclosure.

Referring to FIG. 24, shown therein is a functional diagram of an exemplary embodiment of a conductive pad 516. The conductive pad 516 is identical in construction and function as the conductive pad 100*f* described above, with the exception that the conductive fabric 400 and the conductive gel element 484 are arranged to form a plurality of conductive regions 520*a-h* of the conductive fabric 400 connected to a conductive lead 58*a*. Eight conductive regions 520*a-h* are shown in FIG. 24 by way of example. The conductive pad 516 includes the fabric support element 466 extending over and between the conductive regions 520*a-h*. In this embodiment, the fabric support element 466 may be formed of a non-conductive material, or be formed of an electrically conductive material that does not receive any electrical current from the conductive regions 520*a-h*. The conductive regions 520*a-h* are electrically isolated by one or more dielectric region 146 extending between each adjacently disposed pair of conductive regions 520*a-h*. The dielectric region 146 can be formed by interleaving a dielectric element laterally between each pair of adjacently disposed conductive regions 520*a-h*. The conductive lead 58*a* may include two or more isolated conductor 150 such that each conductive region 520*a-h* is coupled to the generator 54 independently, thus allowing the generator 54 to independently control the TTField generated by each conductive region 520*a-h*. In such an embodiment, the electronic apparatus 50 may alternate between one or more conductive region 520*a-h* of the conductive pad 516, thus creating and shaping TTFields with increased specificity and precision. A single conductive pad 516 having multiple conductive regions 520*a-h*, can be used as a substitute or in conjunction with the conductive pad 100*f*.

In one embodiment, the conductive pad 516 is formed in the shape of an article of clothing as described above in more detail. For example, the conductive pad 516 may be formed into a shirt having the plurality of conductive regions 520*a-h*. The plurality of conductive regions 520*a-h* may be selectively activated such that a TTField is generated to target a tumor at a particular location within the patient's abdomen or chest. Alternatively, the conductive pad 516 may be formed into a hat having the plurality of conductive regions 520*a-h*. The plurality of conductive regions 520*a-h* may be selectively activated such that a TTField is generated to target a tumor at a particular location within the patient's head.

In one embodiment, one or more conductive region 520 may be placed on the conductive gel element 484 such that each conductive region 520 is electrically isolated from each other conductive region 520. By way of example, a first conductive region 520 (e.g., the conductive region 520*a*) may be placed at a first position on a first conductive gel element 484 and a second conductive region 520 (e.g., the conductive region 520*b*) may be placed at a second position on a second conductive gel element 484. The first position and the second position may be disposed such that the first position and the second position do not overlap and are separate from each other such that the first conductive region 520 and the second conductive region 520 are electrically isolated from one another. In one embodiment, a ratio between the surface area of each conductive region 520 and a surface area of the combined conductive gel elements 484 is 50/50. In another embodiment, a ratio between the surface area of each conductive region 520 and a surface area of the combined conductive gel elements 484 is 70/30 respectively. In one embodiment, each conductive region 520 may have the same or a different shape. For example, the conductive region 520*a* may be a strip having a length greater than a width whereas the conductive region 520*b* may be substantially circular in shape.

In one embodiment, the generator 54, connected to the conductive pad 516, may supply a first electric signal having a first power and a first frequency to a first group of one or more conductive region 520*a-h* (e.g., conductive region 520*a* and conductive region 520*b*, for example) at a first instance in time to generate a first TTField. The generator 54, at a second instance in time, may supply a second electric signal having a second power, the same as or different from the first power, and a second frequency, the same as or different from the first frequency, to a second group of one or more conductive region 520*a-h* (e.g., conductive region 520*b* and conductive region 520*c*, for example) to generate a second TTField. The second group may include one or more conductive region 520*a-h* included in the first group, or may not include one or more conductive region 520*a-h* included in the first group. The first TTField and the second TTField may target the same target area or may target different target areas. In one embodiment, the first instance in time and the second instance in time may overlap, that is, the generator 54 may supply the second electric signal to the second group while also supplying the first electric signal to the first group. In such an embodiment, the first group and the second group may be mutually exclusive.

In one embodiment, the generator 54, connected to the conductive pad 516, may supply a first electrical signal having a first power and a first frequency to a first group of one or more conductive region 520*a-h* (e.g., conductive region 520*a* and conductive region 520*b*, for example) and supply a second electrical signal having a second power and a second frequency to a second group of one or more conductive region 520*a-h* (e.g., conductive region 520*b* and conductive region 520*c*, for example) at the same instance in time. That is, the generator 54, may simultaneously supply the first electric signal to the first group and the second electric signal to the second group. While the above embodiments describe only the first group and the second group, it is understood that there may be more than two groups. In one embodiment, the number of groups is dependent on the number of combinations of the conductive regions 520*a-h*.

In one embodiment, the generator 54 may be connected to the conductive pad 516 and another pad, such as the pad 70*b*. In such an embodiment, the generator 54 may supply the electric signal to the one or more conductive region 520*a-h* of the conductive pad 516. The one or more conductive region 520*a-h* receiving the electric signal may then generate a TTField between each of the one or more conductive region 520*a-h* of the conductive pad 516 and the pad 70*b*.

Certain non-limiting embodiments of the present disclosure are related to kits that include any of the components of the TTField generating systems, such as the electronic apparatus 50, described herein. In one embodiment, one or more of the conductive pad 100*f* may be packaged as part of a kit. In one embodiment, the kit may include the conductive pad 100*f* and the lead 58*a* connected to the conductive fabric 400. In another embodiment, the kit may include two conductive pads 100*f*, and the leads 58*a* and 58*b*. In each of the above embodiments, the lead 58*a* or 58*b* may be mechanically coupled to the conductive pads 100*f*, for example, by a rivet, by solder, by adhesive, by welding, or other electrically conductive coupling means. In each of the above embodiments, the kit may further include the blocking capacitor 82*a* or the blocking capacitor 82*b* positioned such that the electric signal passes through the blocking capacitor 82*a* or 64*b*. In each of the above embodiments, the conductive pad 100*f* may include the second removeable protection layer 500 attached to and covering at least a portion of (or the entire) the conductive gel element 484 such that the second removeable protection layer 500 protects the conductive gel element 484 from potential damage, such as loss of adhesion or disruption of or discontinuities. The second removeable protection layer 500 may be easily removed by the user before the conductive pad 100*f* and/or the second conductive pad 100*b* is applied to the patient. In one embodiment, the second removeable protection layer 500 is an electric insulator, such that the second removeable protection layer 500 prevents or substantially reduces accidental application of the electric signal before the conductive pad 100*f* and/or the second conductive pad 100*b* is attached to the patient. In each of the above embodiments, the kit may include more than the conductive pad 100*f* and the second conductive pad 100*b*, and may include a number of conductive pads (constructed in accordance with the present disclosure) that, when applied to the patient, have a therapeutic benefit. In addition, the kit can further include a set of written instructions explaining how to use one or more components of the kit. A kit of this nature can be used in any of the methods described or otherwise contemplated herein. In one embodiment, the conductive pad 516 may be used instead of either the conductive pad 100*f* or the second conductive pad 100*b*, or both, in the abovementioned kit.

Figure 25:
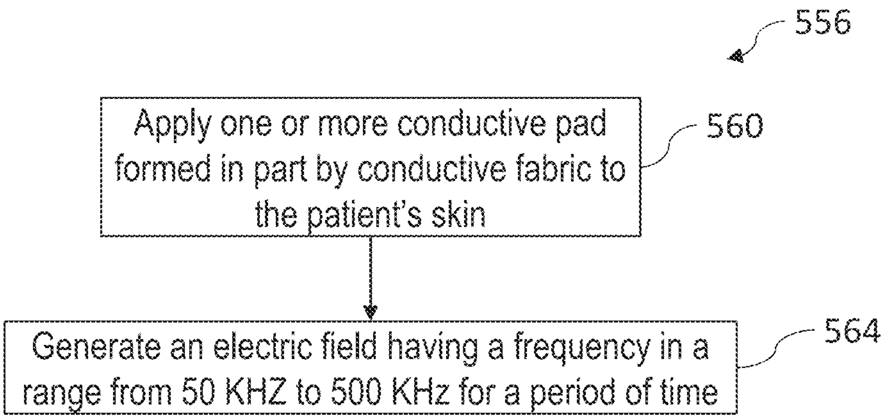
FIG. 25 is a process diagram of an exemplary embodiment of a process of treating a tumor utilizing the conductive pads of FIGS. 21-24.

Referring now to FIG. 25, shown therein is a process diagram of an exemplary embodiment of a process 556 of using the electronic apparatus 50 and the conductive pad 100*f* or the conductive pad 516 to apply a TTField to a patient. The process 556 generally comprises the steps of: applying one or more of the conductive pad(s) 100*f* to the patient's skin and/or the conductive pad 516 (step 560) and generating an alternating electric field having a frequency in a range of from about 50 kHz to about 576 kHz for a period of time (step 564). The process 556 will be described in relation to two of the conductive pads 100*f*, however, the conductive pad 516 may be used in replace of or in addition to the two conductive pads 100*f*.

The step of applying the two conductive pads 100*f* to the patient's skin (step 560) may be performed by the user. In one embodiment, before applying the conductive pads 100*f* to the patient's skin, the patient's skin may need to be cleaned (e.g., such as but not limited to, cleansing of the skin of foreign matter or biological matter and shaving of the skin, if necessary) to enable the conductive fabric 400 to adhere directly to the patient's skin. Or, the conductive fabric 400 can supply the TTF field to the patient through the conductive gel layer 492. In some embodiments, a liquid conductive gel may be applied directly to the patient's skin prior to application of the conductive fabric 400 to the patient's skin so that the liquid conductive gel enhances the conductivity between the conductive fabric 400 and the patient's skin.

The step of generating an alternating electric field (TTField) (step 564) may be performed by the generator 54 and may be instantiated by an operation performed by the user or control box 66. In one embodiment, step 564 may be performed more than one time and the period of time for which the step 564 is performed a first time may be the same as or different from the period of time for which the step 564 is performed a second time (or other period(s) of time beyond the second time).

In some embodiments, step 564 is only performed once before the process 556 is repeated. There may be a time period between each time the process 556 is repeated. Each time the process 556 is repeated, the time period may be the same as or different from the previous time period. Each time the process 556 is repeated, the conductive pads 100*f* may be placed in the same or a different position on the patient's skin.

During the process 556, applying the conductive pad 100*f*, the second conductive pad 100*b*, and/or the conductive pad 516 to the patient's skin (step 560) may result in the conductive pad 100*f*, the second conductive pad 100*b*, and/or the conductive pad 516 being attached to the patient's skin for an extended period of time.

The following is a number list of non-limiting illustrative embodiments of the inventive concept of the fifth mode disclosed herein:

59. A system, comprising:
- a generator configured to generate an electrical signal having an alternating current waveform at a frequency in a range from 50 kHz to 500 kHz;
- a first conductive lead electrically coupled to the generator, the first conductive lead configured to carry the electrical signal;
- a first conductive pad having a first conductive fabric electrically coupled to the first conductive lead;
- a second conductive lead electrically coupled to the generator, the second conductive lead configured to carry the electrical signal; and
- a second conductive pad having a second conductive fabric electrically coupled to the second conductive lead.

60. The system of illustrative embodiment 59, wherein the first conductive pad further comprises a first conductive gel element connected to the first conductive fabric, and configured to be placed in contact with a patient's skin.

61. The system of illustrative embodiment 59, wherein the first conductive fabric includes a first side to be disposed towards a patient's body, and wherein the first conductive gel element is connected to the first side of the first conductive fabric.

62. The system of illustrative embodiment 61, wherein the first conductive gel element is applied to the entirety of the first side of the first conductive fabric.

63. The system of illustrative embodiment 61, wherein the first conductive gel element covers a first region of the first side and does not cover a second region of the first side.

64. The system of illustrative embodiment 59, wherein the first conductive fabric includes non-conductive threads connected to conductive threads.

65. A conductive pad, comprising:

a topcoat layer constructed of a non-conductive material;

a conductive fabric having a first side and a second side, the second side connected to the topcoat layer, and configured to receive an electrical signal from a generator producing an electric signal as a TTField; and a conductive gel element connected to the first side of the conductive fabric and electrically coupled to the conductive fabric so as to receive an electrical current from the conductive fabric, the conductive gel element configured to be in contact with a patient's skin.

66. The conductive pad of illustrative embodiment 65, wherein the conductive gel element is applied to the entirety of the first side of the conductive fabric.

67. The conductive pad of illustrative embodiment 65, wherein the conductive gel element covers a first region of the first side and does not cover a second region of the first side.

68. The conductive pad of illustrative embodiment 65, wherein the conductive fabric includes non-conductive threads connected to conductive threads.

69. A method, comprising:

applying at least two conductive regions to a patient, the conductive regions being coupled to a generator, the generator configured to generate an electrical signal having an alternating current waveform at frequencies in the range from 50 kHz to 500 kHz, each conductive region having a conductive fabric supply an electrical current to the patient; and activating the generator to supply the electrical signal to the conductive fabric, thereby supplying electrical current to the patient through the conductive fabric.

70. The method of illustrative embodiment 69, wherein the conductive fabrics have a first side connected to respective conductive gel elements, and wherein the step of applying the at least two conductive regions to the patient includes applying the conductive gel elements to the patient.

71. A method of making a conductive pad, comprising:

applying a conductive gel element to at least one of a first side and a second side of a conductive fabric.

72. The method of illustrative embodiment 71, wherein applying the conductive gel element is defined further as applying the conductive gel element so as to cover a first region of the first side and to not cover a second region of the first side.

Sixth Mode: Conductive and Non-Conductive Pad with Perforations

A sixth mode of the present disclosure includes a conductive pad. The conductive pad has a topcoat layer, an electrode element and a conductive gel element. The electrode element is connected to the topcoat layer, and configured to receive an electrical signal from a generator producing an electric signal as a TTField. The conductive gel element is directly connected to the electrode element so as to receive an electrical current from the electrode element. The conductive gel element is configured to be in contact with a patient's skin. The electrode element and the conductive gel element can be constructed of a plurality of flexible films bonded together so as to provide the conductive pad with sufficient flexibility to conform to a patient's body.

Figure 26:
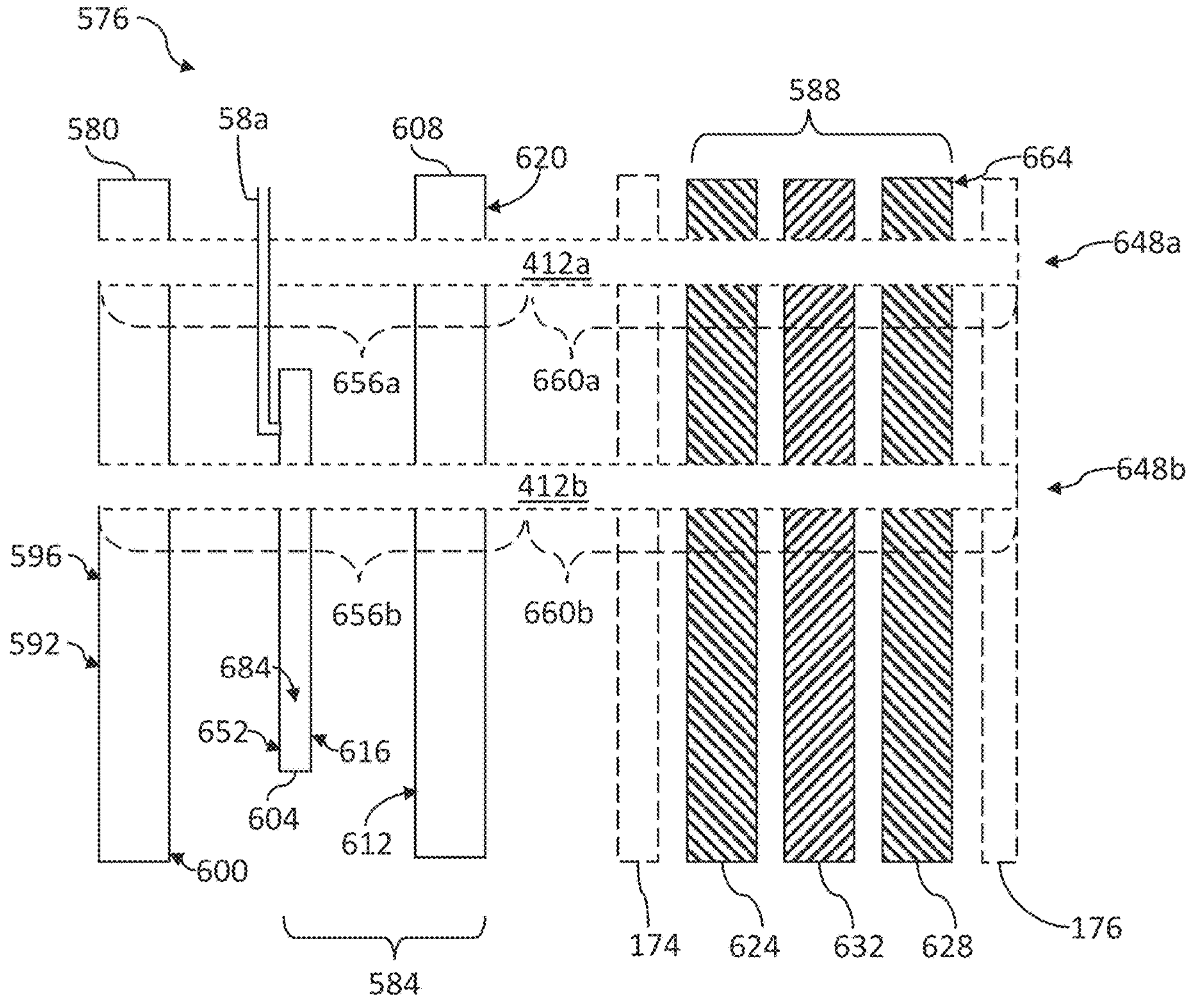
FIG. 26 is an exploded side view of another embodiment of a pad constructed in accordance with the present disclosure.

Referring now to FIG. 26, shown therein is an exploded side view of an exemplary embodiment of a pad 576 constructed in accordance with the present disclosure. The pad 576 is an exemplary embodiment of the first pad 70*a* and the second pad 70*b*. The pad 576 is provided with a durable topcoat layer 580, an electrode element 584, and a conductive gel element 588. Each of the durable topcoat layer 580, the electrode element 584, and the conductive gel element 588 may be constructed similarly to the durable topcoat layer 120, the electrode element 124, and the conductive gel element 128 except as disclosed below. The electrode element 584 is positioned between the durable topcoat layer 580 and the conductive gel element 588. The durable topcoat layer 580, the electrode element 584, and the conductive gel element 588 may be bonded together to form a composite structure that has the sufficiently flexible qualities discussed above. In some embodiments, the electrode element 584 is directly connected to, and electrically coupled to the conductive gel element 588 so as to supply an electrical current from the electrode element 584 to the conductive gel element 588. In this embodiment, the pad 576 does not include a dielectric layer electrically isolating the electrode element 584 from the conductive gel element 588.

The durable topcoat layer 580 may be formed similarly to the durable topcoat layer 120 as described above and includes a first surface 592 forming a top 596 of the pad 576 and a second surface 600 in contact with and bonded to an electrode layer 604 and a conductive support layer 608.

In one embodiment, the electrode layer 604 may be bonded to the conductive support layer 608. The conductive support layer 608 may include a first surface 612 attached to or otherwise coupled to a second surface 616 of the electrode layer 604 and a second surface 620 in direct contact with the conductive gel element 588. In some embodiments, an entirety of the second surface 620 is in direct contact with the conductive gel element 588. The conductive support layer 608 may be formed of a conductive carbon film configured to support the electrode layer 604 while also conductively coupling the electrode layer 604 to the conductive gel element 588. In one embodiment, the conductive support layer 608 may be electroplated, or otherwise bonded, to the electrode layer 604. In one embodiment, the conductive support layer 608 may surround and/or enclose the electrode layer 604.

The conductive gel element 588 includes a first conductive gel layer 624 and a second conductive gel layer 628 bonded to a support layer 632. In one embodiment, the first conductive gel layer 624 and the second conductive gel layer 628 include a polymeric hydrogel and may be constructed similarly to the conductive gel layers 168*a* and 168*b* respectively as described above. The support layer 632 may be constructed similarly to the support layer 172 as described above, of a woven or nonwoven material such as a material known as Reemay (spun nylon). The conductive gel element 588 may include a first removeable protection layer 174 and a second removeable protection layer 564 as described above.

The first removeable protection layer 174 permits the electrode element 584 and the conductive gel element 588 to be constructed separately and adhered together at a later time. The step of adhering the electrode element 584 to the conductive gel element 588 can be accomplished by the patient or healthcare provider at a point of care, or by a manufacturer of the pad 576.

As shown in FIG. 26, however, the pad 576 further includes one or more perforation 412 depicted as a first perforation 412*a* and a second perforation 412*b*. In one embodiment, the one or more perforation 412 may extend through at least a portion of the conductive gel element 588, the first removeable protection layer 174, the electrode element 584, and/or the durable topcoat layer 580. The one or more perforation 412 may be positioned such that air is capable of passing through the pad 576 to reach the patient's skin, thus forming one or more air-channel 648, e.g., air-channel 648*a* formed by the first perforation 412*a* and air-channel 648*b* formed by the second perforation 412*b*. The one or more perforation 412 extends through at least a portion of the conductive gel element 128, the first removeable protection layer 174, the electrode element 584, and/or the durable topcoat layer 580 to allow for an increased air flow to a patient's skin. The one or more air-channel 648, by facilitating increased air flow to the patient's skin, enables release of moisture on the patient's skin, reduces and/or eliminates macerations, lesions/ulcers, and dermatitis, as well as decreases operating temperature when the TTField is applied to the pad 576.

In addition, given prolonged exposure of the pad 576 to the patient's skin, the pad 576 should be optimized for use at body temperature (i.e., in a range of from about 34° C. to about 40° C.). At these temperatures, air flow introduced by the one or more perforation 412 maximizes evaporative cooling thereby allowing for a reduced operating temperature and cooling effect to the patient's skin.

In one embodiment, the one or more perforation 412 extends through one or more of the durable topcoat layer 580, the electrode layer 604, the conductive support layer 608, the first removeable protection layer 174, the first conductive gel layer 624, the support layer 632, the second conductive gel layer 628, and the second removeable protection layer 176, or some combination thereof. In one embodiment, the one or more perforation 412 extends from the second surface 620 through the conductive support layer 608 to the first surface 612. In an embodiment where the electrode layer 604 does not separate a portion of the conductive support layer 608 from the durable topcoat layer 580, the one or more perforation 412 may or may not extend through the durable topcoat layer 580, and the one or more perforation 412 may or may not be the perforations of the durable topcoat layer 580 as described above. In one embodiment, the one or more perforation 412 extending through the conductive support layer 608 may extend from the second surface 616 of the electrode layer 604 through the electrode layer 604 to a first surface 652 of the electrode layer 604. In one embodiment the one or more perforation 412 may extend from the second surface 600 of the durable topcoat layer 580 through the durable topcoat layer 580 to the first surface 592 of the durable topcoat layer 580. In this way, the one or more perforation 412 may extend from the second surface 620 of the conductive support layer 608 to the first surface 592 of the durable topcoat layer 580 thus providing one or more air-channel 648 allowing air to move from being in contact with the conductive gel element 588 through the top 596 of the durable topcoat layer 580 of the pad 576.

In one embodiment, the pad 576 the first perforation 412*a* extends through the conductive support layer 608 and the second perforation 412*b* extends through both the conductive support layer 608 and the electrode layer 604. In another embodiment, the pad 576 includes the first perforation 650*a* which extends through the conductive support layer 608 and the durable topcoat layer 580 where the durable topcoat layer 580 and the conductive support layer 608 are in contact with each other, and includes the second perforation 412*b* which extends through each of the conductive support layer 608, the electrode layer 604, and the durable topcoat layer 580.

In one embodiment, one or more perforation 412 includes a first portion 656 and a second portion 660. As shown in FIG. 26, the first perforation 412*a* includes a first portion 656*a* extending through the conductive support layer 608, of the electrode element 584, and the durable topcoat layer 580, and a second portion 660*a* extending through the conductive gel element 588. The second perforation 412*b* includes a first portion 656*b* extending through the conductive support layer 608 and the electrode layer 604, of the electrode element 584, and the durable topcoat layer 580, and a second portion 660*b* extending through the conductive gel element 588.

As shown in FIG. 26, the second portion 660*a* of the first perforation 412*a* and the second portion 660*b* of the second perforation 412*b* extend through the first removeable protection layer 174 and the second removeable protection layer 176. In another embodiment, however, the second portion 660*a* of the first perforation 412*a* and the second portion 660*b* of the second perforation 412*b* do not extend through the first removeable protection layer 174 and the second removeable protection layer 176.

In an embodiment where the pad 576 includes the first removeable protection layer 174, the user, after removing the first removeable protection layer 174, may align the first portion 656 with the second portion 660 of each perforation 412 such that each perforation 412 extends from the bottom 664 through the pad 576, (i.e., through the conductive gel element 588, through the electrode element 584, and through the durable topcoat layer 580), to the top 596. In one embodiment when the conductive gel element 588 comprises at least one liquid conductive gel element, the first portion 656 and the second portion 660 of each perforation 412 are not aligned, such that the liquid conductive gel element does not pass through the first portion 656, but is, instead, maintained within the conductive gel element 588. In one embodiment, the second portion, extending through the conductive gel element 588, may be described in the U.S. Patent Application 62/956,992 entitled "PERFORATED HYDROGEL CONFIGURATIONS AND METHODS OF PRODUCTION AND USE THEREOF" and/or described in the U.S. Patent Application 63/004,016 entitled "ASSEMBLIES CONTAINING TWO CONDUCTIVE GEL COMPOSITIONS AND METHODS OF PRODUCTION AND USE THEREOF" both of which are incorporated by reference in their entirety herein.

While shown in FIG. 26 as comprising the first perforation 412*a* and the second perforation 412*b* extending through the pad 576, a person having ordinary skill in the art should readily appreciate that the pad 576 may comprise any number of perforation 412 extending through one or more components of the conductive gel element 588, the first protection layer 560, the electrode element 584, and/or the durable topcoat layer 580 capable of accomplishing the presently disclosed and/or claimed inventive concept(s), including, without limitation, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 476, 425, 450, 576, 525, 550, 575, 676, 625, 650, 675, 776, 725, 750, 775, 876, 825, 850, 875, 976, 925, 950, 975, or greater than or equal to 1,000 perforation 412.

Figure 29:
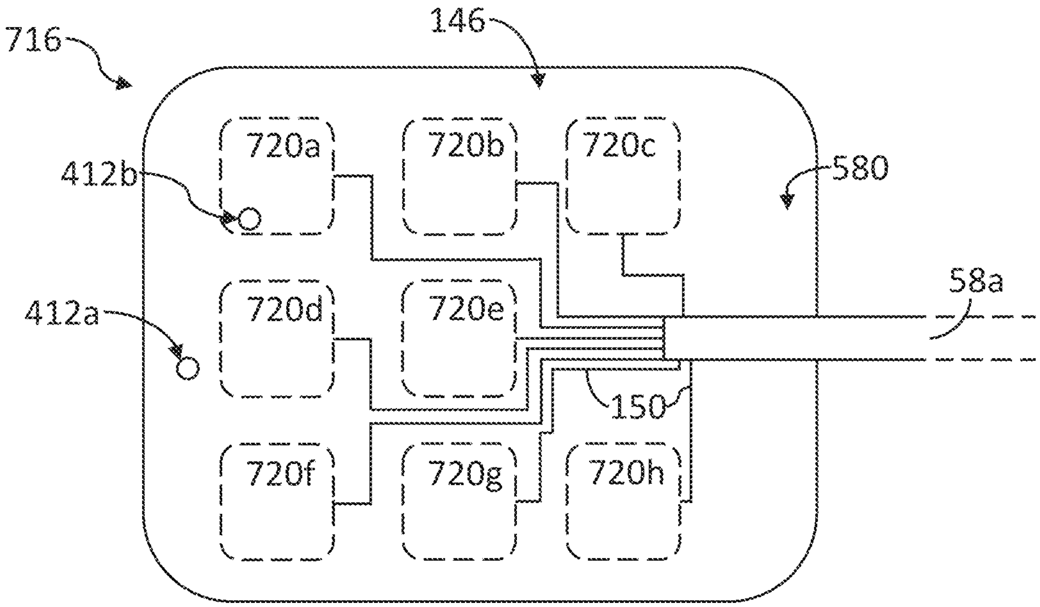
FIG. 29 is a perspective view of another exemplary embodiment of a pad constructed in accordance with the present disclosure.

Additionally, the one or more perforation 412 may have a shape, such as a circle, as shown in FIG. 29 below. A person having ordinary skill in the art, however, should readily understand that the one or more perforation 412 may be any shape capable of accomplishing the presently disclosed and/or claimed inventive concept(s), including, without limitation, circular, oval, triangular, square, rectangular, pentagonal, hexagonal, heptagonal, octagonal, nonagonal, decagonal, hendecagonal, dodecagonal, any shape with any number of sides capable of accomplishing the presently disclosed and/or claimed inventive concept(s), any portion of an aforementioned shape, or any combination thereof. In one embodiment, each of the one or more perforation 412 may have the same shape or a different shape.

The one or more perforation 412 may be of any dimension capable of accomplishing the presently disclosed and/or claimed inventive concept(s), including, without limitation, a dimension in which the distance across a particular perforation is 0.1 millimeter, 0.2 millimeter, 0.3 millimeter, 0.4 millimeter, 0.5 millimeter, 0.6 millimeter, 0.7 millimeter, 0.8 millimeter, 0.9 millimeter, 1.0 millimeter, 1.1 millimeter, 1.2 millimeter, 1.3 millimeter, 1.4 millimeter, 1.5 millimeter, 1.6 millimeter, 1.7 millimeter, 1.8 millimeter, 1.9 millimeter, 2.0 millimeters, 2.1 millimeters, 2.2 millimeters, 2.3 millimeters, 2.4 millimeters, 2.5 millimeters, 2.6 millimeters, 2.7 millimeters, 2.8 millimeters, 2.9 millimeters, 3.0 millimeters, 3.1 millimeters, 3.2 millimeters, 3.3 millimeters, 3.4 millimeters, or greater than or equal to 3.5 millimeters. In an embodiment where the pad 576 comprises more than one perforation 412, the perforation 412 may have the same or different dimension(s).

The one or more perforation 412 may be formed in and through the pad 576 via any technique capable of accomplishing the presently disclosed and/or claimed inventive concept(s), including, without limitation, via dye-cutting techniques and/or laser-cutting techniques. The formation of the one or more perforation 412 in and through the pad 576 may be accomplished via one or more automated or non-automated process or processes.

In one non-limiting embodiment, each or all of the one or more perforation 412 may be tapered wherein, for example, at least one perforation 412 has a first diameter extending through the bottom 664 and a second diameter extending through the top 596 wherein the first diameter and the second diameter are different. The term “diameter” as used herein means a straight line passing from side to side through the center of the perforation, and does not imply any particular cross-sectional shape of the perforation. Similarly, in another embodiment each or all of the one or more perforation 412 may be tapered wherein, for example, at least one perforation 412 has a first diameter extending through the second surface 620 and a second diameter extending through the first surface 652 or the first surface 612 wherein the first diameter and the second diameter are different.

Figure 27:
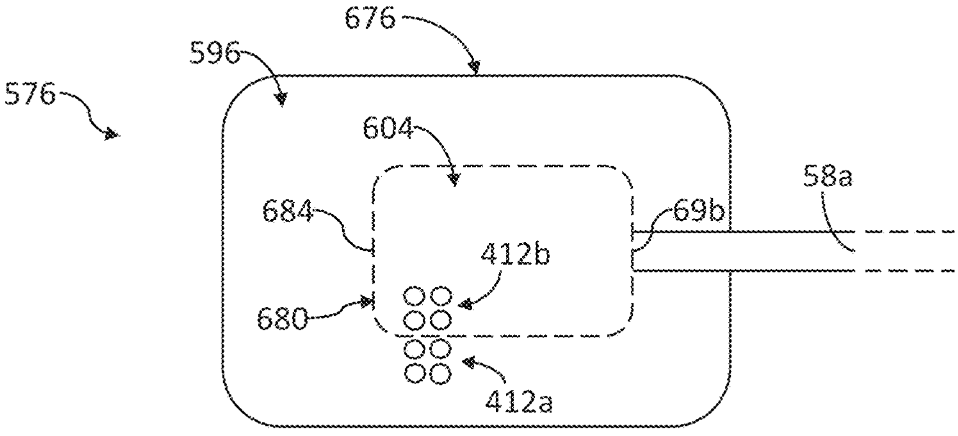
FIG. 27 is a top plan view of the pad of FIG. 26 constructed in accordance with the present disclosure.

Referring now to FIG. 27, shown therein is a diagram of a top plan view of an exemplary embodiment of the pad 576. The pad 576 may be provided with a top 596, a bottom 664 (shown in FIG. 26), an outer peripheral edge 676, and a conductive region 680 bounded by the outer peripheral edge 676. As shown, the pad 576 is connected to the second end 62*b* of the conductive lead 58*a*. The pad 576 is constructed so as to have sufficient flexibility so as to be able to conform to a portion of the patient, such as a portion of the patient’s head, the patient’s knee, or the like. In the example shown, the pad 576 is provided with a rectangular shape. However, it should be understood that the pad 576 can be provided with any type of shape such as a polygon, circle, or fanciful shape. Further, the pad 576 may be constructed so as to be cut and/or shaped at a point of use so as to be custom fitted for a particular part of a particular patient by constructing the pad 576 of a series of bonded flexible films, as discussed with respect to the first pad 100*a* and the second pad 100*b*. Further shown is the electrode layer 604, which includes outer peripheral electrode edge 608. The conductive support layer 608 may extend beyond the outer peripheral electrode edge 148*a* of the electrode layer 604. The pad 576 further includes one or more of perforation 412 and may include one or more first perforation 412*a* and one or more second perforation 412*b*. Each of the one or more first perforation 412*a* extends through the conductive support layer 608 but not the electrode layer 604, whereas each of the one or more second perforation 412*b* extends through the conductive support layer 608 and the electrode layer 604.

In one embodiment, the one or more perforation 412 may form a grid pattern, that is, each of the one or more perforation 412 may be substantially uniformly distanced from each other. In one embodiment, the one or more perforation 412 is substantially uniformly distanced from each other in a longitudinal direction along the top 596. In another embodiment, the one or more perforation 412 is substantially uniformly distanced from each other in a lateral direction along the top 596. In yet another embodiment, the one or more perforation 412 is substantially uniformly distanced from each other in both a longitudinal direction and in a lateral direction along the top 596 in a grid pattern. In another embodiment, the one or more perforation 412 are spatially disposed such that a distance between consecutive perforation 412 may be determined based at least in part on evaporative and/or air-flow properties needed for a particular application.

In one embodiment, the one or more perforation 412 may be spaced within the pad 576 forming a nine-by-nine grid for each square inch of the pad 576, that is, for each square inch of the durable topcoat layer 580 or the electrode element 584, the one or more perforation 412 form a nine-by-nine perforation grid comprising eighty-one (81) perforation 412 spatially disposed into nine (9) rows of nine (9) perforation 412. A person having ordinary skill in the art, however, should readily understand that the number of perforation 412 per square inch may be any number capable of accomplishing the presently disclosed and/or claimed inventive concept(s), including, without limitation, fewer than eighty-one perforation 412 per square inch and greater than eighty-one perforation 412 per square inch. The number of perforations 412 per square inch is limited by a size of each perforation 412, which is based at least in part on the diameter of each perforation 412, and the distance between each perforation 412.

Figure 28:
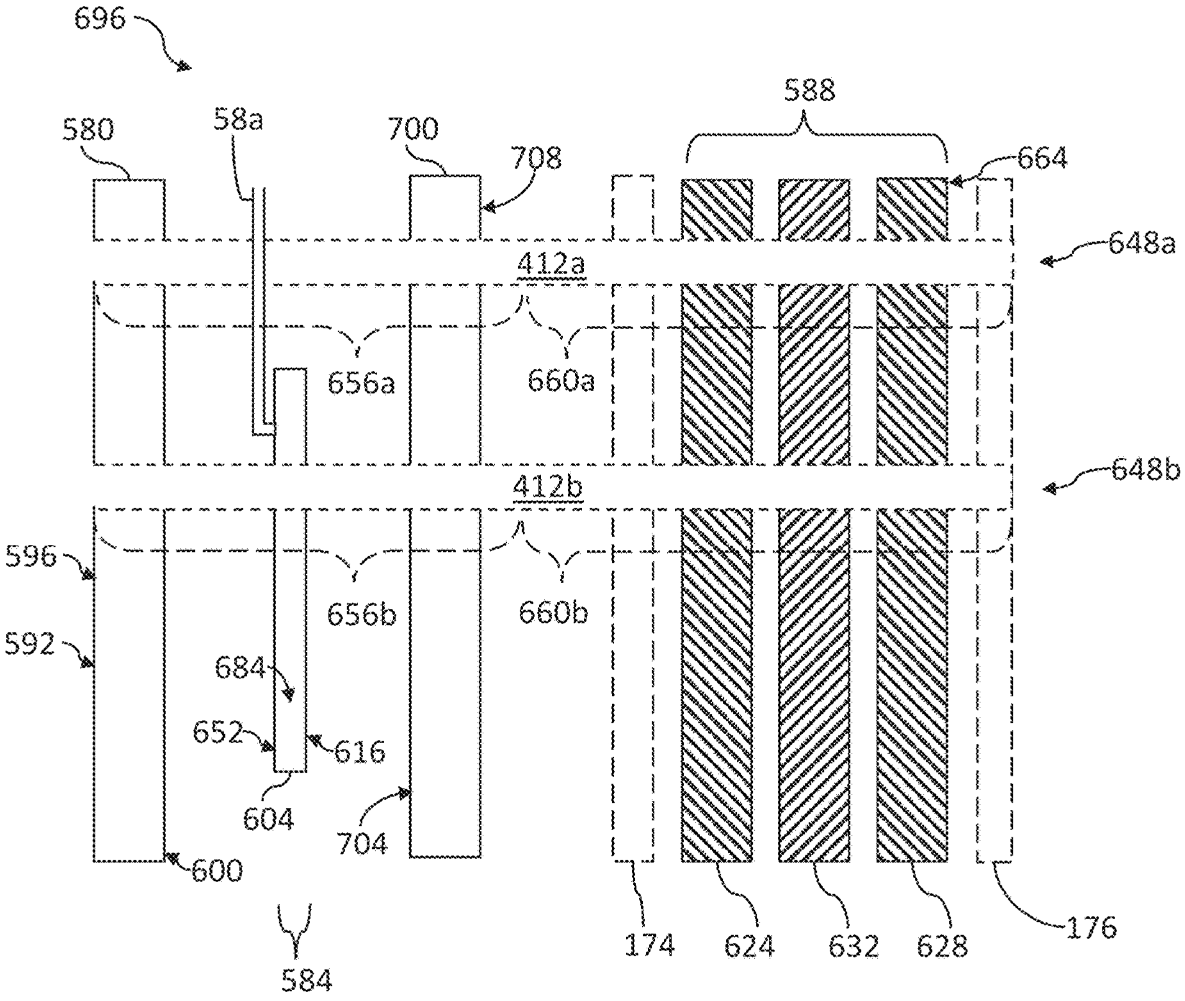
FIG. 28 is an exploded side view of another embodiment of a pad constructed in accordance with the present disclosure having a non-conductive flexible polymer layer electrically isolating an electrode element from a conductive gel element.

Referring to FIG. 28, shown therein is another embodiment of a pad 696 constructed in accordance with the present disclosure. The pad 696 is similar in construction and function to the pad 576 described above with respect to FIG. 26 and FIG. 27, with the exception that the conductive support layer 608 may be omitted, and a non-conductive, and a flexible polymer layer 700 is positioned between the electrode layer 604 and the conductive gel element 588. Elements common between the pad 576 and the pad 696 are labeled with common reference numerals. The flexible polymer layer 700 may be constructed of a dielectric material as discussed below. The flexible polymer layer 700 may be provided with a first surface 704, and a second surface 708. The first surface 704 may be attached to or otherwise coupled to the second surface 616 of the electrode layer 604 and the second surface 708 may be in direct contact with the conductive gel element 588. In some embodiments, an entirety of the first surface 704 is in direct contact with the second surface 616 of the electrode layer 604, and the second surface 708 is in direct contact with the conductive gel element 588.

The flexible polymer layer 700 is constructed of a dielectric material and functions as an insulator. In some preferred embodiment, the flexible polymer layer 700 comprises poly (vinylidene fluoride-trifluoroethylene-chlorotrifluoroethylene) and/or poly(vinylidene fluoride-trifluoroethylene-1-chlorofluoroethylene). Those two polymers are abbreviated herein as "Poly(VDF-TrFE-CtFE)" and "Poly(VDF-TrFE-CFE)", respectively. These embodiments are particularly advantageous because the dielectric constant of these materials is on the order of 40. Because the TTFields are capacitively coupled through the flexible polymer layer 700, and because capacitance is inversely proportional to the thickness of the flexible polymer layer 700, the flexible polymer layer 700 is preferably as thin as possible (e.g., less than 10 μm or less than 5 μm). On the other hand, the flexible polymer layer 700 should not be too thin because that could impair manufacturability, compromise the layer's structural integrity, and risk dielectric breakdown when the AC signals are applied. In some preferred embodiments, the flexible polymer layer 700 has a thickness that is at least 1 μm. In some preferred embodiments the flexible polymer layer 700 is between 1-3 μm thick (e.g., about 2 μm), which provides a good balance between the parameters noted above. Preferably, the thickness of the flexible polymer layer 700 is uniform. But in alternative embodiments, the thickness could be non-uniform.

Optionally, ceramic nanoparticles may be mixed into the Poly(VDF-TrFE-CtFE) and/or Poly(VDF-TrFE-CFE). Optionally, these ceramic nanoparticles may comprise at least one of barium titanate and barium strontium titanate.

In alternative embodiments, instead of forming the flexible polymer layer 700 from Poly(VDF-TrFE-CtFE) and/or Poly(VDF-TrFE-CFE), a different polymer that provides a high dielectric constant, and/or a high level of capacitance may be used. The requirements for these different polymers are as follows: (1) at least one frequency between 100 kHz and 576 kHz, the polymer layer has a dielectric constant of at least 20; (2) the flexible polymer layer 700 has a thickness of less than 20 microns in a direction perpendicular to the first surface 704 of the flexible polymer layer 700; and (3) the thickness of the flexible polymer layer 700 multiplied by its dielectric strength is at least 200 V. Example of alternative polymers that may be used in place of Poly(VDF-TrFE-CtFE) and/or Poly(VDF-TrFE-CFE) include the following: (1) ceramic nanoparticles mixed into at least one of Poly (VDF-TrFE), P(VDF-HFP), PVDF; and (2) barium titanate and/or barium strontium titanate ceramic nanoparticles mixed into at least one of Poly(VDF-TrFE), P(VDF-HFP), PVDF.

In some preferred embodiments, the thickness of the flexible polymer layer 700 is less than 10 μm, and in some preferred embodiments, the thickness of the flexible polymer layer 700 is less than 5 μm. In some preferred embodiments, the thickness of the flexible polymer layer 700 multiplied by its dielectric strength of at least 476 V. In some preferred embodiments, the flexible polymer layer 700 has a dielectric constant of at least 20 measured at 200 kHz.

As shown in FIG. 28, however, the pad 696 further includes one or more perforation 412 depicted as the first perforation 412*a* and the second perforation 412*b*. In one embodiment, the one or more perforation 412 may extend through at least a portion of the conductive gel element 128, the first removeable protection layer 174, the flexible polymer layer 700, the electrode element 584, and/or the durable topcoat layer 580. The one or more perforation 412 may be positioned such that air is capable of passing through the pad 696 to reach the patient's skin, thus forming one or more air-channel 582, e.g., air-channel 648*a* formed by the first perforation 412*a* and air-channel 648*b* formed by the second perforation 412*b*. The one or more perforation 412 extends through at least a portion of the conductive gel element 588, the first removeable protection layer 174, the flexible polymer layer 700, the electrode element 584, and/or the durable topcoat layer 580 to allow for an increased air flow to a patient's skin. The one or more air-channel 648, by facilitating increased air flow to the patient's skin, enables release of moisture on the patient's skin, reduces and/or eliminates macerations, lesions/ulcers, and dermatitis, as well as decreases operating temperature when the TTField is applied to the pad 696.

In addition, given prolonged exposure of the pad 696 to the patient's skin, the pad 696 should be optimized for use at body temperature (i.e., in a range of from about 34° C. to about 40° C.). At these temperatures, air flow introduced by the one or more perforation 412 maximizes evaporative cooling thereby allowing for a reduced operating temperature and cooling effect to the patient's skin.

In one embodiment, the one or more perforation 412 extends through one or more of the durable topcoat layer 580, the electrode layer 604, the flexible polymer layer 700, the first removeable protection layer 174, the first conductive gel layer 624, the support layer 632, the second conductive gel layer 628, and the second removeable protection layer 176, or some combination thereof. In one embodiment, the one or more perforation 412 extends from the first surface 704 to the second surface 708 through the flexible polymer layer 700. In an embodiment where the electrode layer 604 does not separate a portion of the flexible polymer layer 700 from the durable topcoat layer 580, the one or more perforation 412 may or may not extend through the durable topcoat layer 580, and the one or more perforation 412 may or may not be the perforations of the durable topcoat layer 580 as described above. In one embodiment, the one or more perforation 412 extending through the flexible polymer layer 700 may extend from the second surface 616 of the electrode layer 604 through the electrode layer 604 to the first surface 652. In one embodiment the one or more perforation 412 may extend from the second surface 600 of the durable topcoat layer 580 through the durable topcoat layer 580 to the first surface 592 of the durable topcoat layer 580. In this way, the one or more perforation 412 may extend from the second surface 708 of the flexible polymer layer 700 to the first surface 592 of the durable topcoat layer 580 thus providing one or more air-channel 648 allowing air to move from being in contact with the conductive gel element 588 through the top 596 of the durable topcoat layer 580 of the pad 696.

In one embodiment, the first perforation 412*a* extends through the flexible polymer layer 700 and the second perforation 412*b* extends through both the flexible polymer layer 700 and the electrode layer 604. In another embodiment, the pad 696 includes the first perforation 412*a* which extends through the flexible polymer layer 700 and the durable topcoat layer 580 where the durable topcoat layer 580 and the flexible polymer layer 700 are in contact with each other, and includes the second perforation 412*b* which extends through each of the flexible polymer layer 700, the electrode layer 604, and the durable topcoat layer 580.

In one embodiment, one or more perforation 412 includes a first portion 656 and a second portion 660. As shown in FIG. 28, the first perforation 412*a* includes a first portion 656*a* extending through the flexible polymer layer 700, the electrode element 584, and the durable topcoat layer 580, and a second portion 660*a* extending through the conductive gel element 588. The second perforation 412*b* includes a first portion 656*b* extending through the flexible polymer layer 700, the electrode layer 604, and the durable topcoat layer 580, and a second portion 660*b* extends through the conductive gel element 588.

As shown in FIG. 28, the second portion 660*a* of the first perforation 412*a* and the second portion 660*b* of the second perforation 412*b* extend through the first removeable protection layer 174 and the second removeable protection layer 176. In another embodiment, however, the second portion 660*a* of the first perforation 412*a* and the second portion 660*b* of the second perforation 412*b* do not extend through the first removeable protection layer 174 and the second removeable protection layer 176.

In an embodiment where the pad 696 includes the first removeable protection layer 174, the user, after removing the first removeable protection layer 174, may align the first portion 656 with the second portion 660 of each perforation 412 such that each perforation 412 extends from the bottom 664 through the pad 576, (i.e., through the conductive gel element 588, through flexible polymer layer 700, the electrode element 584, and through the durable topcoat layer 580), to the top 596. In one embodiment when the conductive gel element 588 comprises at least one liquid conductive gel element, the first portion 656 and the second portion 660 of each perforation 412 may not be aligned, such that the liquid conductive gel element does not pass through the first portion 656, but is, instead, maintained within the conductive gel element 588. In one embodiment, the second portion, extending through the conductive gel element 588, may be described in the U.S. Patent Application 62/956,992 entitled "PERFORATED HYDROGEL CONFIGURATIONS AND METHODS OF PRODUCTION AND USE THEREOF" and/or described in the U.S. Patent Application 63/004,016 entitled "ASSEMBLIES CONTAINING TWO CONDUCTIVE GEL COMPOSITIONS AND METHODS OF PRODUCTION AND USE THEREOF" both of which are incorporated by reference in their entirety herein.

Referring to FIG. 29, shown therein is another embodiment of a pad 716. The pad 716 is identical in construction and function as the pad 696 described above and shown in FIG. 28, with the exception that the electrode element 584 and the conductive gel element 588 are arranged to form a plurality of conductive regions 720*a-h* connected to a conductive lead 58*a*. Eight conductive regions 720*a-h* are shown in FIG. 29 by way of example. The conductive regions 720*a-h* are operable to supply current into the patient. The pad 716 includes the durable topcoat layer 580 extending over and between the conductive regions 720*a-h*. In this embodiment, the durable topcoat layer 580 may be formed of a non-conductive material, or be formed of an electrically conductive material that does not receive electrical current from the conductive regions 720*a-h*. The conductive regions 720*a-h* are electrically isolated by one or more dielectric region 146 extending between each adjacently disposed pair of conductive regions 720*a-h*. The dielectric region 146 can be formed by interleaving a dielectric element laterally between each pair of adjacently disposed conductive regions 720*a-h*. The conductive lead 58*a* may include two or more isolated conductor 150 such that each conductive region 720*a-h* is coupled to the generator 54 independently, thus allowing the generator 54 to independently control the TTField generated by each conductive region 720*a-h*.

In such an embodiment, the electronic apparatus 50 may alternate between one or more conductive region 720*a-h* of the pad 716, thus creating and shaping TTFields with increased specificity and precision. A single pad 716 having multiple conductive regions 720*a-h*, can be used as a substitute or in conjunction with the first pad 70*a*, the second pad 70*b*, or the pad 576. In another embodiment, the pad 716 can be constructed in accordance with the pad 696 in which the electrode element 584 is attached to the flexible polymer layer 700 in each of the conductive regions 720*a-h*.

As shown in FIG. 29, the pad 716 further includes one or more perforation 412. The one or more perforation 412 may be located within one or more conductive region 720*a-h* such as shown by first perforation 412*a* or may be located within the one or more dielectric region 146 as shown by second perforation 412*b*. In one embodiment, the one or more conductive region 720*a-h* may have one or more first perforation 412*a*; however, in another embodiment, one or more conductive region 720*a-h* may not include the first perforation 412*a*. Similarly, one or more dielectric region 146 may comprise one or more second perforation 412*b*. In one embodiment, the pad 716 includes one or more first perforation 412*a* and one or more second perforation 412*b*.

In one embodiment, the generator 54, connected to the pad 716, may supply a first electric signal having a first power and a first frequency to a first group of one or more conductive region 720*a-h* (e.g., conductive region 720*a* and conductive region 720*b*, for example) at a first instance in time to generate a first TTField. The generator 54, at a second instance in time, may supply a second electric signal having a second power, the same as or different from the first power, and a second frequency, the same as or different from the first frequency, to a second group of one or more conductive region 720*a-h* (e.g., conductive region 720*b* and conductive region 720*c*, for example) to generate a second TTField. The second group may include one or more conductive region 720*a-h* included in the first group, or may not include one or more conductive region 720*a-h* included in the first group. The first TTField and the second TTField may target the same target area or may target different target areas. In one embodiment, the first instance in time and the second instance in time may overlap, that is, the generator 54 may supply the second electric signal to the second group while also supplying the first electric signal to the first group. In such an embodiment, the first group and the second group may be mutually exclusive.

In one embodiment, the generator 54, connected to the pad 716, may supply a first electrical signal having a first power and a first frequency to a first group of one or more conductive region 720*a-h* (e.g., conductive region 720*a* and conductive region 720*b*, for example) and supply a second electrical signal having a second power and a second frequency to a second group of one or more conductive region 720*a-h* (e.g., conductive region 720*b* and conductive region 720*c*, for example) at the same instance in time. That is, the generator 54, may simultaneously supply the first electric signal to the first group and the second electric signal to the second group. While the above embodiments describe only the first group and the second group, it is understood that there may be more than two groups. In one embodiment, the number of groups is dependent on the number of combinations of the conductive regions 720*a-h*.

In one embodiment, the generator 54 may be connected to the pad 716 and the pad 576. In such an embodiment, the generator 54 may supply the electric signal to the one or more conductive region 720_a-h_ of the pad 716. The one or more conductive region 720_a-h_ receiving the electric signal may then generate a TTField between each of the one or more conductive region 720_a-h_ of the pad 716 and the pad 576.

Figure 30:
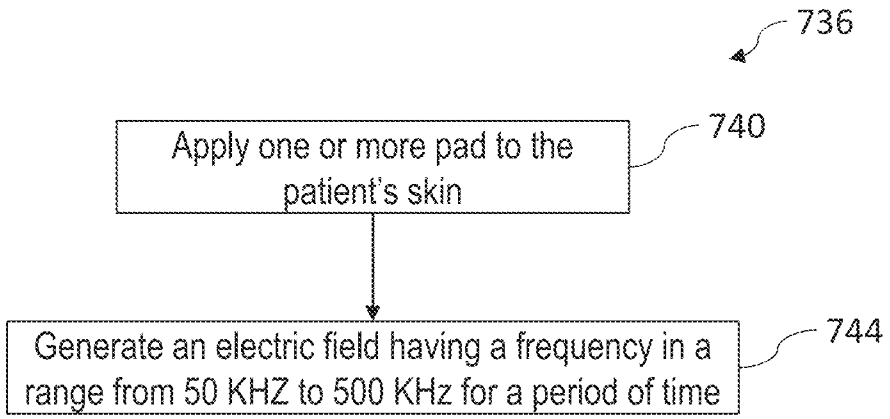
FIG. 30 is a diagram of an exemplary embodiment of a process of treating a tumor utilizing the pads of FIGS. 26-29.

Referring now to FIG. 30, shown therein is an exemplary embodiment of a process 736 of using the electronic apparatus 50 and the pads 100_a_, 576, 696, or the pad 716 to apply a TTField to a patient.

When the pads 696 are used, preferably such pads 696 are attached to the skin of the patient on opposite sides of a tumor. For example, in the context of a brain tumor positioned in the center of a person's head, one of the pads 696 could be positioned on the right side of the person's head, and another one of the pads 696 could be positioned on the left side of the person's head. For both of the pads 696, the flexible polymer layer 700 faces the person's skin. When pressed against the skin, an adhesive may adhere the flexible polymer layer 700 to the skin and holds the flexible polymer layer 700 adjacent to the skin. When the conductive gel element 588 is provided, the conductive gel element 588 is disposed between the flexible polymer layer 700 and the person's skin. When the conductive gel element 588 is omitted (which is less preferable), the flexible polymer layer 700 will rest directly on the person's skin. Each of the pads 696 form one of the electrodes 18_a_ and 18_b_ (see FIG. 1). After the electrodes 18_a_ and 18_b_, for example, have been affixed to the person's skin, an AC voltage is applied between the pads 696. The electrode element 584 acts as a capacitor's plate, and the flexible polymer layers 700 act as a capacitor's insulating layer, and an AC electric field will be capacitively coupled through the flexible polymer layers 700 into the person's body.

Thus, the process 736 generally comprises the steps of: applying two or more of the first pad 70_a_, the second pad 70_b_, the pad 576, the pad 696, or the pad 716 to the patient's skin (step 664) and generating (and supplying) an alternating electric field having a frequency in a range of from about 50 kHz to about 576 kHz for a period of time (step 744) to the pad(s) applied to the patient to deliver TTF fields to the patient. The step of applying two or more of the first pad 70_a_, the second pad 70_b_, the pad 576, or the pad 696 to the patient's skin may be performed by the user. A single pad 716 having multiple conductive regions 720 can be used in place of two or more of the first pad 70_a_, the second pad 70_b_, the pad 576, or the pad 696.

In one embodiment, before applying one (the pad 716) or two or more of the first pad 70_a_, the second pad 70_b_, the pad 576 or the pad 696 to the patient's skin, the patient's skin may need to be cleaned (e.g., such as but not limited to, cleansing of the skin of foreign matter or biological matter and shaving of the skin, if necessary) to enable the conductive gel element 128 to adhere to the patient's skin. The step of generating an alternating electric field (TTField) (step 744) may be performed by the generator 54 and may be instantiated by an operation performed by the user or control box 66.

In one embodiment, step 744 may be performed more than one time and the period of time for which the step 744 is performed a first time may be the same as or different from the period of time for which the step 744 is performed a second time (or other period(s) of time beyond the second time). In some embodiments, step 744 is only performed once before the process 736 is repeated. There may be a time period between each time the process 736 is repeated. Each time the process 736 is repeated, the time period may be the same as or different from the previous time period. Each time the process 736 is repeated, the two or more of the first pad 70_a_, the second pad 70_b_, the pad 716, and/or the pad 576 may be placed in the same or a different position on the patient's skin.

The following is a number list of non-limiting illustrative embodiments of the inventive concept of the sixth mode disclosed herein:

73. A system, comprising:
- a generator configured to generate an electrical signal having an alternating current waveform at a frequency in a range from 50 kHz to 500 kHz;
- a first conductive lead electrically coupled to the generator, the first conductive lead configured to carry the electrical signal;
- a first pad having a first electrode element directly connected to a first conductive gel element, the first conductive element is configured to be in contact with a patient's skin, the first electrode element and the first conductive gel element define at least one perforation extending through the first electrode element and the first conductive gel element;
- a second conductive lead electrically coupled to the generator, the second conductive lead configured to carry the electrical signal; and
- a second pad having a second electrode element directly connected to a second conductive gel element, and the second conductive gel element being configured to be in contact with a patient's skin.

74. The system of illustrative embodiment 73, wherein the first electrode element includes an electrode layer electrically coupled to a conductive support layer, the conductive support layer being intermediate to the electrode layer and the conductive gel element.

75. The system of illustrative embodiment 74, wherein the second electrode element includes an electrode layer electrically coupled to a conductive support layer, the conductive support layer being intermediate to the electrode layer and the conductive gel element.

76. The system of illustrative embodiment 73, further comprising a blocking capacitor configured to block direct current in the electrical signal.

77. The system of illustrative embodiment 76, wherein the blocking capacitor is a non-polarized capacitor.

78. The system of illustrative embodiment 76, wherein the blocking capacitor has a capacitance of about 1 μF.

79. The system of illustrative embodiment 76, wherein the generator includes the blocking capacitor.

80. The system of illustrative embodiment 76, wherein either the first pad, the second pad, or both the first pad and the second pad include the blocking capacitor.

81. The system of illustrative embodiment 76, wherein the blocking capacitor is a first blocking capacitor and further comprising a second blocking capacitor configured to block direct current in the electrical signal.

82. The system of illustrative embodiment 81, wherein either the first pad, the second pad, or both the first pad and the second pad include the second blocking capacitor.

83. The system of illustrative embodiment 73, wherein the first conductive gel element further includes a first hydrogel layer, a support layer, and a second hydrogel layer, the first hydrogel layer being a first electrically conductive hydrogel and the second hydrogel layer being a second electrically conductive hydrogel.

84. The system of illustrative embodiment 83, wherein the first electrically conductive hydrogel and the second electrically conductive hydrogel are not the same hydrogel.

85. The system of illustrative embodiment 83, wherein the support layer is electrically conductive.

86. The system of illustrative embodiment 73, wherein the second hydrogel element further includes a first hydrogel layer, a support layer, and a second hydrogel layer, the first hydrogel layer being a first electrically conductive hydrogel and the second hydrogel layer being a second electrically conductive hydrogel.

87. The system of illustrative embodiment 86, wherein the first electrically conductive hydrogel and the second electrically conductive hydrogel are not the same hydrogel.

88. The system of illustrative embodiment 86, wherein the support layer is electrically conductive.

89. The system of illustrative embodiment 73, further comprising one or more temperature sensor configured to measure a temperature of the first pad.

90. The system of illustrative embodiment 89, further comprising a control box configured to monitor the one or more temperature sensor and turn off the generator if the temperature exceeds a comfortability threshold.

91. The system of illustrative embodiment 90, wherein the comfortability threshold is about 40 degrees Celsius.

92. A pad, comprising:

a topcoat layer;

an electrode element connected to the topcoat layer, and configured to receive an electrical signal from a generator producing an electric signal as a TTField; and a conductive gel element directly connected to the electrode element so as to receive an electrical current from the electrode element, the conductive gel element configured to be in contact with a patient's skin, the electrode element and the conductive gel element define at least one perforation extending through the electrode element and the conductive gel element.

93. The pad of illustrative embodiment 92, further comprising a conductive lead configured to carry the electrical signal, the conductive lead configured to be electrically coupled to the generator, the conductive lead electrically coupled to the electrode element.

94. The pad of illustrative embodiment 92, wherein the conductive gel element further includes a first conductive gel layer, a support layer, and a second conductive gel layer, the first hydrogel layer being a first electrically conductive gel and the second conductive gel layer being a second electrically conductive gel.

95. The pad of illustrative embodiment 94, wherein the first electrically conductive gel and the second electrically conductive gel are not the same conductive gel.

96. The pad of illustrative embodiment 94, wherein the support layer is electrically conductive.

97. The pad of illustrative embodiment 94, further comprising a blocking capacitor configured to block direct current in the electrical signal.

98. The pad of illustrative embodiment 97, wherein the blocking capacitor is a non-polarized capacitor.

99. The pad of illustrative embodiment 97, wherein the blocking capacitor has a capacitance of about 1 μF.

100. The pad of illustrative embodiment 92, wherein the topcoat layer, the electrode element, and the conductive gel element are constructed of flexible materials and configured to conform to a body of a patient.

101. A method, comprising:

applying at least two conductive regions to a skin of a patient;

coupling the conductive regions to a generator before or after applying the at least two conductive regions to the patient, the generator configured to generate an electrical signal having an alternating current waveform at frequencies in the range from 50 kHz to 500 kHz, each conductive region having an electrode element and directly connected to a conductive gel element so as to supply an electrical current from the electrode element to the conductive gel element, the electrode elements being electrically coupled to the generator and, upon receiving the electrical signal supplies electrical current to the conductive gel element, the conductive gel element being in contact with a patient's skin, the electrode elements and the conductive gel element defining at least one perforation extending through the electrode element and the conductive gel element to allow air to pass through the conductive regions to the skin of the patient; and activating the generator to supply the electrical signal to the electrode elements, thereby supplying electrical current to the patient through the conductive gel element.

102. The method of illustrative embodiment 101 wherein coupling the conductive regions to the skin of the patient is defined further as connecting a first lead to a first one of the conductive regions, and connecting a second lead to a second one of the conductive regions.

103. The method of illustrative embodiment 101, further comprising the step of passing the electrical signal through a blocking capacitor configured to block direct current in the electrical signal.

104. The method of illustrative embodiment 103, wherein the blocking capacitor is a non-polarized capacitor.

105. The method of illustrative embodiment 103, wherein the blocking capacitor has a capacitance of about 1 μF.

106. The method of illustrative embodiment 101, wherein the electrode element, and the conductive gel element are constructed of flexible materials and configured to conform to a body of a patient, and wherein the step of applying at least two conductive regions to a skin of a patient is defined further as conforming the electrode element and the conductive gel element to the skin of the patient.

107. A system, comprising:

a generator configured to generate an electrical signal having an alternating current waveform at a frequency in a range from 50 kHz to 500 kHz;

a first conductive lead electrically coupled to the generator, the first conductive lead configured to carry the electrical signal;

a first pad having a first electrode element connected to a first flexible polymer layer, and a first conductive gel element, the first flexible polymer layer between the first electrode element and the first conductive gel element, the first conductive element being configured to be in contact with a patient's skin, the first electrode element, the first flexible polymer layer, and the first conductive gel element defining at least one perforation extending through the first electrode element, the first flexible polymer layer, and the first conductive gel element, the first flexible polymer layer being a first dielectric material;

a second conductive lead electrically coupled to the generator, the second conductive lead configured to carry the electrical signal; and a second pad having a second electrode element connected to a second flexible polymer layer, and a second conductive gel element, the second conductive gel element being configured to be in contact with the patient's skin, the second flexible polymer layer positioned in between the second electrode element and the second conductive gel element, and being a second dielectric material.

108. The system of illustrative embodiment 107, wherein the first electrode element includes an electrode layer electrically coupled to a conductive support layer, the conductive support layer being intermediate to the electrode layer and the first flexible polymer layer.

109. The system of illustrative embodiment 107, wherein the second electrode element includes an electrode layer electrically coupled to a conductive support layer, the conductive support layer being intermediate to the electrode layer and the first flexible polymer layer.

110. The system of illustrative embodiment 107, further comprising a blocking capacitor configured to block direct current in the electrical signal.

111. The system of illustrative embodiment 110, wherein the blocking capacitor is a non-polarized capacitor.

112. The system of illustrative embodiment 110, wherein the blocking capacitor has a capacitance of about 1 μF.

113. The system of illustrative embodiment 110, wherein the generator includes the blocking capacitor.

114. The system of illustrative embodiment 110, wherein either the first pad, the second pad, or both the first pad and the second pad include the blocking capacitor.

115. The system of illustrative embodiment 110, wherein the blocking capacitor is a first blocking capacitor and further comprising a second blocking capacitor configured to block direct current in the electrical signal.

116. The system of illustrative embodiment 115, wherein either the first pad, the second pad, or both the first pad and the second pad include the second blocking capacitor.

117. The system of illustrative embodiment 107, wherein the first conductive gel element further includes a first hydrogel layer, a support layer, and a second hydrogel layer, the first hydrogel layer being a first electrically conductive hydrogel and the second hydrogel layer being a second electrically conductive hydrogel.

118. The system of illustrative embodiment 117, wherein the first electrically conductive hydrogel and the second electrically conductive hydrogel are not the same hydrogel.

119. The system of illustrative embodiment 117, wherein the support layer is electrically conductive.

120. The system of illustrative embodiment 107, wherein the second hydrogel element further includes a first hydrogel layer, a support layer, and a second hydrogel layer, the first hydrogel layer being a first electrically conductive hydrogel and the second hydrogel layer being a second electrically conductive hydrogel.

121. The system of illustrative embodiment 120, wherein the first electrically conductive hydrogel and the second electrically conductive hydrogel are not the same hydrogel.

122. The system of illustrative embodiment 120, wherein the support layer is electrically conductive.

123. The system of illustrative embodiment 107, further comprising one or more temperature sensor configured to measure a temperature of the first pad.

124. The system of illustrative embodiment 123, further comprising a control box configured to monitor the one or more temperature sensor and turn off the generator if the temperature exceeds a comfortability threshold.

125. The system of illustrative embodiment 124, wherein the comfortability threshold is about 40 degrees Celsius.

126. A pad, comprising:

a topcoat layer;

an electrode element connected to the topcoat layer, and configured to receive an electrical signal from a generator producing an electric signal as a TTField;

a flexible polymer layer connected to the electrode element, the flexible polymer layer being constructed of a dielectric material; and a conductive gel element connected to the flexible polymer layer to electrically isolate the electrode element from the conductive gel element, the conductive gel element configured to be in contact with a patient's skin, the electrode element, the flexible polymer layer, and the conductive gel element define at least one perforation extending through the electrode element, the flexible polymer layer, and the conductive gel element.

127. The pad of illustrative embodiment 127, further comprising a conductive lead configured to carry the electrical signal, the conductive lead configured to be electrically coupled to the generator, the conductive lead electrically coupled to the electrode element.

128. The pad of illustrative embodiment 126, wherein the conductive gel element further includes a first conductive gel layer, a support layer, and a second conductive gel layer, the first hydrogel layer being a first electrically conductive gel and the second conductive gel layer being a second electrically conductive gel.

129. The pad of illustrative embodiment 128, wherein the first electrically conductive gel and the second electrically conductive gel are not the same conductive gel.

130. The pad of illustrative embodiment 128, wherein the support layer is electrically conductive.

131. The pad of illustrative embodiment 128, further comprising a blocking capacitor configured to block direct current in the electrical signal.

132. The pad of illustrative embodiment 131, wherein the blocking capacitor is a non-polarized capacitor.

133. The pad of illustrative embodiment 131, wherein the blocking capacitor has a capacitance of about 1 μF.

134. The pad of illustrative embodiment 126, wherein the topcoat layer, the electrode element, the flexible polymer layer, and the conductive gel element are constructed of flexible materials and configured to conform to a body of a patient.

135. A method, comprising:

applying at least two conductive regions to a skin of a patient, coupling the conductive regions to a generator before or after applying the at least two conductive regions to the skin, the generator configured to generate an electrical signal having an alternating current waveform at frequencies in the range from 50 kHz to 500 kHz, each conductive region having an electrode element, flexible polymer layer, and a conductive gel element with the flexible polymer layer electrically isolating the electrode element from the conductive gel element, the electrode elements being electrically coupled to the generator and, upon receiving the electrical signal supplying an electric field to the conductive gel element through the flexible polymer layer, the conductive gel element being in contact with a patient's skin, the electrode elements, the flexible polymer layers, and the conductive gel element defining at least one perforation extending through the electrode element, the flexible polymer layers, and the conductive gel element to allow air to pass through the conductive regions to the skin of the patient; and activating the generator to supply the electrical signal to the electrode elements, thereby supplying the electric field to the patient through the conductive gel element.

136. The method of illustrative embodiment 135 wherein coupling the conductive regions to the skin of the patient is defined further as connecting a first lead to a first one of the conductive regions, and connecting a second lead to a second one of the conductive regions.

137. The method of illustrative embodiment 135, further comprising the step of passing the electrical signal through a blocking capacitor configured to block direct current in the electrical signal.

138. The method of illustrative embodiment 135, wherein the blocking capacitor is a non-polarized capacitor.

139. The method of illustrative embodiment 135, wherein the blocking capacitor has a capacitance of about 1 μF.

140. The method of illustrative embodiment 135, wherein the electrode element, the flexible polymer layer, and the conductive gel element are constructed of flexible materials and configured to conform to a body of a patient, and wherein the step of applying at least two conductive regions to a skin of a patient is defined further as conforming the electrode element, the flexible polymer layer, and the conductive gel element to the skin of the patient.

Seventh Mode: Nonconductive Pad with Air-Channels

A seventh mode of the present disclosure includes a system and method of implementing the system, the system comprising a generator configured to generate an electrical signal having an alternating current waveform at a frequency in a range from 50 kHz to 576 kHz; a first conductive lead electrically coupled to the generator, the first conductive lead configured to carry the electrical signal; a first pad having a first electrode element electrically coupled to a first conductive gel element to supply electrical current to the first conductive gel element, the first electrode element having an electrode layer and a non-conductive layer, wherein the first electrode element is electrically coupled to the first conductive lead, and the first conductive gel element is configured to be in contact with a patient's skin; and a second pad having a second electrode element electrically coupled to a second conductive gel element to supply electrical current to the second conductive gel element, wherein the second electrode element is electrically coupled to the second conductive lead, and the second conductive gel element is configured to be in contact with a patient's skin.

Figure 31:
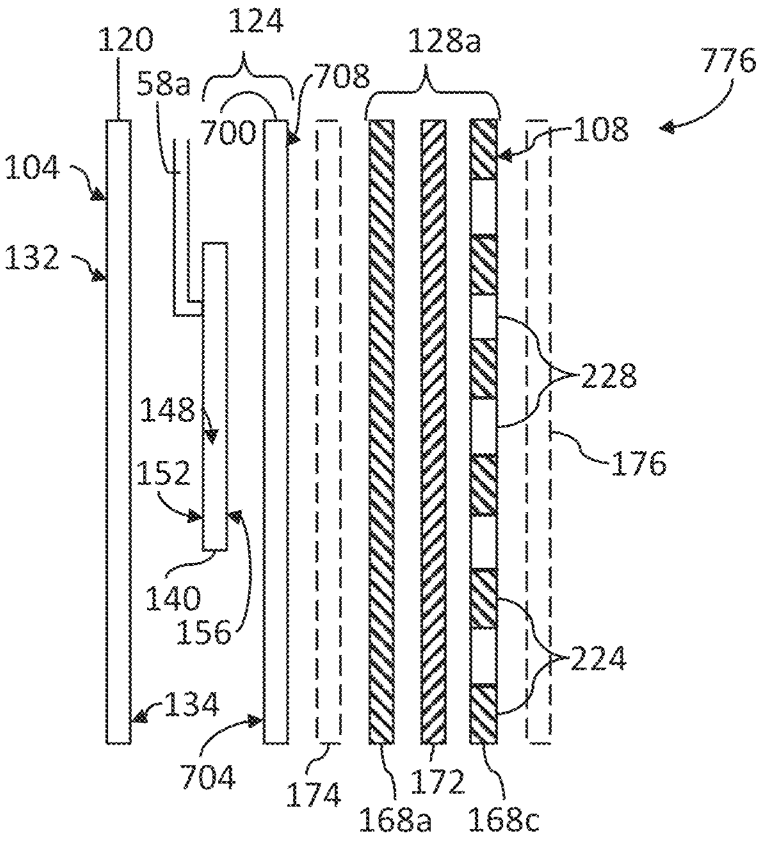
FIG. 31 is an exploded side view of another exemplary embodiment of a pad constructed in accordance with the present disclosure having a non-conductive layer electrically isolating an electrode element from a conductive gel element.

FIG. 31 illustrates another exemplary embodiment of a pad 776 constructed in accordance with the present disclosure. The pad 776 is an exemplary embodiment of the pad 70*a* and the pad 70*b*. The pad 776 is similar in construction and function to the conductive pad 220 described above with respect to FIG. 10, with the exception that the conductive support layer 144 may be omitted, and a flexible polymer layer 700 is positioned between the electrode layer 140 and the conductive gel element 128*a*. Elements common between the conductive pad 220 and the pad 776 are labeled with common reference numerals. The flexible polymer layer 700 may be constructed of a dielectric material as discussed above. The flexible polymer layer 700 may be provided with a first surface 704, and a second surface 708. The first surface 704 may be attached to or otherwise coupled to the second surface 156 of the electrode layer 140 and the second surface 708 may be in direct contact with the conductive gel element 128*a*. In some embodiments, an entirety of the first surface 704 is in direct contact with the second surface 156 of the electrode layer 140, and the second surface 708 is in direct contact with the conductive gel element 128*a*.

The following is a number list of non-limiting illustrative embodiments of the inventive concept of the seventh mode disclosed herein:

141. A system, comprising:

a generator configured to generate an electrical signal having an alternating current waveform;

a first conductive lead electrically coupled to the generator, the first conductive lead configured to carry the electrical signal;

a first pad having a first electrode element connected to a first conductive gel element, the first conductive gel element is configured to be in contact with a patient's skin, the first electrode element having a first electrode layer electrically coupled to a first non-conductive layer, the first non-conductive layer being intermediate to the first electrode layer and the first conductive gel element the first conductive gel element having a first conductive gel layer formed of a first shaping member and one or more first air-channel;

a second conductive lead electrically coupled to the generator, the second conductive lead configured to carry the electrical signal; and a second pad having a second electrode element directly connected to a second conductive gel element, and the second conductive gel element being configured to be in contact with a patient's skin the second conductive gel element having one or more second air-channel.

142. The system of illustrative embodiment 141, wherein the first non-conductive layer is a flexible polymer layer.

143. The system of illustrative embodiment 142, wherein the flexible polymer layer is formed of a dielectric material.

144. The system of illustrative embodiment 143, wherein the flexible polymer layer is configured as an insulator.

145. The system of illustrative embodiment 143, wherein the dielectric material comprises a dielectric constant on an order of 40.

146. The system of illustrative embodiment 143, wherein the first non-conductive layer includes ceramic nanoparticles.

147. The system of illustrative embodiment 143, wherein the dielectric material provides at least one frequency between 100 kHz and 500 kHz and a dielectric constant of at least 20.

148. The system of illustrative embodiment 141, wherein the first non-conductive layer has a thickness of less than 20 microns.

149. The system of illustrative embodiment 141, wherein the first non-conductive layer has a thickness of less than 10 microns.

150. The system of illustrative embodiment 141, wherein the first non-conductive layer has a thickness of less than 5 microns.

151. The system of illustrative embodiment 141, wherein thickness of the first non-conductive layer multiplied by a dielectric constant of the first non-conductive layer is at least 200 V.

152. The system of illustrative embodiment 141, wherein thickness of the first non-conductive layer multiplied by a dielectric constant of the first non-conductive layer is at least 400 V.

153. The system of illustrative embodiment 141, wherein the first non-conductive layer includes a first surface and a second surface, the first surface coupled to the first electrode layer and the second surface in direct contact with the first conductive gel element.

154. The system of illustrative embodiment 153, wherein entirety of the first surface is in direct contact with the first electrode layer.

155. The system of illustrative embodiment 153, wherein entirety of the second surface is in direct contact with the first conductive gel element.

156. The system of illustrative embodiment 141, wherein the second electrode element includes an electrode layer electrically coupled to a second non-conductive layer, the second non-conductive layer is intermediate to the electrode layer and the first conductive gel element.

157. A pad, comprising:

a topcoat layer;

an electrode element connected to the topcoat layer, and configured to receive an electrical signal from a generator producing an electric signal as a TTField, the electrode element including an electrode layer electrically coupled to a non-conductive layer;

a conductive gel element connected to the electrode element so as to receive an electrical current from the electrode element, the conductive gel element including a conductive gel layer and a shaping member, the shaping member positioned within the conductive gel layer and having a first side and a second side, wherein the conductive gel layer includes a plurality of protrusions and one or more air-channel on the second side of the shaping member, the conductive gel layer being configured to be in contact with a patient's skin; and a non-conductive layer intermediate to the electrode layer and the conductive gel element.

158. The pad of illustrative embodiment 157, wherein the non-conductive layer is a flexible polymer layer with at least a portion of the flexible polymer layer in direct contact with the conductive gel element.

159. A pad, comprising:

a topcoat layer;

an electrode element connected to the topcoat layer, and configured to receive an electrical signal from a generator producing an electric signal as a TTField;

a non-conductive flexible polymer layer connected to the electrode element, the non-conductive flexible polymer layer being constructed of a dielectric material; and a conductive gel element connected to the non-conductive flexible polymer layer to electrically isolate the electrode element from the conductive gel element, the conductive gel element configured to be in contact with a patient's skin and the non-conductive flexible polymer layer, the conductive gel element including a conductive gel layer and a shaping member, the shaping member positioned within the conductive gel layer and having a first side and a second side, wherein the conductive gel layer includes a plurality of protrusions and one or more air-channel on the second side of the shaping member.

160. The pad of illustrative embodiment 159, further comprising a conductive lead configured to carry the electrical signal, the conductive lead configured to be electrically coupled to the generator, the conductive lead electrically coupled to the electrode element.

Eighth Mode: Conductive and Nonconductive Pads with Kirigami-Like Cuts

An eighth mode of the present disclosure includes a pad having a topcoat layer, an electrode element and a conductive gel element are described. The electrode element is connected to the topcoat layer, and configured to receive an electrical signal from a generator producing an electric signal as a TTField. The conductive gel element is directly connected to the electrode element so as to receive an electrical current from the electrode element. The conductive gel element is configured to be in contact with a patient's skin. The electrode element and the conductive gel element define kirigami-like cuts, the kirigami-like cuts being a predetermined pattern of cuts resulting in the electrode element, the flexible polymer layer, and the conductive gel element forming a three-dimensional shape conforming to a predetermined portion of a patient's body.

Figure 32:
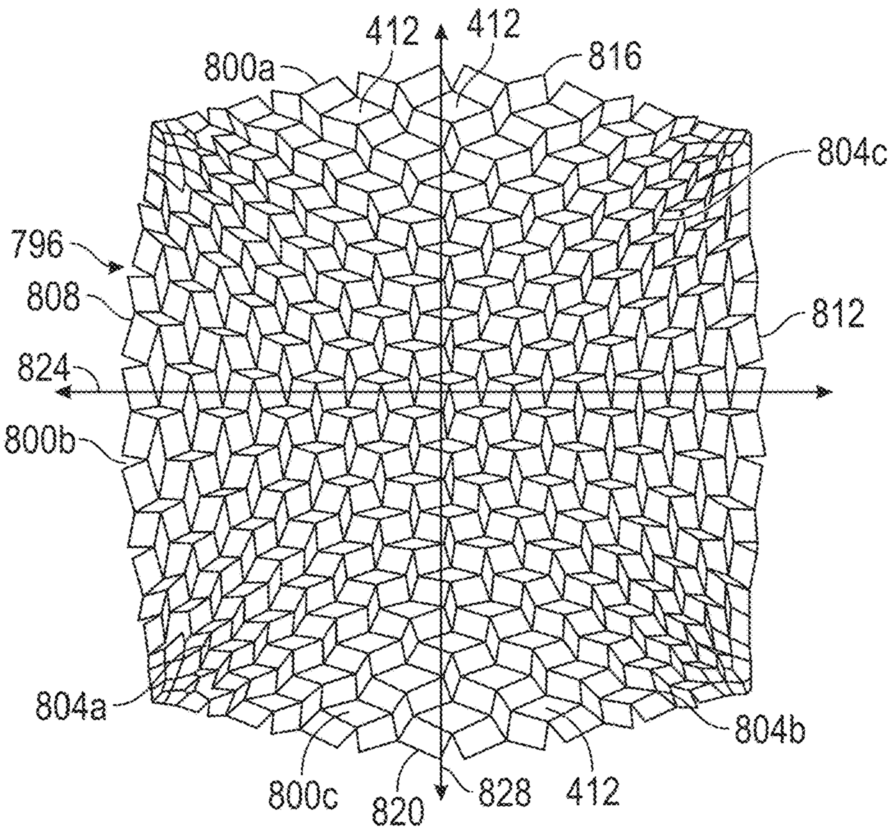
FIG. 32 is a top plan view of another exemplary embodiment of a pad constructed in accordance with the present disclosure, the pad being in a planar state.
Figure 33:
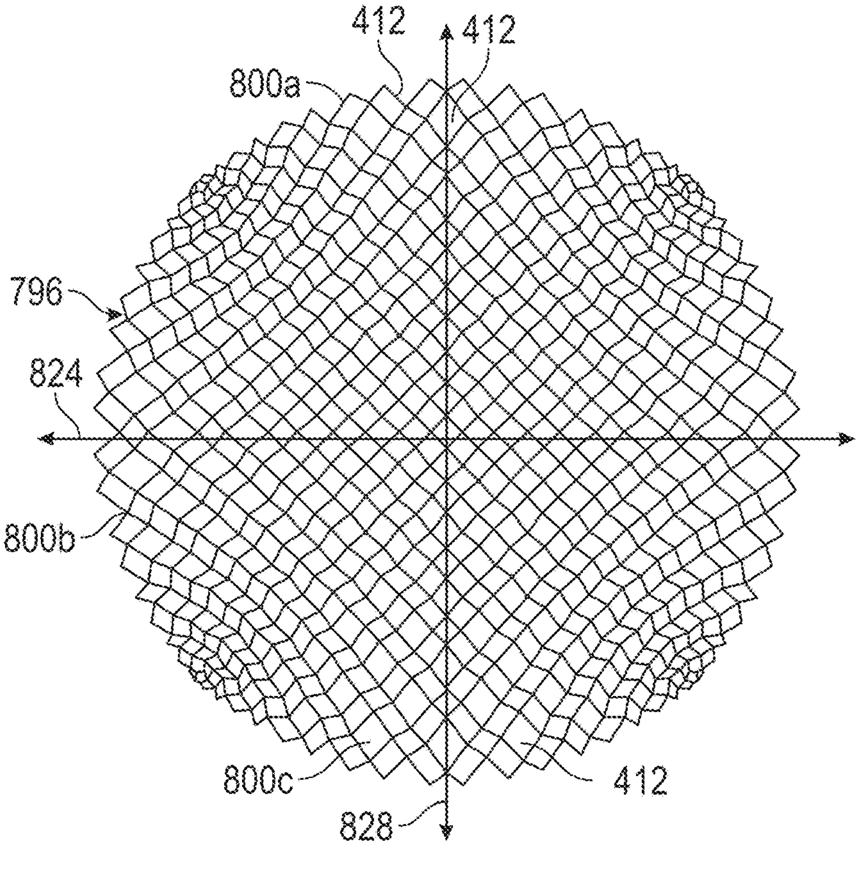
FIG. 33 is a top plan view of the exemplary pad of FIG. 32 being in a three-dimensional shape configured to conform to a portion of a patient's head in accordance with the present disclosure.

Referring now to FIG. 32, shown therein is a top plan view of another exemplary embodiment of a pad 796 constructed in accordance with the present disclosure. The pad 796 is an exemplary embodiment of the pad 70*a* and the pad 70*b*. The pad 796 is a flat or planar shaped device having a plurality of kirigami-like cuts 800 forming a plurality of flexible joints 804 between adjacent pairs of the kirigami-like cuts 800 to cause the pad 796 to conform to a three-dimensional shape of a patient's body part, such as a knee, elbow, head or the like. Only a few of the kirigami-like cuts 800 are labeled in FIG. 32 as 724*a*, 724*b* and 724*c* for purposes of clarity. Similarly, only a few of the flexible joints 804 are labeled in FIG. 32 as 728*a*, 728*b*, and 728*c* for purposes of clarity. The pad 796 is shown in FIG. 33 assuming a three-dimensional shape of a portion of the patient's head, due to the kirigami-like cuts 800 forming bendable areas between the kirigami-like cuts 800.

Figure 34:
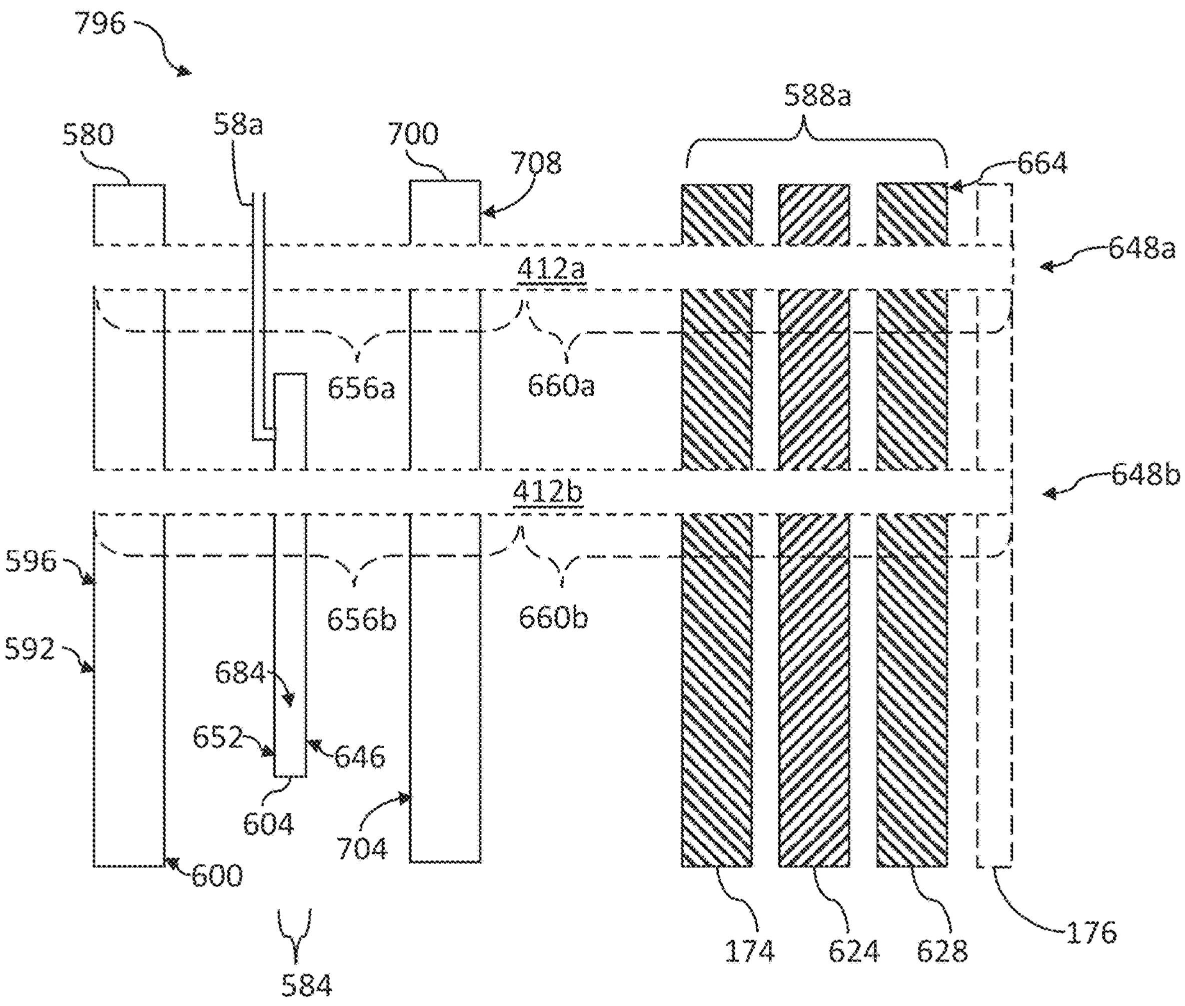
FIG. 34 is an exploded view of another embodiment of the pad of FIGS. 32 and 33 being in a conductive form and configured to supply alternating current TTF fields into the skin of a patient.
Figure 35:
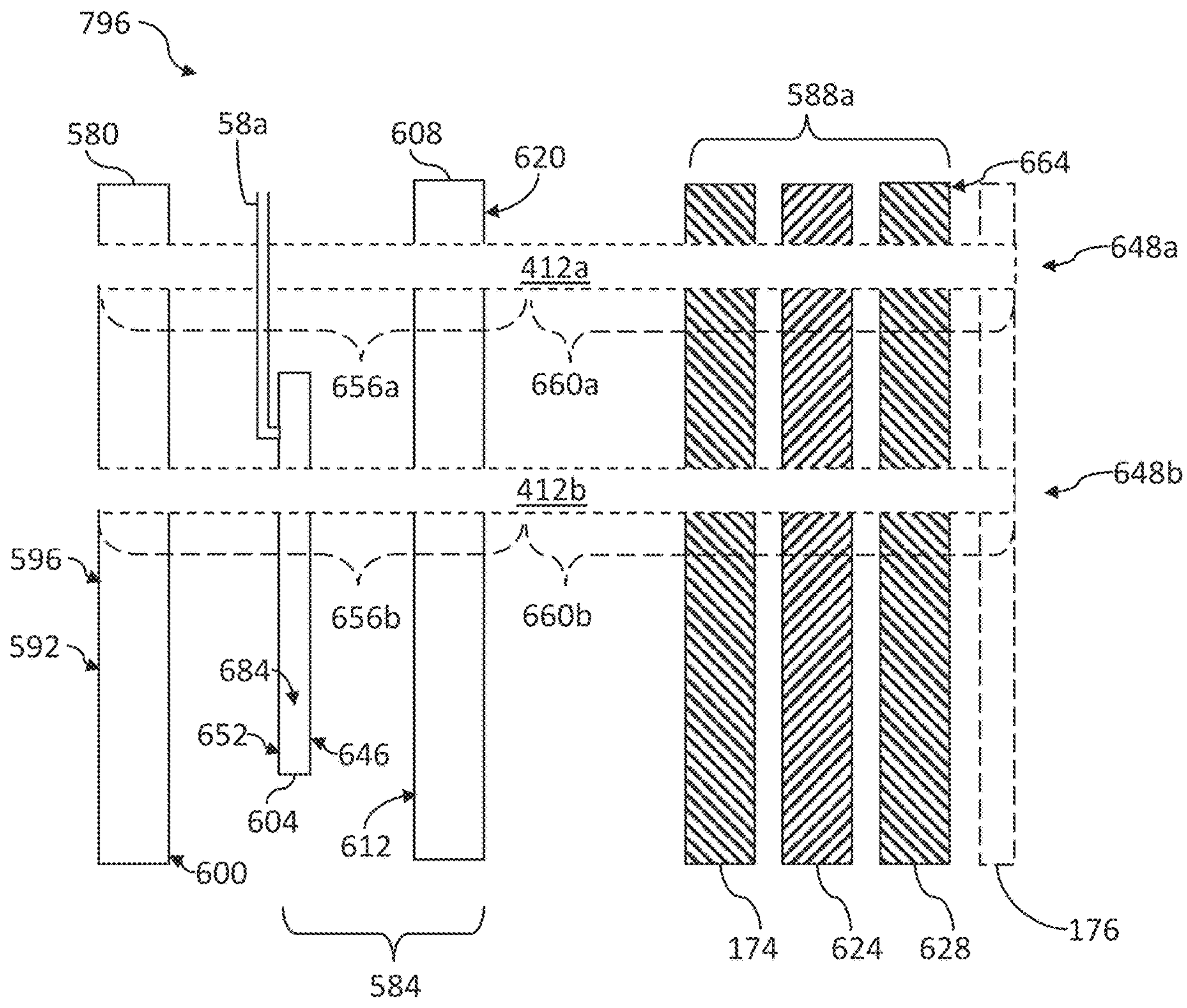
FIG. 35 is an exploded view of an embodiment of the pad of FIGS. 32 and 33 being in a non-conductive form and configured to generate capacitively coupled fields into a patient.

FIGS. 34 and 35 are exploded views of embodiments of the pad 796. As will be explained below, the pad 796 is constructed in a similar manner as the pads 576 or 696 discussed above in FIG. 26 and FIG. 28, with the exception that the pad 796 does not include the first removeable protection layer 174. Rather, the conductive gel element 588 is connected directly to either the conductive support layer 608 (see FIG. 35) or the flexible polymer layer 700 (see FIG. 34), prior to the pad 796 being provided with kirigami-like cuts 800 and shaped as discussed below. In the example shown in FIG. 34, the pad 796 includes the flexible polymer layer 700, but such disclosure is equally applicable to the embodiment of the pad 796 having the conductive support layer 608 depicted in FIG. 35. In general, the pad 796 is constructed of flexible materials so that the pad 796, including the conductive gel element 588, can conform to a body part of the patient.

The flexible polymer layer 700, the conductive gel element 588, the electrode element 584, and/or the durable topcoat layer 580 of the pad 796 are provided with the kirigami-like cuts 800 to provide a plurality of first perforation 412*a* and second perforation 412*b* extending through the flexible polymer layer 700 (FIG. 34), the conductive support layer 608 (see FIG. 35), the conductive gel element 588, the electrode element 584, and/or the durable topcoat layer 580. The perforation 412 may be positioned such that air is capable of passing through the pad 796 to reach the patient's skin, thus forming one or more air-channel 648, e.g., air-channel 648*a* formed by the first perforation 412*a* and air-channel 648*b* formed by the second perforation 412*b*. The perforation 412 extend through at least a portion of the conductive gel element 588, the first removeable protection layer 174, the electrode element 584*a*, and/or the durable topcoat layer 580*a* to allow for an increased air flow to a patient's skin. The one or more air-channel 648, by facilitating increased air flow to the patient's skin, enables release of moisture on the patient's skin, reduces and/or eliminates macerations, lesions/ulcers, and dermatitis, as well as decreases operating temperature when the TTField is applied to the pad 796.

In addition, given prolonged exposure of the pad 796 to the patient's skin, the pad 796 should be optimized for use at body temperature (i.e., in a range of from about 34° C. to about 40° C.). At these temperatures, air flow introduced by the perforation 412 maximizes evaporative cooling thereby allowing for a reduced operating temperature and cooling effect to the patient's skin.

As shown in FIG. 32, the pad 796 is in a planar configuration and has a generally rectangular shape, although the pad 796 can be provided with other shapes, such as circular, oval, fanciful, or the like. The pad 796 includes a first side 808, a second side 812, a first end 816 and a second end 820. The pad 796 is also provided with a first longitudinal axis 824 extending from the first side 808 to the second side 812, and a second longitudinal axis 828 extending from the first end 816 to the second end 820. When the predetermined body part is the patient's head, the kirigami-like cuts 800 can be symmetrical about the first longitudinal axis 824, and the second longitudinal axis 828. As shown in FIG. 33, the pad 796 is in a non-planar, semi-spherical configuration and has a generally circular shape from a top plan view. The perforation 412 formed by the kirigami-like cuts 800 expand as the pad 796 is formed into the three-dimensional shape.

When the pad 796 includes the flexible polymer layer 700 (see FIG. 34), the pad 796 provides a non-conductive, electric field throughout the extent of the electrode layer 604. When the pad 796 includes the conductive support layer 608, the pad 796 provides electricity into the conductive gel element 588*a* generally throughout the extend of the conductive support layer 608. Due to the kirigami-like cuts 800 and the resulting re-shaping of the pad 796, including the electrode layer 604, the flexible polymer layer 700 (or in some embodiments the conductive support layer 608), and the conductive gel element 588*a*, a distance between various portions of the pad 796 is flexible, and not fixed. Further, because the kirigami-like cuts 800 are formed within the electrode layer 604, the flexible polymer layer 700 (when present), and the conductive support layer 608 (when present), distances between portions of the electrode layer 604, the flexible polymer layer 700, and the conductive support layer 608 on adjacent sides of the perforation 412 (and otherwise) vary in a predetermined manner when the pad 796 is applied to the patient and are shaped to conform to the patient's body.

Kirigami is a form of art in which a planar material, i.e., paper, is cut and folded to form a three-dimensional shape. In Kirigami, the planar material may be folded into an overlapping planar shape, and then cut through multiple overlapping sections simultaneously so that the resulting planar materials have symmetrical cuts and resulting symmetrical openings when the folded material is unfolded into the planar shape.

The term Kirigami-like cuts, as used herein, refers to a predetermined pattern of cuts within the materials (which may be planar in shape) forming the pad 796, that results in the formation of the flexible joints 804 in the pad 796 to assist the pad 796 in forming a three-dimensional shape conforming to a predetermined portion of a patient's body. Unlike Kirigami in which the planar material is folded before cutting, the kirigami-like cuts 800 can be made in the electrode layer 604, the flexible polymer layer 700 (or in some embodiments the conductive support layer 608), and the conductive gel element 588*a*, in some embodiments, when the electrode layer 604, the flexible polymer layer 700 (or in some embodiments the conductive support layer 608), and the conductive gel element 588*a* forming the pad 796 are bonded together, and in a planar, i.e., unfolded shape. The kirigami-like cuts 800 can be made utilizing any suitable automated cutter assembly that will cut through the electrode layer 604, the flexible polymer layer 700 (or in some embodiments the conductive support layer 608), and the conductive gel element 588*a*. In some embodiments, the conductive gel element 588*a* is in a polymerized state, rather than a liquid state when the kirigami-like cuts 800 are made.

In some embodiments, the automated cutter assembly may include a cutter, such as a die, a knife blade, a pressurized water-jet, or a laser. The cutter can be mounted on a translation assembly for moving the cutter in an at least one or more of an X, Y and Z plane to cause the cutter to cut and provide the kirigami-like cuts 800 in the predetermined pattern. For example, when the cutter is the die, the translation assembly may move the die in the Z plane to affect the die forming the kirigami-like cuts 800. When the cutter is a laser, the translation assembly may move the laser in the X and Y planes to form the kirigami-like cuts 800.

To make the pad 796, the durable topcoat layer 580*a*, the electrode layer 604, the flexible polymer layer 700 (or in some embodiments the conductive support layer 608), and the conductive gel element 588*a* (e.g., in a polymerized state) are overlapped and bonded together. A predetermined pattern of kirigami-like cuts 800 is determined so that the pad 796 will be able to conform to the predetermined part of the patient's body (e.g., without wrinkles) before or after the electrode layer 604, the flexible polymer layer 700 (or in some embodiments the conductive support layer 608), and the conductive gel element 588*a* are overlapped and bonded. Then, the cutter is used to provide the kirigami-like cuts through the durable topcoat layer 580*a*, the electrode layer 604, the flexible polymer layer 700 (or in some embodiments the conductive support layer 608), and the conductive gel element 588*a* simultaneously.

In some embodiments, a vacuum or other stabilization assembly may be used to keep the durable topcoat layer 580*a*, the electrode layer 604, the flexible polymer layer 700 (or in some embodiments the conductive support layer 608), and the conductive gel element 588*a* from moving relative to each other or wrinkling when the cutter is providing the kirigami-like cuts 800. In other embodiments, the durable topcoat layer 580*a*, the electrode layer 604, the flexible polymer layer 700 (or in some embodiments the conductive support layer 608), and the conductive gel element 588*a* can be cut by the cutter separately or in predetermined combinations, and then be overlapped and bonded together.

Once the kirigami-like cuts 800 are made, tension is applied to the conductive gel element 588*a* to stretch the conductive gel element 588*a* (and the other elements of the pad 796) outwardly to maintain an air gap within the kirigami-like cuts 800 to prevent parts of the conductive gel element 588*a* on opposite sides of a particular kirigami-like cut 800 from touching and bonding together.

Multiples of the pad 796 can be made in a continuous web-based process using a feed roller upstream of the cutter, and a bent roller and take-up roller downstream of the cutter. The continuous web may include the durable topcoat layer 580*a*, the electrode layer 604, the flexible polymer layer 700

(or in some embodiments the conductive support layer 608), and the conductive gel element 588*a* (e.g., in a polymerized state) are overlapped and bonded together. In this example, the rotational speeds of the feed roller and take-up roller would be set to provide a predetermined amount of tension into the web. The bent roller would provide lateral tension into the web. After the kirigami-like cuts 800 are made, the second removeable protection layer 176 can then be removably bonded to the bottom 664 of the conductive gel element 588*a* to protect the bottom 664 of the conductive gel element 588*a*. The second removeable protection layer 176 can be constructed of a material (e.g., plastic) that will maintain the tension in the conductive gel element 588*a*, such that the pad 796 can be packaged and shipped with the conductive gel element 588*a* in tension to prevent opposite sides of the conductive gel element 588*a* that were separated by the kirigami-like cuts 800 from touching and bonding together.

Embodiments of the pad 796 can be used in a similar manner as the pads 576 and 696 described above, for example. For the pad 796 to conform best to the body part of the patient, in some embodiments, the pad 796 may be placed on the patient when the patient is in a sitting, or non-supine, i.e., relaxed, position.

The following is a number list of non-limiting illustrative embodiments of the inventive concept of the eighth mode disclosed herein:

161. A system, comprising:

a generator configured to generate an electrical signal having an alternating current waveform at a frequency in a range from 50 kHz to 500 kHz;

a first conductive lead electrically coupled to the generator, the first conductive lead configured to carry the electrical signal;

a first pad having a first electrode element directly connected to a first conductive gel element, the first conductive element is configured to be in contact with a patient's skin, the first electrode element and the first conductive gel element define a plurality of kirigami-like cuts being a predetermined pattern of cuts resulting in the first pad conforming to a predetermined portion of a patient's body;

a second conductive lead electrically coupled to the generator, the second conductive lead configured to carry the electrical signal; and a second pad having a second electrode element directly connected to a second conductive gel element, and the second conductive gel element being configured to be in contact with a patient's skin.

162. The system of illustrative embodiment 161, wherein the first electrode element includes an electrode layer electrically coupled to a conductive support layer, the conductive support layer being intermediate to the electrode layer and the conductive gel element.

163. The system of illustrative embodiment 162, wherein the second electrode element includes an electrode layer electrically coupled to a conductive support layer, the conductive support layer being intermediate to the electrode layer and the conductive gel element.

164. The system of illustrative embodiment 161, further comprising a blocking capacitor configured to block direct current in the electrical signal.

165. The system of illustrative embodiment 164, wherein the blocking capacitor is a non-polarized capacitor.

166. The system of illustrative embodiment 164, wherein the blocking capacitor has a capacitance of about 1 μF.

167. The system of illustrative embodiment 164, wherein the generator includes the blocking capacitor.

168. The system of illustrative embodiment 164, wherein either the first pad, the second pad, or both the first pad and the second pad include the blocking capacitor.

169. The system of illustrative embodiment 164, wherein the blocking capacitor is a first blocking capacitor and further comprising a second blocking capacitor configured to block direct current in the electrical signal.

170. The system of illustrative embodiment 169, wherein either the first pad, the second pad, or both the first pad and the second pad include the second blocking capacitor.

171. The system of illustrative embodiment 161, wherein the first conductive gel element further includes a first hydrogel layer, a support layer, and a second hydrogel layer, the first hydrogel layer being a first electrically conductive hydrogel and the second hydrogel layer being a second electrically conductive hydrogel.

172. The system of illustrative embodiment 171, wherein the first electrically conductive hydrogel and the second electrically conductive hydrogel are not the same hydrogel.

173. The system of illustrative embodiment 171, wherein the support layer is electrically conductive.

174. The system of illustrative embodiment 161, wherein the second hydrogel element further includes a first hydrogel layer, a support layer, and a second hydrogel layer, the first hydrogel layer being a first electrically conductive hydrogel and the second hydrogel layer being a second electrically conductive hydrogel.

175. The system of illustrative embodiment 174, wherein the first electrically conductive hydrogel and the second electrically conductive hydrogel are not the same hydrogel.

176. The system of illustrative embodiment 174, wherein the support layer is electrically conductive.

177. The system of illustrative embodiment 161, further comprising one or more temperature sensor configured to measure a temperature of the first pad.

178. The system of illustrative embodiment 177, further comprising a control box configured to monitor the one or more temperature sensor and turn off the generator if the temperature exceeds a comfortability threshold.

179. The system of illustrative embodiment 178, wherein the comfortability threshold is about 40 degrees Celsius.

180. A pad, comprising:

a topcoat layer;

an electrode element connected to the topcoat layer, and configured to receive an electrical signal from a generator producing an electric signal as a TTField; and a conductive gel element directly connected to the electrode element so as to receive an electrical current from the electrode element, the conductive gel element configured to be in contact with a patient's skin, the electrode element and the conductive gel element defining kirigami-like cuts, the kirigrami-like cuts being a predetermined pattern of cuts that results in the electrode element and the conductive gel element forming a three-dimensional shape conforming to a predetermined portion of a patient's body.

181. The pad of illustrative embodiment 180, further comprising a conductive lead configured to carry the electrical signal, the conductive lead configured to be electrically coupled to the generator, the conductive lead electrically coupled to the electrode element.

182. The pad of illustrative embodiment 180, wherein the conductive gel element further includes a first conductive gel layer, a support layer, and a second conductive gel layer, the first hydrogel layer being a first electrically conductive gel and the second conductive gel layer being a second electrically conductive gel.

183. The pad of illustrative embodiment 182, wherein the first electrically conductive gel and the second electrically conductive gel are not the same conductive gel.

184. The pad of illustrative embodiment 182, wherein the support layer is electrically conductive.

185. The pad of illustrative embodiment 182, further comprising a blocking capacitor configured to block direct current in the electrical signal.

186. The pad of illustrative embodiment 185, wherein the blocking capacitor is a non-polarized capacitor.

187. The pad of illustrative embodiment 185, wherein the blocking capacitor has a capacitance of about 1 μF.

188. The pad of illustrative embodiment 180, wherein the topcoat layer, the electrode element, and the conductive gel element are constructed of flexible materials and configured to conform to a body of a patient.

189. A method, comprising:

applying at least two conductive regions to a skin of a patient, coupling the conductive regions to a generator before or after applying the at least two conductive regions to the patient, the generator configured to generate an electrical signal having an alternating current waveform at frequencies in the range from 50 kHz to 500 kHz, each conductive region having an electrode element and directly connected to a conductive gel element so as to supply an electrical current from the electrode element to the conductive gel element, the electrode elements being electrically coupled to the generator and, upon receiving the electrical signal supplies electrical current to the conductive gel element, the conductive gel element being in contact with a patient's skin, the electrode elements and the conductive gel elements including kirigami-like cuts resulting in the electrode elements and the conductive gel elements forming a three-dimensional shape conforming to a predetermined portion of a patient's body; and activating the generator to supply the electrical signal to the electrode elements, thereby supplying electrical current to the patient through the conductive gel element.

190. The method of illustrative embodiment 189 wherein coupling the conductive regions to the skin of the patient is defined further as connecting a first lead to a first one of the conductive regions, and connecting a second lead to a second one of the conductive regions.

191. The method of illustrative embodiment 189, further comprising the step of passing the electrical signal through a blocking capacitor configured to block direct current in the electrical signal.

192. The method of illustrative embodiment 191, wherein the blocking capacitor is a non-polarized capacitor.

193. The method of illustrative embodiment 191, wherein the blocking capacitor has a capacitance of about 1 μF.

194. The method of illustrative embodiment 189, wherein the electrode element, and the conductive gel element are constructed of flexible materials and configured to conform to a body of a patient, and wherein the step of applying at least two conductive regions to a skin of a patient is defined further as conforming the electrode element and the conductive gel element to the skin of the patient.

195. A system, comprising:

a generator configured to generate an electrical signal having an alternating current waveform at a frequency in a range from 50 kHz to 500 kHz;

a first conductive lead electrically coupled to the generator, the first conductive lead configured to carry the electrical signal;

a first pad having a first electrode element connected to a first flexible polymer layer, and a first conductive gel element, the first flexible polymer layer between the first electrode element and the first conductive gel element, the first conductive element being configured to be in contact with a patient's skin, the first electrode element, the first flexible polymer layer, and the first conductive gel element defining kirigami-like cuts resulting in the first electrode element, the first flexible polymer layer, and the first conductive gel element forming a three-dimensional shape conforming to a predetermined portion of a patient's body, the first flexible polymer layer being a first dielectric material;

a second conductive lead electrically coupled to the generator, the second conductive lead configured to carry the electrical signal; and a second pad having a second electrode element connected to a second flexible polymer layer, and a second conductive gel element, the second conductive gel element being configured to be in contact with the patient's skin, the second flexible polymer layer positioned in between the second electrode element and the second conductive gel element, and being a second dielectric material.

196. The system of illustrative embodiment 195, wherein the first electrode element includes an electrode layer electrically coupled to a conductive support layer, the conductive support layer being intermediate to the electrode layer and the first flexible polymer layer.

197. The system of illustrative embodiment 195, wherein the second electrode element includes an electrode layer electrically coupled to a conductive support layer, the conductive support layer being intermediate to the electrode layer and the first flexible polymer layer.

198. The system of illustrative embodiment 195, wherein the first conductive gel element further includes a first hydrogel layer, a support layer, and a second hydrogel layer, the first hydrogel layer being a first electrically conductive hydrogel and the second hydrogel layer being a second electrically conductive hydrogel.

199. The system of illustrative embodiment 198, wherein the first electrically conductive hydrogel and the second electrically conductive hydrogel are not the same hydrogel.

200. The system of illustrative embodiment 198, wherein the support layer is electrically conductive.

201. The system of illustrative embodiment 195, wherein the second hydrogel element further includes a first hydrogel layer, a support layer, and a second hydrogel layer, the first hydrogel layer being a first electrically conductive hydrogel and the second hydrogel layer being a second electrically conductive hydrogel.

202. The system of illustrative embodiment 201, wherein the first electrically conductive hydrogel and the second electrically conductive hydrogel are not the same hydrogel.

203. The system of illustrative embodiment 201, wherein the support layer is electrically conductive.

204. The system of illustrative embodiment 195, further comprising one or more temperature sensor configured to measure a temperature of the first pad.

205. The system of illustrative embodiment 204, further comprising a control box configured to monitor the one or more temperature sensor and turn off the generator if the temperature exceeds a comfortability threshold.

206. The system of illustrative embodiment 205, wherein the comfortability threshold is about 40 degrees Celsius.

207. A pad, comprising:

a topcoat layer;

an electrode element connected to the topcoat layer, and configured to receive an electrical signal from a generator producing an electric signal as a TTField;

a flexible polymer layer connected to the electrode element, the flexible polymer layer being constructed of a dielectric material; and a conductive gel element connected to the flexible polymer layer to electrically isolate the electrode element from the conductive gel element, the conductive gel element configured to be in contact with a patient's skin, the electrode element, the flexible polymer layer, and the conductive gel element define kirigami-like cuts, the kirigrami-like cuts being a predetermined pattern of cuts resulting in the electrode element, the flexible polymer layer, and the conductive gel element forming a three-dimensional shape conforming to a predetermined portion of a patient's body.

208. The pad of illustrative embodiment 207, further comprising a conductive lead configured to carry the electrical signal, the conductive lead configured to be electrically coupled to the generator, the conductive lead electrically coupled to the electrode element.

209. The pad of illustrative embodiment 207, wherein the conductive gel element further includes a first conductive gel layer, a support layer, and a second conductive gel layer, the first hydrogel layer being a first electrically conductive gel and the second conductive gel layer being a second electrically conductive gel.

210. The pad of illustrative embodiment 209, wherein the first electrically conductive gel and the second electrically conductive gel are not the same conductive gel.

211. The pad of illustrative embodiment 209, wherein the support layer is electrically conductive.

212. The pad of illustrative embodiment 209, further comprising a blocking capacitor configured to block direct current in the electrical signal.

213. The pad of illustrative embodiment 212, wherein the blocking capacitor is a non-polarized capacitor.

214. The pad of illustrative embodiment 212, wherein the blocking capacitor has a capacitance of about 1 μF.

215. A method, comprising:

applying at least two conductive regions to a skin of a patient;

coupling the conductive regions to a generator before or after applying the at least two conductive regions to the skin, the generator configured to generate an electrical signal having an alternating current waveform at frequencies in the range from 50 kHz to 500 kHz, each conductive region having an electrode element, flexible polymer layer, and a conductive gel element with the flexible polymer layer electrically isolating the electrode element from the conductive gel element, the electrode elements being electrically coupled to the generator and, upon receiving the electrical signal supplying an electric field to the conductive gel element through the flexible polymer layer, the conductive gel element being in contact with a patient's skin, the electrode elements, the flexible polymer layers, and the conductive gel element defining kirigami-like cuts, the kirigrami-like cuts being a predetermined pattern of cuts resulting in the electrode element, the flexible polymer layer, and the conductive gel element forming a three-dimensional shape conforming to a predetermined portion of a patient's body; and activating the generator to supply the electrical signal to the electrode elements, thereby supplying the electric field to the patient through the conductive gel element.

216. The method of illustrative embodiment 215 wherein coupling the conductive regions to the skin of the patient is defined further as connecting a first lead to a first one of the conductive regions, and connecting a second lead to a second one of the conductive regions.

217. The method of illustrative embodiment 215, further comprising the step of passing the electrical signal through a blocking capacitor configured to block direct current in the electrical signal.

218. The method of illustrative embodiment 217, wherein the blocking capacitor is a non-polarized capacitor.

219. The method of illustrative embodiment 217, wherein the blocking capacitor has a capacitance of about 1 μF.

220. The method of illustrative embodiment 215, wherein the electrode element, the flexible polymer layer, and the conductive gel element are constructed of flexible materials and configured to conform to a body of a patient, and wherein the step of applying at least two conductive regions to a skin of a patient is defined further as conforming the electrode element, the flexible polymer layer, and the conductive gel element to the skin of the patient.

Ninth Mode: Conductive and Non-Conductive Pads with Conductive Gel Designs and Applicator Thereof A ninth mode of the present disclosure includes a method of making a pad configured to deliver tumor treating fields into a patient. A nozzle of an applicator is positioned at an application distance from a first side of an electrode element. A conductive gel is selectively ejected from the nozzle at an application pressure, and the nozzle is translated relative to the electrode element during ejection of the conductive gel so as to form at least one line of conductive gel on the first side of the electrode element.

Figure 36:
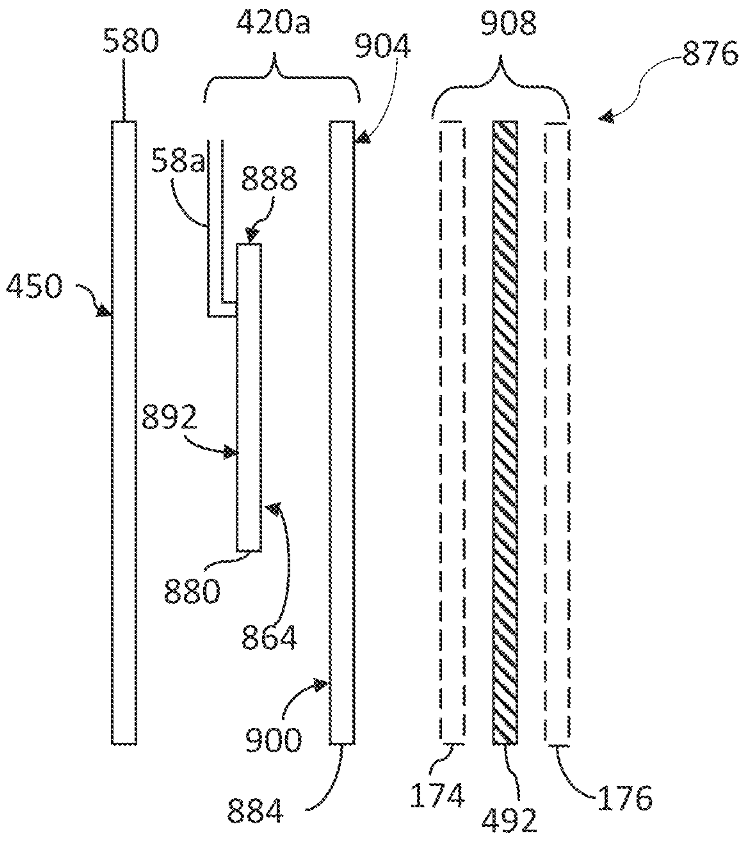
FIG. 36 is an exploded side view of an exemplary embodiment of the first pad depicted in FIG. 2.

Shown in FIG. 36 is an exploded side view of one embodiment of a first conductive pad 876 constructed in accordance with the present disclosure. The first conductive pad 876 is an exemplary embodiment of the pad 70*a* and the pad 70*b*. The first conductive pad 876 is similar in construction and function as the conductive pad 100*f*, with the exception that the first conductive pad 876 is provided with an electrode element 420*a* that is formed of an electrode layer 880, and a conductive support layer 884 connected to the electrode layer 880. The electrode layer 880 overlaps the conductive support layer 884. The electrode layer 880 includes an outer peripheral electrode edge 888. The conductive support layer 884 may extend beyond the outer peripheral electrode edge 888 of the electrode layer 880. The first conductive pad 876 may also be referred to as an electrode, such as the first electrode 18*a* or the second electrode 18*b*, or electrode pad.

The electrode layer 880 may be selected from any conductive material having desirable properties such as, but not limited to, high conductivity, strong biocompatibility, and low reactivity with other layers or components of the first conductive pad 876. In one embodiment, the electrode layer

880 is selected from one or more of the following: silver, tin, aluminum, titanium, platinum, an alloy thereof, and/or some combination thereof. The electrode layer 880 includes a first surface 892 in contact with a durable topcoat layer 580 and a second surface 896 in contact with the conductive support layer 884. The durable topcoat layer 580 may be a non-conductive material, such as a non-conductive fabric. The non-conductive fabric may have a plurality of perforations 412, and desirably many perforations 412.

In one embodiment, the electrode layer 880 may be bonded to the conductive support layer 884. The conductive support layer 884 may include a first surface 900 attached to or otherwise coupled to the second surface 896 of the electrode layer 880 and a second surface 904 in direct contact with a conductive gel element 908. In some embodiments, an entirety of the second surface 904 is in direct contact with the conductive gel element 908. The conductive support layer 884 may be formed of a conductive carbon film (or conductive fabric) configured to support the electrode layer 880 while also conductively coupling the electrode layer 880 to the conductive gel element 908. In one embodiment, the conductive support layer 884 may be electroplated, or otherwise bonded, to the electrode layer 880. In this embodiment, the first conductive pad 876 does not include a dielectric layer electrically isolating the electrode element 420*a* from the conductive gel element 908. Exemplary embodiments of the conductive fabric are discussed above.

In one embodiment, a thickness of the electrode layer 880, or alternatively the thickness of the electrode layer 880 and the conductive support layer 884, may be determined based on the current and the frequency of the electric signal used to generate the TTField. The thickness may also be set based on other desirable properties such as heat dissipation and/or flexibility requirements of the first conductive pad 876, for example. For example, if the thickness is too thin, the patient may experience hot spots, that is, the patient may experience portions of the first conductive pad 876 heating more rapidly than other portions of the first conductive pad 876, which may be due, at least in part, to the thickness slowing thermal conductivity within the electrode layer 880, thus causing an increase in temperature differentials across the first conductive pad 876. In one embodiment, the thickness is between 25 mil and 75 mil.

In one embodiment, the first conductive pad 876 may be shaped at a point of use (e.g., with scissors) to correspond to the target area of the patient. For example only and not by way of limitation, the first conductive pad 876 may be cut, or otherwise modified, to remove a portion of the first conductive pad 876 in order to accommodate an ear wherein the portion removed would otherwise be over the ear. By doing so, better adhesion of the first conductive pad 876 to the patient's head may be achieved as well as an increase in comfort of the patient. As another example, the first conductive pad 876 may be cut or otherwise modified to fit around a joint of the patient, such as, and not limited to, cutting the first conductive pad 876 that is placed on a patient's knee in a manner that would allow the patient to continue to use their knee while the first conductive pad 876 is attached, or, further, use their knee while undergoing treatment from TTFields. Shaping of the first conductive pad 876 can be pre-structured or the first conductive pad 876 can be made sufficiently flexible so that shaping of the first conductive pad 876 is readily achievable. One important consideration when modifying the first conductive pad 876 is any cut through the electrode layer 880 such that a portion of the first conductive pad 876 is electrically isolated from the remainder of the first conductive pad 876 may have adverse therapeutic consequences.

Figure 37:
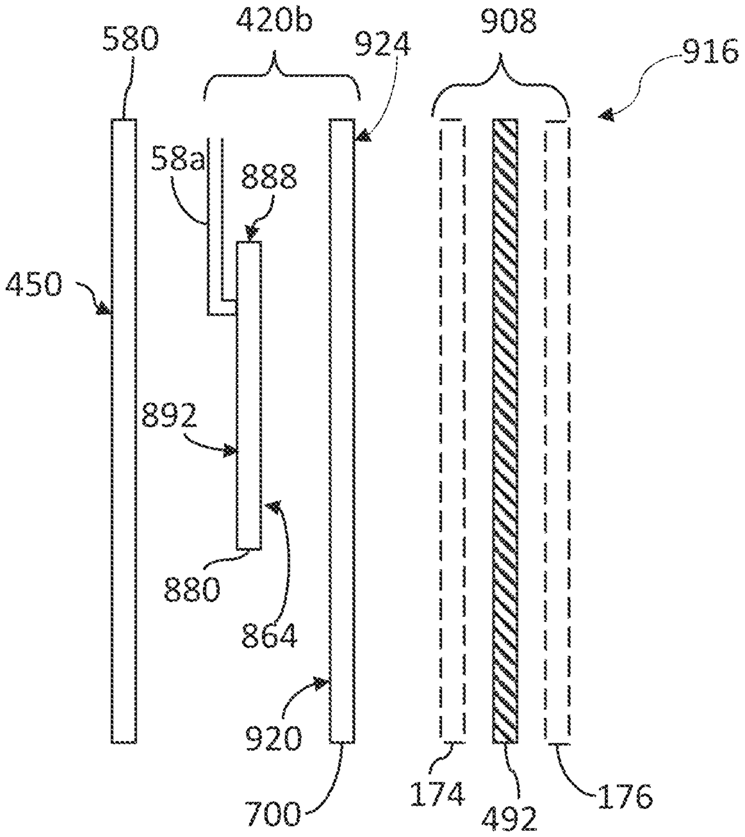
FIG. 37 is an exploded side view of an exemplary embodiment of the first pad depicted in FIG. 2.

Referring to FIG. 37, shown therein is another embodiment of a pad 916 constructed in accordance with the present disclosure. The pad 916 is similar in construction and function to the first conductive pad 876 described above with respect to FIG. 36, with the exception that the pad 916 includes an electrode element 420*b* that includes the non-conductive flexible polymer layer 700 (referred to hereinafter as the flexible polymer layer 700) rather than the conductive support layer 884. In this embodiment, the conductive support layer 884 may be omitted, and the flexible polymer layer 700 is positioned between the electrode layer 880 and the conductive gel element 908. Elements common between the pad 916 and the first conductive pad 876 are labeled with common reference numerals.

The flexible polymer layer 700 may be constructed of a dielectric material as discussed above. The flexible polymer layer 700 may be provided with a first surface 920, and a second surface 924. The first surface 920 may be attached to or otherwise coupled to the second surface 864 of the electrode layer 880 and the second surface 924 may be in direct contact with the conductive gel element 908. In some embodiments, an entirety of the first surface 920 is in direct contact with the second surface 184*e* of the electrode layer 880, and the second surface 924 is in direct contact with the conductive gel element 908.

In some embodiments, the conductive gel layer 492 of the conductive pads 876 or 916 may include conductive gel having one or more pattern. Referring now to FIG. 38A-F, shown therein are various alternative, exemplary embodiments of the conductive pads 876 or 916 having the conductive gel layer 492 with conductive gel in various patterns. Because the conductive fabric 400 may have a different ability to flex and/or stretch when conductive gel is not present compared to when conductive gel is present, selection of a pattern for the conductive gel of the conductive gel layer 492 may be dependent on a desired flexibility and a desired stretchability of the conductive pads 876 or 916. For example only, if it is desired to place the conductive pads 876 or 916 on a patient's joint having one degree of freedom, such as a patient's elbow, it may be desirable to have the conductive pads 876 or 916 with a flexibility that would allow the patient to use their elbow without such use causing the conductive pad 100*f* to move on the patient's body and/or cause the patient pain.

Figure 38A:
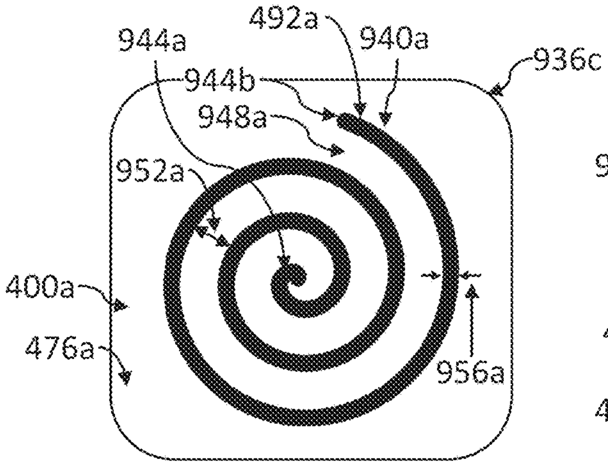
FIG. 38A is a bottom plan view of an exemplary embodiment of a conductive pad having a conductive gel layer constructed in accordance with the present disclosure.

Referring to FIG. 38A, shown therein is a bottom plan view of an exemplary embodiment of a conductive pad 936*c* having a first side 476*a* of conductive fabric 400*a* and further including a conductive gel layer 492*a*. The conductive pad 936*c* is identical in construction and function as the conductive pad 100*f*, the conductive pad 876, and the pad 916 described above, with the exception that the conductive gel layer 492 is arranged to form one or more pattern of conductive gel having at least one line 940*a* with adjacent portions as described in more detail below. The conductive gel layer 492*a* is formed of a conductive gel as described above. The conductive gel of the conductive gel layer 492*a* is shown disposed on the first side 476*a* of the conductive fabric 400*a* by way of example, as the line 940*a* in a spiral pattern. In other embodiments, the conductive gel layer 492*a* is disposed on the conductive support layer 884, or the flexible polymer layer 700. The line 940*a* has a first end 944*a* and a second end 944*b*. While the spiral pattern shown in FIG. 38A is shown as a circular spiral extending in a counterclockwise direction, the spiral pattern is not limited to a type of spiral or the counterclockwise direction and may include other types of spirals and may be in a clockwise direction. Also shown in FIG. 38A is an air-channel 948*a*. The air-channel 948*a* is bound by the first side 476*a* and by the conductive gel of adjacent portions of the line 940*a* of the conductive gel layer 492*a*. The air-channel 948*a* may include a width 952*a* formed by conductive gel disposed on either side of the air-channel 948*a*. The width 952*a* may be substantially uniform, or varying along the line 940*a*. In some embodiments, the air-channel 948*a* extends adjacent to the line 940*a* from the first end 944*a* to the second end 944*b* thereof.

The conductive gel of the conductive gel layer 492*a* further includes a gel width 956*a*. In one embodiment, the width 952*a* and the gel width 956*a* are substantially equal, however, in other embodiments, the gel width 956*a* may be greater than or less than the width 952*a*. In one embodiment, the gel width 956*a* and the width 952*a* are approximately one-eighth (⅛) of an inch. In other embodiments the gel width 956*a* is between approximately one-thousandth (1/1000) of an inch and approximately one (1) inch and/or the width 952*a* is between approximately one-thousandth (1/1000) of an inch and approximately one (1) inch. In one embodiment, selection of the width 952*a* is based at least in part on a desired flexibility, such that for increased flexibility in a first direction may result in a greater width 952*a* in the first direction and for increased flexibility in a second direction may result in a greater width 952*a* in the second direction.

Figure 38B:
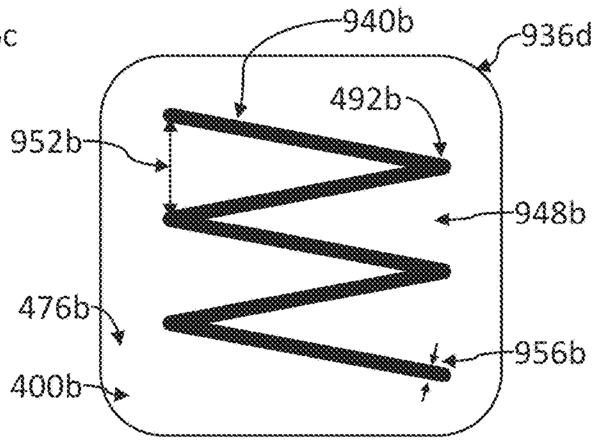
FIG. 38B is a bottom plan view of another exemplary embodiment of a conductive pad having a conductive gel layer constructed in accordance with the present disclosure.

Referring to FIG. 38B, shown therein is a bottom plan view of an exemplary embodiment of a conductive pad 936*d* having a first side 476*b* of conductive fabric 400*b* and further including a conductive gel layer 492*b*. The conductive pad 936*d* is identical in construction and function as the conductive pad 936*c* described above, with the exception that the conductive gel layer 492*b* is arranged to form one or more pattern of conductive gel arranged as a line 940*b* in a zig-zag pattern. In other embodiments, the conductive gel layer 492*b* is disposed on the conductive support layer 884, or the flexible polymer layer 700. While the zig-zag pattern shown in FIG. 38B is shown as a zig-zag pattern having a left to right direction, the zig-zag pattern is not limited to a type of zig-zag pattern or the left to right direction and may include other types of zig-zag patterns and may instead be in another direction, such as up and down. Also shown in FIG. 38B is an air-channel 948*b*. The air-channel 948*b* is bound by the first side 476*b* and by adjacent portions of the line 940*b* of the conductive gel of the conductive gel layer 492*a*. The air-channel 948*b* may include a width 952*b* formed by conductive gel disposed on either side of the air-channel 948*b*.

Figure 38C:
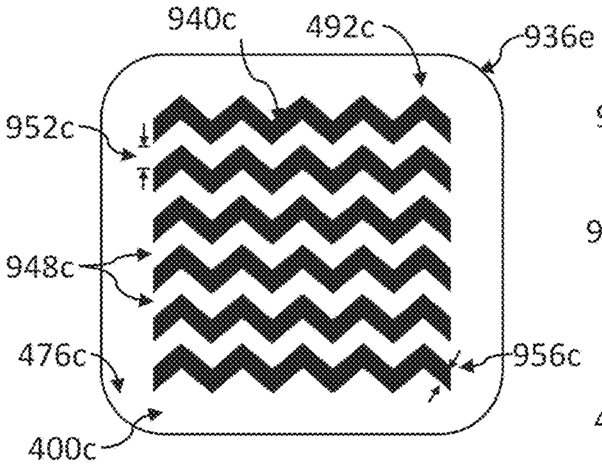
FIG. 38C is a bottom plan view of another exemplary embodiment of a conductive pad having a conductive gel layer constructed in accordance with the present disclosure.

Referring to FIG. 38C, shown therein is a bottom plan view of an exemplary embodiment of a conductive pad 936*e* having a first side 476*c* of conductive fabric 400*c* and further including a conductive gel layer 492*c*. The conductive pad 936*e* is identical in construction and function as the conductive pad 936*c* described above, with the exception that the conductive gel layer 492*c* is arranged to form a plurality of lines 940*c* of conductive gel of the conductive gel layer 492*c* disposed on the first side 476*c* of the conductive fabric 400*c* in a chevron pattern. In other embodiments, the conductive gel layer 492*c* is disposed on the conductive support layer 884, or the flexible polymer layer 700. While the chevron pattern shown in FIG. 38C is shown in a left to right direction having a first number of chevrons, the chevron pattern is not limited to extending left to right, and the first number of chevrons may have any number of chevrons. Also shown in FIG. 38C is a plurality of air-channels 948*c*. Each air-channel 948*c* is bound by the first side 476*c* and by adjacently disposed conductive gel of the conductive gel layer 492*c*. Each air-channel 948*c* may include a width 952*c* formed by adjacently disposed conductive gel.

Figure 38D:
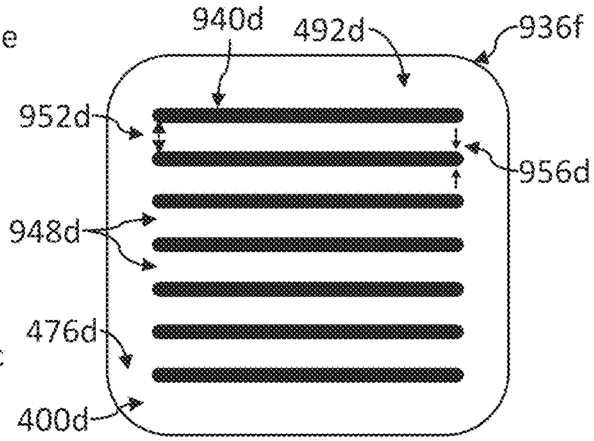
FIG. 38D is a bottom plan view of another exemplary embodiment of a conductive pad having a conductive gel layer constructed in accordance with the present disclosure.

Referring to FIG. 38D, shown therein is a bottom plan view of an exemplary embodiment of a conductive pad 936*f* having a first side 476*d* of conductive fabric 400*d* and further including a conductive gel layer 492*d*. The conductive pad 936*f* is identical in construction and function as the conductive pad 936*c* described above, with the exception that the conductive gel layer 492*d* is arranged to form a plurality of linear lines 940*d* of a conductive gel as described above. In the embodiment shown, the linear lines 940*d* are parallel. The conductive gel of the conductive gel layer 492*d* is disposed on the first side 476*a* of the conductive fabric 400*d* in a spaced apart linear pattern. In other embodiments, the conductive gel layer 492*d* is disposed on the conductive support layer 884, or the flexible polymer layer 700. While the linear pattern shown in FIG. 38D is shown extending left to right, the linear pattern can extend in other orientations and/or directions. Also shown in FIG. 38D is a plurality of air-channels 948*d*. Each air-channel 948*d* is bound by the first side 476*d* and by the conductive gel of the conductive gel layer 492*d*. Each air-channel 948*d* may include a width 952*d* formed by adjacently disposed conductive gel.

Figure 38E:
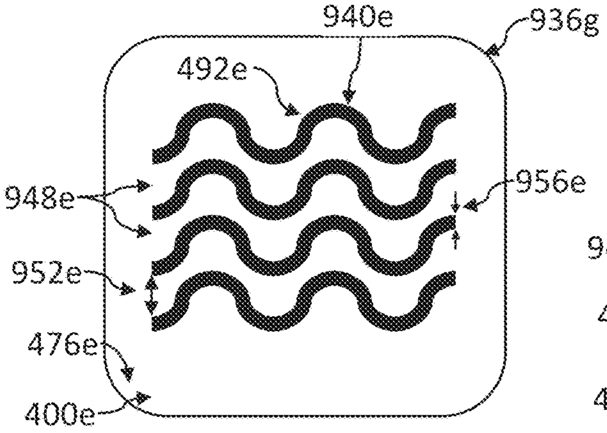
FIG. 38E is a bottom plan view of another exemplary embodiment of a conductive pad having a conductive gel layer constructed in accordance with the present disclosure.

Referring to FIG. 38E, shown therein is a bottom plan view of an exemplary embodiment of a conductive pad 936*g* having a first side 476*e* of conductive fabric 400*e* and further including a conductive gel layer 492*e*. The conductive pad 936*g* is identical in construction and function as the conductive pad 936*c* described above, with the exception that the conductive gel layer 492*e* is disposed on the first side 476*e* of the conductive fabric 400*e* as a plurality of lines 940*e* in an in-phase sinusoidal pattern. In other embodiments, the conductive gel layer 492*e* is disposed on the conductive support layer 884, or the flexible polymer layer 700. While the sinusoidal pattern shown in FIG. 38E is shown extending left to right, the sinusoidal pattern is not limited to left or right and may have a second direction different from the first direction. Also shown in FIG. 38E is a plurality of air-channels 948*e*. Each air-channel 948*e* is bound by the first side 476*e* and by the conductive gel of the conductive gel layer 492*e*. Each air-channel 948*e* may include a width 952*e* formed by adjacently disposed conductive gel.

Figure 38F:
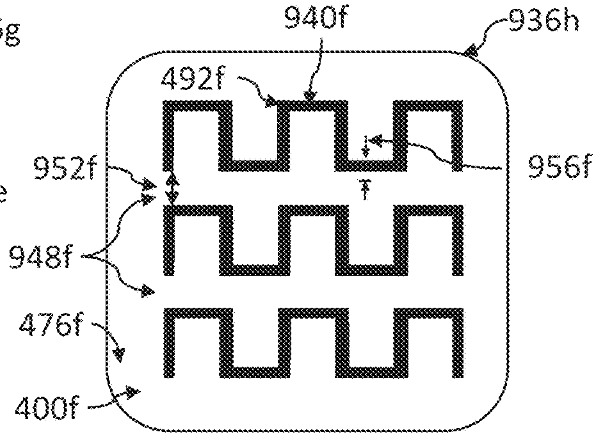
FIG. 38F is a bottom plan view of another exemplary embodiment of a conductive pad having a conductive gel layer constructed in accordance with the present disclosure.

Referring to FIG. 38F, shown therein is a bottom plan view of an exemplary embodiment of a conductive pad 936*h* having a first side 476*f* of conductive fabric 400*f* and further including a conductive gel layer 492*f*. The conductive pad 936*h* is identical in construction and function as the conductive pad 936*c* described above, with the exception that the conductive gel layer 492*f* is disposed on the first side 476*f* of the conductive fabric 400*f* in an in-phase square-wave pattern. In other embodiments, the conductive gel layer 492*f* is disposed on the conductive support layer 884, or the flexible polymer layer 700. While the square-wave linear pattern shown in FIG. 38F is shown as going from left to right, the square-wave pattern is not limited to going from left to right and other directions may be used. Also shown in FIG. 38F is a plurality of air-channels 948*f*. Each air-channel 948*f* is bound by the first side 476*f* and by adjacent sections of the lines 940*f* of the conductive gel of the conductive gel layer 492*f*. Each air-channel 948*f* may include a width 952*f* formed by adjacently disposed conductive gel.

Figure 39:
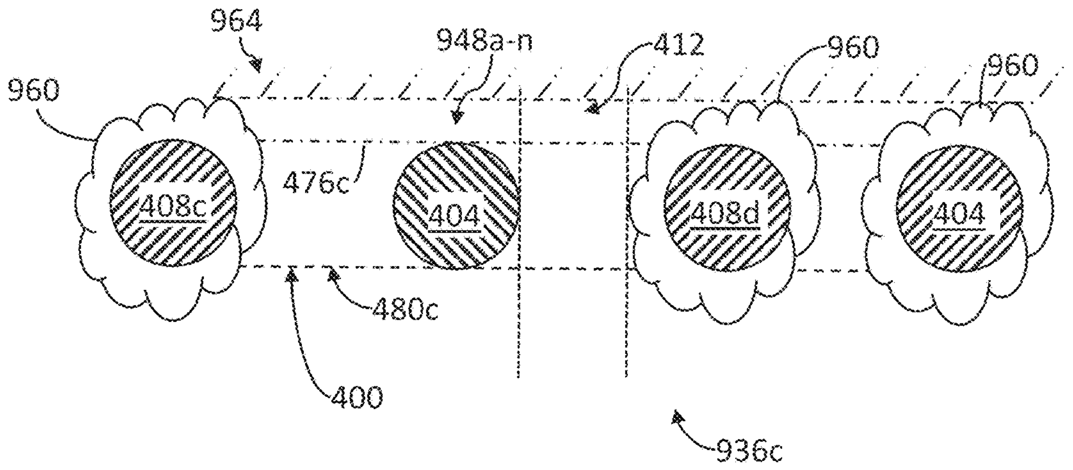
FIG. 39 is a partial, cross-sectional diagram of a conductive pad constructed in accordance with the present disclosure.

Referring now to FIG. 39, shown therein is a partial cross-sectional view of the conductive pad 936*c*. The conductive fabric 400 is permeated by a conductive gel 960 such as the conductive gel or the semi-solid conductive gel of the conductive gel layer 492, or a liquid conductive gel such as described below. The conductive fabric 400 is constructed as described above and includes a conductive thread 408*c*, a nonconductive thread 404, and a conductive thread 408*d*. The conductive gel 960, when applied, e.g., as described below in conductive gel application process 1046, penetrates the conductive fabric 400 and thus permeates through the threads of the conductive fabric 400 as shown by the conductive gel 960 surrounding the conductive thread 408*c* and the conductive thread 408*d*. In some embodiments, the conductive gel 960 also surrounds one or more nonconductive thread 404. When the conductive gel 960 surrounds one or more of the conductive thread 408*a-n* and/or the nonconductive thread 404, the conductive gel 960 may be said to be "bonded" to the conductive fabric 400. Moreover, by surrounding each conductive thread 408 with the conductive gel 960, a contact area between each conductive thread 408 and the conductive gel 960 is increased. For example, if a particular conductive thread 408 is surrounded by the conductive gel 960, then the contact area between the particular conductive thread 408 and the conductive gel 960 is approximately equal to a surface area of the particular conductive thread 408.

Further shown, a void formed between adjacent threads, such as the conductive thread 408*d* and the nonconductive thread 404, establishes the one or more perforation 412, as described in more detail above. Also shown is a cross-section of an air-channel 948*a-n* formed by a void between the first side 476 of the conductive fabric 400, the conductive gel 960 surrounding the conductive thread 408*c*, the conductive gel 960 surrounding the conductive thread 408*d*, and a patient 964.

Figure 40:
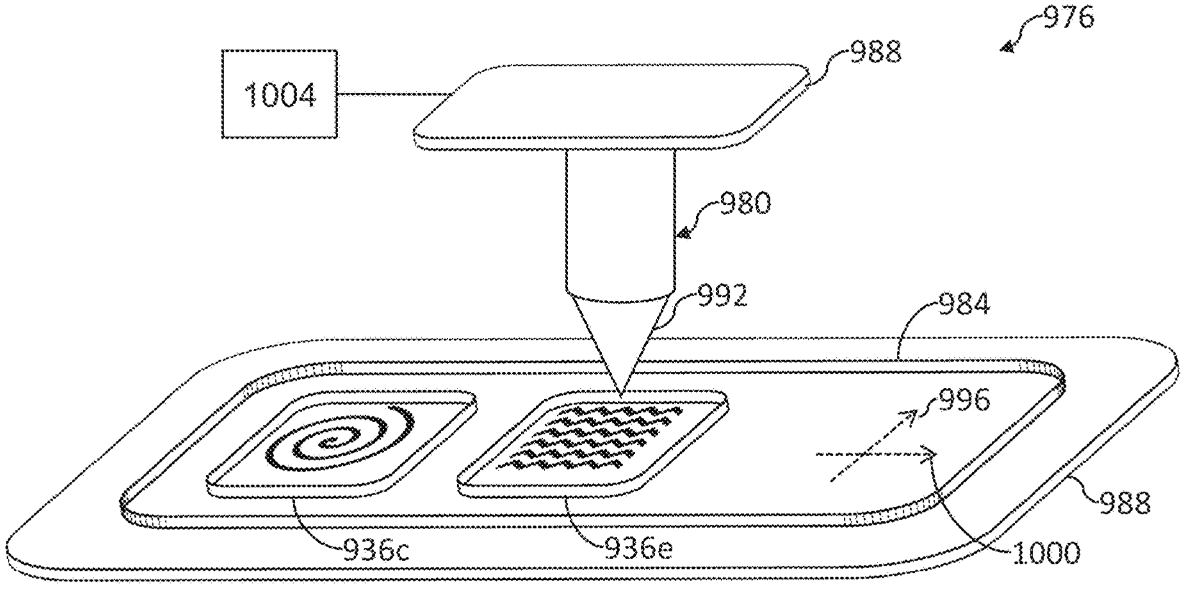
FIG. 40 is a perspective diagram of an exemplary embodiment of a gel application system constructed in accordance with the present disclosure.

Referring now to FIG. 40, shown therein is a diagram of an exemplary embodiment of a gel application system 976 constructed in accordance with the present disclosure. The gel application system 976 comprises one or more applicator 980 and a platform 984 moveably attached to a housing 988. Only one applicator 980 is shown for purposes of brevity. It should be understood that multiple applicators 980 can be used to form any of the conductive pads 936*e-h* having more than one line 940. Further multiple applicators 980 can be used to form multiple pads 100*f*, 876, 916, or 936*c-h* simultaneously. The one or more applicator 980 further comprises at least a nozzle 992 to eject a conductive gel, described in more detail above. The platform 984 supports one or more pad 100*f*, 876, 916, or 936*c-h*, shown in FIG. 39 as the conductive pad 936*c* and the conductive pad 288. In one embodiment, the applicator 980 may move in one of a first direction 996 or a second direction 1000 or a combination of the first direction 996 and the second direction 1000. In one embodiment, the platform 984 may move in one of the first direction 996 or the second direction 1000 or a combination of the first direction 996 and the second direction 1000. In one embodiment, the gel application system 976 includes a controller 1004 to control movement of the platform 984 and/or to control movement of the applicator 980.

In one embodiment, the nozzle 992 has an application distance determined by the distance between the nozzle 992 from the platform 984, and ejects conductive gel (in liquid form) at an application pressure, and moves at an application velocity relative to the platform 984. By adjusting the application distance, the application pressure, and the application velocity, the gel width 956, e.g., the gel width 956*a-f*, is adjusted. For example, ejecting gel at a first application distance, a first application pressure, and a first application velocity may result in a first gel width whereas ejecting gel at the first application distance, the first application pressure, and a second application velocity greater than the first application velocity, may result in a second gel width lesser than the first gel width. The application velocity may be caused by moving the applicator 980 and/or the platform 984 in one of the first direction 996, the second direction 1000, or the combination of the first direction 996 and the second direction 1000.

In one embodiment, the application pressure is selected such that a portion of the conductive gel is wicked into and/or through the conductive fabric 400, e.g., the portion of the conductive gel is passed through the plurality of perforations 412 of the conductive fabric 400 such that a contact area, that is an area of the conductive threads 408*a-n* and the nonconductive threads 404 of which the conductive gel is in contact, is increased. A portion of the conductive gel is also positioned on the first side 476 to engage the patient 964 and form the air-channels 948. For example, it may be desirable to eject conductive gel at a higher pressure to cause the conductive gel to penetrate further into the conductive fabric 400. By increasing penetration into the conductive fabric 400, additional conductive threads 408*a-n* may be exposed to the conductive gel, thus potentially increasing electrical conductivity to enhance an amount of current of the TTF fields that can be applied to the patient 964. In another embodiment, tension may be applied or adjusted on the conductive fabric 400 to adjust penetration of the conductive gel. In another embodiment, the application pressure and the tension are selected based at least in part on a desired penetration of the conductive gel into the conductive fabric 400.

In one embodiment, the gel application system 976 ejects conductive gel in a liquid form onto the conductive fabric 400, the conductive support layer 884, or the flexible polymer layer 700. In some embodiments including the conductive fabric 400, by ejecting the conductive gel in liquid form, the liquid conductive gel can better penetrate the conductive fabric 400. Additionally, the liquid conductive gel may be wicked further into the conductive fabric 400. In one embodiment, the liquid conductive gel further comprises a curing agent that, when cured, encapsulates one or more conductive threads 408*a-n* and/or one or more nonconductive threads 404. For example, the liquid conductive gel may include a UV curing agent such that when the liquid conductive gel is exposed to a particular UV source, the liquid conductive gel is cured, i.e., is polymerized. In embodiments including the conductive support layer 884, or the flexible polymer layer 700, the polymerized liquid conductive gel may be on the surface of the conductive support layer 884 or the flexible polymer layer 700 without any penetration into the conductive support layer 884 or the flexible polymer layer 700. The polymerization of the liquid conductive gel, which has penetrated the conductive fabric 400, encapsulates the one or more conductive threads 408*a-n* and/or one or more nonconductive threads 404 of the conductive fabric 400, thereby increasing conductivity between the polymerized conductive gel and the conductive fabric 400 as well as bonding the polymerized conductive gel at a particular location on and/or within the conductive fabric 400. In one embodiment, the liquid conductive gel is ejected at an application pressure of approximately 60 psi. In other embodiments, the liquid conductive gel is ejected at an application pressure of between approximately 30 psi and approximately 90 psi.

In one embodiment, the platform 984 includes a sheet of non-conductive fabric and one or more conductive fabric 400 is attached to the non-conductive fabric. In one embodiment, each conductive fabric 400 is attached to the non-conductive fabric (e.g., platform 984) such that a pocket is formed between the non-conductive fabric and the conductive fabric 400. The pocket may be operable to receive the fabric support element 466. Each pocket may be spatially disposed such that the conductive fabric 400 of a first pocket is not in electrical contact with the conductive fabric 400 of a second pocket. An embodiment further describing multiple conductive regions is shown in FIG. 41 and described in more detail below.

In one embodiment, the applicator 980 may be hand-held, that is, the applicator 980 may be held and/or moved by a user instead of being moveably attached to the housing 988. In such an embodiment, the user may use the applicator 980 to eject conductive gel onto conductive fabric 400 or a pad 100*f*, 876, 916, or 936*c-h*. For example, if the pad 100*f*, 876, 916, or 936*c-h* is washed or otherwise cleared of conductive gel, the user may use the applicator 980 to re-apply conductive gel to the pad 100*f*, 876, 916, or 936*c-h*.

Figure 41:
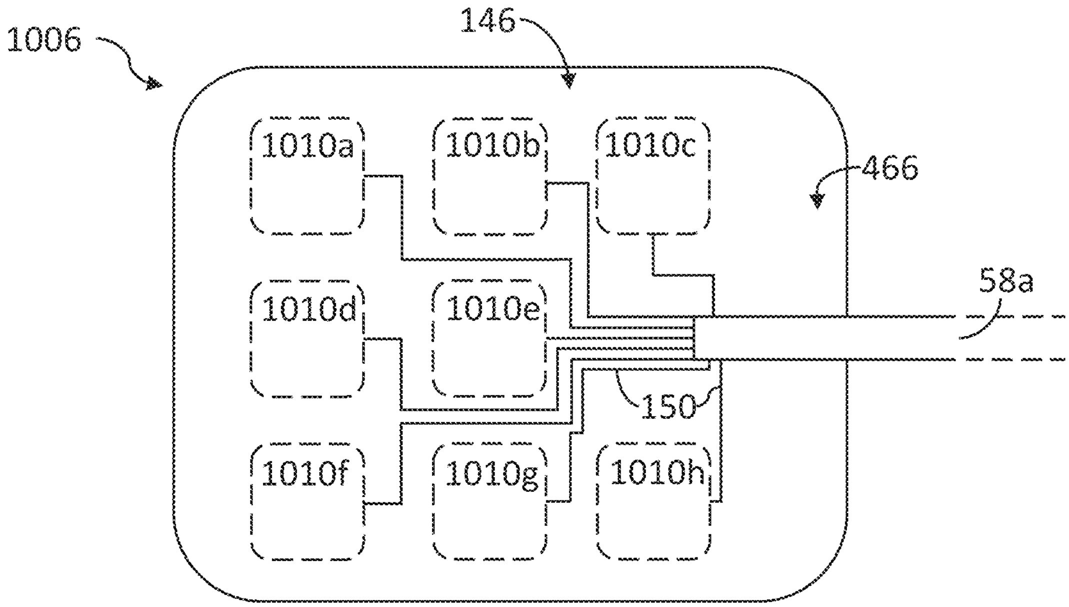
FIG. 41 is a functional diagram of another exemplary embodiment of a conductive pad constructed in accordance with the present disclosure.

Referring to FIG. 41, shown therein is a functional diagram of an exemplary embodiment of a conductive pad 1006. The conductive pad 1006 is identical in construction and function as the conductive pad 100*f*, the conductive pad 876, and the pad 936 described above, with the exception that the electrode elements 420, 420*b*, and 420*a* are arranged to form a plurality of conductive regions 1010*a-h*. Eight conductive regions 1010*a-h* are shown in FIG. 41 by way of example. When the conductive pad 1006 includes the conductive fabric 400, the conductive pad 1006 includes the fabric support element 466 extending over and between the conductive regions 1010*a-h*. In this embodiment, the fabric support element 466 may be formed of a non-conductive material, or be formed of an electrically conductive material that does not receive any electrical current from the conductive regions 1010*a-h*. The conductive regions 1010*a-h* are electrically isolated by one or more dielectric region 146 extending between each adjacently disposed pair of conductive regions 1010*a-h*. The dielectric region 146 can be formed by interleaving a dielectric element laterally between each pair of adjacently disposed conductive regions 1010*a-h*. The lead 58*a* may include two or more isolated conductor 150 such that each conductive region 1010*a-h* is coupled to the generator 54 independently, thus allowing the generator 54 to independently control the TTField generated by each conductive region 1010*a-h*. In such an embodiment, the electronic apparatus 50 may alternate between one or more conductive region 1010*a-h* of the conductive pad 1006, thus creating and shaping TTFields with increased specificity and precision. A single conductive pad 1006 having multiple conductive regions 1010*a-h*, can be used as a substitute or in conjunction with the first conductive pad 100*a*, the second conductive pad 100*b*, or any of conductive pads 936*c-h*.

In one embodiment, the conductive pad 1006 is formed in the shape of an article of clothing as described above in more detail. For example, the conductive pad 1006 may be formed into a shirt having the plurality of conductive regions 1010*a-h*. The plurality of conductive regions 1010*a-h* may be selectively activated such that a TTField is generated to target a tumor at a particular location within the patient's abdomen or chest. Alternatively, the conductive pad 1006 may be formed into a hat having the plurality of conductive regions 1010*a-h*. The plurality of conductive regions 1010*a-h* may be selectively activated such that a TTField is generated to target a tumor at a particular location within the patient's head.

In one embodiment, one or more conductive region 1010 may be placed on the conductive gel element 908 such that each conductive region 1010 is electrically isolated from each other conductive region 1010. By way of example, a first conductive region 1010 (e.g., the conductive region 1010*a*) may be placed at a first position on a first conductive gel element 908 and a second conductive region 1010 (e.g., the conductive region 1010*b*) may be placed at a second position on a second conductive gel element 908. The first position and the second position may be disposed such that the first position and the second position do not overlap and are separate from each other whereby the first conductive region 1010 and the second conductive region 1010 are electrically isolated from one another. In one embodiment, a ratio between the surface area of each conductive region 1010 and a surface area of the combined conductive gel elements 908 is 50/50. In another embodiment, a ratio between the surface area of each conductive region 1010 and a surface area of the combined conductive gel elements 908 is 70/30 respectively. In one embodiment, each conductive region 1010 may have the same or a different shape. For example, the conductive region 1010*a* may be a strip having a length greater than a width whereas the conductive region 1010*b* may be substantially circular in shape.

In one embodiment, the generator 54, connected to the conductive pad 1006, may supply a first electric signal having a first power and a first frequency to a first group of one or more conductive region 1010*a-h* (e.g., conductive region 1010*a* and conductive region 1010*b*, for example) at a first instance in time to generate a first TTField. The generator 54, at a second instance in time, may supply a second electric signal having a second power, the same as or different from the first power, and a second frequency, the same as or different from the first frequency, to a second group of one or more conductive region 1010*a-h* (e.g., conductive region 1010*b* and conductive region 1010*c*, for example) to generate a second TTField. The second group may include one or more conductive region 1010*a-h* included in the first group, or may not include one or more conductive region 1010*a-h* included in the first group. The first TTField and the second TTField may target the same target area or may target different target areas. In one embodiment, the first instance in time and the second instance in time may overlap, that is, the generator 54 may supply the second electric signal to the second group while also supplying the first electric signal to the first group. In such an embodiment, the first group and the second group may be mutually exclusive.

In one embodiment, the generator 54, connected to the conductive pad 1006, may supply a first electrical signal having a first power and a first frequency to a first group of one or more conductive region 1010*a-h* (e.g. conductive region 1010*a* and conductive region 1010*b*, for example) and supply a second electrical signal having a second power and a second frequency to a second group of one or more conductive region 1010*a-h* (e.g. conductive region 1010*b* and conductive region 1010*c*, for example) at the same instance in time. That is, the generator 54, may simultaneously supply the first electric signal to the first group and the second electric signal to the second group. While the above embodiments describe only the first group and the second group, it is understood that there may be more than two groups. In one embodiment, the number of groups is dependent on the number of combinations of the conductive regions 1010*a-h*.

In one embodiment, the generator 54 may be connected to the conductive pad 1006 and the second conductive pad 100*b*. In such an embodiment, the generator 54 may supply the electric signal to the one or more conductive region

1010*a-h* of the conductive pad 1006. The one or more conductive region 1010*a-h* receiving the electric signal may then generate a TTField between each of the one or more conductive region 1010*a-h* of the conductive pad 1006 and the second conductive pad 100*b*.

Certain non-limiting embodiments of the present disclosure are related to kits that include any of the components of the TTField generating systems, such as the electronic apparatus 50, described herein. In one embodiment, one or more of the conductive pad 100*f* and the second conductive pad 100*b* may be packaged as part of a kit. In one embodiment, the kit may include the pad 100*f*, 876, 916, or 936*c-h* and the lead 58*a* connected to the electrode element 420, or 420*a*. In another embodiment, the kit may include the conductive pad 100*f* and the second conductive pad 100*b*, and the leads 58*a* and 58*b*. In each of the above embodiments, the lead 58*a* may be mechanically coupled to the conductive pad 100*f*, and the lead 58*b* may be mechanically coupled to the second conductive pad 100*b*, for example, by a rivet, by solder, by adhesive, by welding, or other electrically conductive coupling means. In each of the above embodiments, the kit may further include the blocking capacitor 82*a* or the blocking capacitor 82*b* positioned such that the electric signal passes through the blocking capacitor 82*a* or the blocking capacitor 82*b*. In each of the above embodiments, the conductive pad 100*f* and/or the second conductive pad 100*b* may include the second removeable protection layer 176 attached to and covering at least a portion of (or the entirety of) the conductive gel element 908 such that the second removeable protection layer 176 protects the conductive gel element 908 from potential damage, such as loss of adhesion or disruption of or discontinuities. The second removeable protection layer 176 may be easily removed by the user before the conductive pad 100*f* and/or the second conductive pad 100*b* is applied to the patient. In one embodiment, the second removeable protection layer 176 is an electric insulator, such that the second removeable protection layer 176 prevents or substantially reduces accidental application of the electric signal before the conductive pad 100*f* and/or the second conductive pad 100*b* is attached to the patient. In each of the above embodiments, the kit may include more than the conductive pad 100*f* and the second conductive pad 100*b*, and may include a number of conductive pads (constructed in accordance with the present disclosure) that, when applied to the patient, have a therapeutic benefit. In addition, the kit can further include a set of written instructions explaining how to use one or more components of the kit. A kit of this nature can be used in any of the methods described or otherwise contemplated herein. In one embodiment, the conductive pad 1006 or one or more of the conductive pads 936*c-h* may be used instead of either the conductive pad 100*f* or the second conductive pad 100*b*, or both, in the abovementioned kit.

Figure 42:
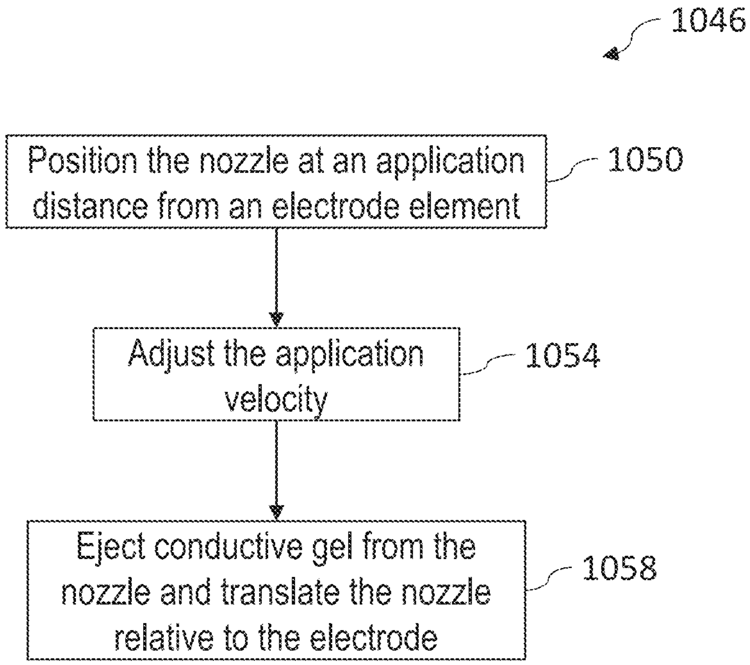
FIG. 42 is a process diagram of an exemplary embodiment of a conductive gel application process for applying the conductive gel layer of the present disclosure.

Referring now to FIG. 42, shown therein is a process diagram of an exemplary embodiment of a conductive gel application process 1046. The conductive gel application process 1046 generally includes the steps of: positioning an ejection point (e.g., nozzle 992) at an application distance from the conductive fabric 400 of the electrode element 420, the conductive support layer 884 of the electrode element 420*a*, or the flexible polymer layer 700 of the electrode element 420*b* (step 1050); adjusting the application velocity (step 1054); and ejecting conductive gel from the ejection point (e.g., nozzle 992) at an application pressure (step 1058).

In one embodiment, the step of positioning the ejection point at an application distance from the conductive fabric 400 (step 1050), for example, may include positioning the nozzle 992 at the application distance from the conductive fabric 400. Additionally, positioning the ejection point at an application distance from the conductive fabric 400 (step 1050) may include selecting the application distance such that, in combination with the application velocity and the application pressure, the conductive gel, once bonded to the conductive fabric 400, has a desired gel width 956.

In one embodiment, the step of adjusting the application velocity (step 1054) may include selecting the application velocity such that, in combination with the application distance and the application pressure, the conductive gel, once bonded to the conductive fabric 400, has the desired gel width 956.

In one embodiment, the step of adjusting the application velocity (step 1054) includes moving the conductive fabric 400 from a first location to a second location for a first duration while not changing a location of the ejection point, while in another embodiment, the step of adjusting the application velocity (step 1054) includes moving the ejection point from a third location to a fourth location for a second duration while not changing a location of the conductive fabric 400.

In yet another embodiment, the step of adjusting the application velocity (step 1054) includes moving the conductive fabric 400 from a first location to a second location for a first duration while simultaneously moving the ejection point from a third location to a fourth location for a second duration. The first duration and the second duration may be the same or different.

In one embodiment, the step of ejecting conductive gel from the ejection point at an application pressure (step 1058) and translating the nozzle 992 relative to the conductive fabric 400, the conductive support layer 884, or the flexible polymer layer 700, may include selecting the application pressure such that, in combination with the application velocity and the application distance, the conductive gel, once bonded to the conductive fabric 400, the conductive support layer 884, or the flexible polymer layer 700 has the desired gel width 956. Translating the nozzle 992 relative to the conductive fabric 400, the conductive support layer 884, or the flexible polymer layer 700 may include moving the nozzle 992 while maintaining the conductive fabric 400, the conductive support layer 884, or the flexible polymer layer 700 in a stationary location; moving the conductive fabric 400, the conductive support layer 884, or the flexible polymer layer 700 while maintaining the nozzle 992 in a stationary location; or moving both the nozzle 992 and the conductive fabric 400, the conductive support layer 884, or the flexible polymer layer 700.

In one embodiment, the step of ejecting conductive gel from the ejection point at an application pressure may include ejecting conductive gel for a first period of time and not ejecting conductive gel for a second period of time. In one embodiment, ejecting conductive gel from the ejection point at an application pressure (step 1058) may include ejecting conductive gel at a pressure of approximately 60 psi. In another embodiment, ejecting conductive gel from the ejection point at an application pressure (step 1058) may include ejecting conductive gel at a pressure of between approximately 30 psi and approximately 90 psi. In yet another embodiment, ejecting conductive gel from the ejection point at an application pressure (step 1058) may include ejecting conductive gel from the nozzle 992 and simultaneously translating the nozzle 992 relative to the conductive fabric 400 to form the one or more lines 940 of conductive gel.

In one embodiment, the conductive gel of the conductive gel application process 1046 is a liquid conductive gel and step 1058 includes ejecting liquid conductive gel from the ejection point at the application pressure. In another embodiment, the liquid conductive gel further comprises a curing agent. In such an embodiment, the conductive gel application process 1046 may further include a step of curing the liquid conductive gel. In one embodiment, the step of curing the liquid conductive gel may be performed with a UV source causing the liquid conductive gel to polymerize and bond to one or more conductive thread 408 or one or more nonconductive thread 404 of the conductive fabric 400, or the conductive support layer 884, or the flexible polymer layer 700.

Figure 43:
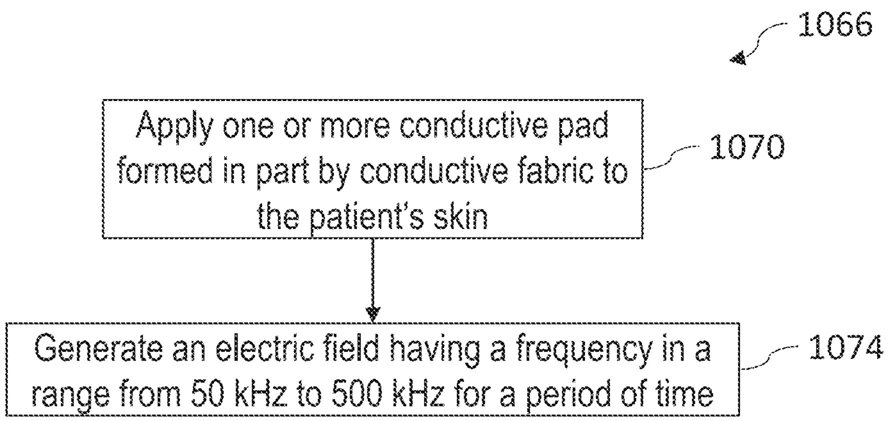
FIG. 43 is a process diagram of an exemplary embodiment of a process of treating a tumor utilizing the conductive pads of the present disclosure.

Referring now to FIG. 43, shown therein is a process diagram of an exemplary embodiment of a process 1066 of using the electronic apparatus 50 and two or more of the conductive pads 100*a*, 100*f*, 876, 916, 936*c-h* and/or the conductive pad 1006 to apply a TTField to a patient. The process 1066 generally comprises the steps of: applying one or more of the pads 100*a*, 100*f*, 936*c-h* and/or the conductive pad 1006 to the patient's skin (step 1070) and generating an alternating electric field having a frequency in a range of from about 50 kHz to about 576 kHz for a period of time (step 1074). The process 1066 will be described in relation to applying two of the conductive pads 876, however, the conductive pad 1006 and/or one or more of the pads 100*f*, 916, or 936*c-h* may be used in replacement of or in addition to the conductive pads 876.

The step 1070 of applying the conductive pads 876 to the patient's skin may be performed by the user. In one embodiment, before applying the conductive pads 876 to the patient's skin, the patient's skin may need to be cleaned (e.g., such as but not limited to, cleansing of the skin of foreign matter or biological matter and shaving of the skin, if necessary) to enable each conductive pad 876 to adhere to the patient's skin. In one embodiment, at least a portion of the first side 476 of the conductive fabric 400 and the conductive gel layer 492 may be in direct contact with the patient's skin. Additionally, the conductive fabric 400 can supply the TTF field to the patient through the conductive gel layer 492.

The step of generating an alternating electric field (TTField) (step 1074) may be performed by the generator 54 and may be instantiated by an operation performed by the user or control box 66. In one embodiment, step 1074 may be performed more than one time and the period of time for which the step 1074 is performed a first time may be the same as or different from the period of time for which the step 1074 is performed a second time (or other period(s) of time beyond the second time). In some embodiments, step 1074 is only performed once before the process 1066 is repeated. There may be a time period between each time the process 1066 is repeated. Each time the process 1066 is repeated, the time period may be the same as or different from the previous time period. Each time the process 1066 is repeated, the conductive pads 876 may be placed in the same or a different position on the patient's skin.

During the process 1066, applying the conductive pads 876, one or more of the pads 100*f*, 916, or 936*c-h*, and/or the conductive pad 1006 to the patient's skin (step 1070) may result in the conductive pads 876, one or more of the pad 100*f*, 916, or 936*c-h*, and/or the conductive pad 1006 being attached to the patient's skin for an extended period of time.

The following is a number list of non-limiting illustrative embodiments of the inventive concept of the ninth mode disclosed herein:

221. A system, comprising:
a generator configured to generate an electrical signal having an alternating current waveform at a frequency in a range from 50 kHz to 500 kHz;
a first conductive lead electrically coupled to the generator, the first conductive lead configured to carry the electrical signal;
a first conductive pad having a first electrode element electrically coupled to the first conductive lead, the first electrode element having a first side to be disposed towards a patient's body, and a first conductive gel element bonded to the first side of the first conductive fabric, the first conductive gel element being in the form of at least one line, and operable to be placed in contact with a patient's skin at a selected location and operable to flex with movement of the patient without substantially moving from the selected location;
a second conductive lead electrically coupled to the generator, the second conductive lead configured to carry the electrical signal; and
a second conductive pad having a second electrode element electrically coupled to the second conductive lead.

222. The system of illustrative embodiment 221, wherein the first conductive gel element covers a first region of the first side and does not cover a second region of the first side.

223. The system of illustrative embodiment 221, wherein the first electrode element comprises a first conductive fabric including non-conductive threads connected to conductive threads.

224. A conductive pad, comprising:
a topcoat layer constructed of a non-conductive material;
an electrode element having a first side and a second side, the second side connected to the topcoat layer, and configured to receive an electrical signal from a generator producing an electric signal as a TTField; and
a conductive gel element connected to the first side of the electrode element and electrically coupled to the electrode element so as to receive an electrical current from the electrode element, the conductive gel element being in the form of at least one line and operable to be in contact with a patient's skin at specific locations and operable to flex with movement of the patient without substantially moving from the specific location.

225. The conductive pad of illustrative embodiment 224, wherein the conductive gel element covers a first region of the first side and does not cover a second region of the first side.

226. The conductive pad of illustrative embodiment 224, wherein the electrode element comprises a conductive fabric including non-conductive threads connected to conductive threads.

227. A method of making a pad configured to deliver tumor treating fields into a patient, the method comprising:
positioning a nozzle of an applicator at an application distance from a first side of an electrode element; selectively ejecting conductive gel from the nozzle at an application pressure; and
translating the nozzle relative to the electrode element during ejection of the conductive gel so as to form at least one line of conductive gel on the first side of the electrode element.

228. The method of illustrative embodiment 227, wherein the electrode element comprises conductive fabric, and wherein ejecting conductive gel from the nozzle at an application pressure to form a conductive gel element is defined further as ejecting conductive gel from the nozzle at an application pressure to form a conductive gel element so as to penetrate the conductive fabric with the conductive gel element.

229. The method of illustrative embodiment 227, wherein ejecting conductive gel from the nozzle at an application pressure to form the conductive gel element is defined further as ejecting conductive gel from the nozzle at an application pressure so as to form the line having a particular gel width.

230. The method of illustrative embodiment 227, wherein positioning a nozzle of an applicator at an application distance from a first side of the electrode element is defined further as positioning a nozzle of an applicator at an application distance from a first side of the electrode element so as to form the line having a particular gel width.

231. The method of illustrative embodiment 227, wherein adjusting an application velocity is defined further as adjusting an application velocity so as to form the conductive gel element having a particular gel width.

232. The method of illustrative embodiment 227, wherein ejecting conductive gel from the nozzle at an application pressure to form a conductive gel element is further defined as ejecting conductive gel from the nozzle at an application pressure of approximately 60 psi to form a conductive gel element.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concepts disclosed and claimed herein.

The foregoing description provides illustration and description, but is not intended to be exhaustive or to limit the inventive concepts to the precise form disclosed. Modifications and variations are possible in light of the above teachings or may be acquired from practice of the methodologies set forth in the present disclosure.

Even though particular combinations of features and steps are recited in the claims and/or disclosed in the specification, these combinations are not intended to limit the disclosure. In fact, many of these features and steps may be combined in ways not specifically recited in the claims and/or disclosed in the specification. Although each dependent claim listed below may directly depend on only one other claim, the disclosure includes each dependent claim in combination with every other claim in the claim set.

Similarly, although each illustrative embodiment listed above may directly depend on only one other illustrative embodiment, the disclosure includes each illustrative embodiment in combination with every other illustrative embodiment in the set of illustrative embodiments for each mode of the inventive concepts disclosed herein.

No element, act, or instruction used in the present application should be construed as critical or essential to the invention unless explicitly described as such outside of the preferred embodiment. Further, the phrase "based on" is intended to mean "based, at least in part, on" unless explicitly stated otherwise.

What is claimed is:

1. A system, comprising:

a generator configured to generate an electrical signal as a TTField having an alternating current waveform at a frequency in a range from 50 kHz to 500 kHz;

a first conductive lead electrically coupled to the generator, the first conductive lead configured to carry the electrical signal;

a first pad having a first electrode element electrically coupled to the first conductive lead, the first electrode element having a first side to be disposed towards a patient's body, and a first conductive gel element bonded to the first side, the first conductive gel element comprising at least one line of conductive gel forming one or more of a chevron pattern and a sinusoidal pattern on the first side of the first electrode element and defining, in conjunction with the first side of the first electrode element, at least one air channel having an air channel width, the first conductive gel element operable to be placed in contact with a patient's skin at a selected location and operable, at least in part based on the one or more of the chevron pattern and the sinusoidal pattern, to flex with movement of the patient without substantially moving from the selected location;

a second conductive lead electrically coupled to the generator, the second conductive lead configured to carry the electrical signal; and a second conductive pad having a second electrode element electrically coupled to the second conductive lead.

2. The system of claim 1, wherein the first conductive gel element covers a first region of the first side and does not cover a second region of the first side.

3. The system of claim 1, wherein the first electrode element comprises a first conductive carbon layer or a first conductive fabric including non-conductive threads connected to conductive threads.

4. A pad, comprising:

a topcoat layer constructed of a non-conductive material;

an electrode element having a first side to be disposed towards a patient's body and a second side, the second side connected to the topcoat layer, and configured to receive an electrical signal from a generator producing an electric signal as a TTField; and a conductive gel element electrically connected to the first side of the electrode element and electrically coupled to the electrode element so as to receive an electrical current from the electrode element, the conductive gel element comprising at least one line of conductive gel forming one or more of a chevron pattern and a sinusoidal pattern on the first side of the electrode element and defining, in conjunction with the first side of the electrode element, at least one air channel having an air channel width, the conductive gel element operable to be in contact with a patient's skin at specific locations and operable, at least in part based on the one or more of the chevron pattern and the sinusoidal pattern, to flex with movement of the patient without substantially moving from the specific location.

5. The pad of claim 4, wherein the conductive gel element covers a first region of the first side and does not cover a second region of the first side.

6. The pad of claim 4, wherein the electrode element comprises a conductive fabric including non-conductive threads connected to conductive threads.

7. The pad of claim 4, wherein the pad is a conductive pad.

8. The pad of claim 7, wherein the electrode element comprises an electrode layer and a conductive support layer.

9. The pad of claim 8, wherein the conductive support layer is a conductive carbon layer configured to conductively couple the electrode layer to the conductive gel element or a conductive fabric configured to conductively couple the electrode layer to the conductive gel element.

10. The pad of claim 4, wherein the pad includes a dielectric layer electrically isolating the electrode element from the conductive gel element.

11. The pad of claim 10, wherein the electrode element comprises an electrode layer, and wherein the dielectric layer is positioned between the electrode layer and the conductive gel element.

12. The pad of claim 10, wherein the dielectric layer is a flexible polymer layer.

13. The pad of claim 4, wherein the at least one line of conductive gel is two or more lines of conductive gel and wherein the two or more lines of conductive gel form an in-phase sinusoidal pattern.

14. A method of making a pad configured to deliver tumor treating fields into a patient, the method comprising:

positioning a nozzle of an applicator at an application distance from a first side of an electrode element of the pad;

selectively ejecting conductive gel from the nozzle at an application pressure; and translating the nozzle relative to the electrode element during ejection of the conductive gel so as to form at least one line of the conductive gel in one or more of a chevron pattern and a sinusoidal pattern on the first side of the electrode element and defining, in conjunction with the first side of the electrode element, at least one air channel having an air channel width, wherein the air channel width is selected at least in part based on one or more of an amount of desired flexibility of the pad and a direction of desired flexibility of the pad, such that a greater air channel width results in increased flexibility of the pad in the direction of the air channel width the at least one line of the conductive gel operable to be in contact with a patient's skin at specific locations and operable to flex with movement of the patient without substantially moving from the specific location.

15. The method of claim 14, wherein the electrode element comprises conductive fabric, and wherein ejecting the conductive gel from the nozzle at an application pressure is defined further as ejecting the conductive gel from the nozzle at an application pressure so as to penetrate the conductive fabric with the conductive gel.

16. The method of claim 14, wherein ejecting the conductive gel from the nozzle at an application pressure is defined further as ejecting the conductive gel from the nozzle at an application pressure so as to form the line having a particular gel width.

17. The method of claim 14, wherein positioning a nozzle of an applicator at an application distance from a first side of the electrode element is defined further as positioning a nozzle of an applicator at an application distance from the first side of the electrode element so as to form the line having a particular gel width.

18. The method of claim 14, comprising adjusting an application velocity so as to form the at least one line of the conductive gel having a particular gel width.

19. The method of claim 14, wherein ejecting conductive gel from the nozzle at the application pressure to form the at least one line of the conductive gel is further defined as ejecting conductive gel from the nozzle at an application pressure of approximately 60 psi to form the at least one line of the conductive gel.

* * * * *